US007404956B2

(12) United States Patent
Peters et al.

(10) Patent No.: US 7,404,956 B2
(45) Date of Patent: Jul. 29, 2008

(54) IMMUNOGLOBULIN CHIMERIC MONOMER-DIMER HYBRIDS

(75) Inventors: Robert T. Peters, West Roxbury, MA (US); Adam R. Mezo, Waltham, MA (US); Daniel S. Rivera, Providence, RI (US); Alan J. Bitonti, Acton, MA (US); Susan C. Low, Pepperell, MA (US)

(73) Assignee: Syntonix Pharmaceuticals, Inc., Waltham, MA (US)

( * ) Notice: Subject to any disclaimer, the term of this patent is extended or adjusted under 35 U.S.C. 154(b) by 423 days.

(21) Appl. No.: 10/841,250

(22) Filed: May 6, 2004

(65) Prior Publication Data
US 2005/0032174 A1 Feb. 10, 2005

Related U.S. Application Data

(60) Provisional application No. 60/539,207, filed on Jan. 26, 2004, provisional application No. 60/487,964, filed on Jul. 17, 2003, provisional application No. 60/469,600, filed on May 6, 2003.

(51) Int. Cl.
*A61K 39/00* (2006.01)
*C07K 16/00* (2006.01)
*C07K 1/00* (2006.01)
*C07K 14/00* (2006.01)
*C12P 21/08* (2006.01)

(52) U.S. Cl. .............. 424/178.1; 530/387.1; 530/387.3; 530/391.7; 530/402

(58) Field of Classification Search ............... 424/133.1
See application file for complete search history.

(56) References Cited

U.S. PATENT DOCUMENTS

| 3,941,763 | A | 3/1976 | Sarantakis |
| 4,695,623 | A | 9/1987 | Stabinsky .................. 530/351 |
| 4,784,950 | A | 11/1988 | Hagen et al. |
| 4,897,471 | A | 1/1990 | Stabinsky .................... 536/27 |
| 5,077,204 | A | 12/1991 | Brake et al. ................ 435/68.1 |
| 5,093,246 | A | 3/1992 | Cech et al. |
| 5,116,964 | A | 5/1992 | Capon et al. .................. 536/27 |
| 5,162,220 | A | 11/1992 | Oshima et al. ............. 435/224 |
| 5,175,096 | A | 12/1992 | Hook et al. |
| 5,189,015 | A | 2/1993 | Hook et al. |
| 5,234,830 | A | 8/1993 | Oshima et al. ........... 435/252.3 |
| 5,258,498 | A | 11/1993 | Huston et al. ............... 530/350 |
| 5,428,130 | A | 6/1995 | Capon et al. ................ 530/350 |
| 5,464,933 | A | 11/1995 | Bolognesi et al. |
| 5,480,981 | A | 1/1996 | Goodwin et al. ........... 536/23.5 |
| 5,482,858 | A | 1/1996 | Huston et al. .......... 435/252.33 |
| 5,579,277 | A | 11/1996 | Bolognsi et al. |
| 5,585,089 | A | 11/1996 | Kelly |
| 5,591,573 | A | 1/1997 | Whalen et al. |
| 5,605,689 | A | 2/1997 | Ammann |
| 5,624,821 | A | 4/1997 | Winter et al. ............... 435/69.6 |
| 5,648,240 | A | 7/1997 | Ammann et al. |
| 5,723,125 | A | 3/1998 | Chang et al. ............. 424/134.1 |
| 5,739,277 | A | 4/1998 | Presta et al. |
| 5,807,706 | A | 9/1998 | Carter et al. ............... 435/69.1 |
| 5,808,029 | A | 9/1998 | Brockhaus et al. ......... 536/23.5 |
| 5,885,821 | A | 3/1999 | Magota et al. .............. 435/224 |
| 5,910,573 | A | 6/1999 | Pluckthun et al. |
| 6,013,263 | A | 1/2000 | Barney et al. ............. 424/212.1 |
| 6,015,881 | A | 1/2000 | Kang et al. .................. 530/339 |
| 6,017,536 | A | 1/2000 | Barney et al. ............. 424/188.1 |
| 6,030,613 | A | 2/2000 | Blumberg et al. ........ 424/134.1 |
| 6,060,065 | A | 5/2000 | Barney et al. ............ 424/209.1 |
| 6,068,973 | A | 5/2000 | Barney et al. ................... 435/5 |
| 6,086,875 | A | 7/2000 | Blumberg et al. ........ 424/134.1 |
| 6,093,799 | A | 7/2000 | Li et al. ..................... 530/334 |
| 6,184,344 | B1 | 2/2001 | Kent et al. |
| 6,228,983 | B1 | 5/2001 | Barney et al. ............... 530/300 |
| 6,281,331 | B1 | 8/2001 | Kang et al. |
| 6,310,180 | B1 | 10/2001 | Tam |
| 6,310,183 | B1 | 10/2001 | Johannessen et al. |
| 6,326,468 | B1 | 12/2001 | Canne et al. |

(Continued)

FOREIGN PATENT DOCUMENTS

EP 0 325 262 A2 7/1989

(Continued)

OTHER PUBLICATIONS

Baru et al. Liposome-encapsulated DNA-mediated gene transfer and synthesis of human factor IX in mice. Gene 1995, vol. 161, p. 143-150.*

(Continued)

*Primary Examiner*—Bruce R. Campell
*Assistant Examiner*—Louise Humphrey
(74) *Attorney, Agent, or Firm*—Finnegan, Henderson, Farabow, Garrett & Dunner, LLP

(57) ABSTRACT

The invention relates to a chimeric monomer-dimer hybrid protein wherein said protein comprises a first and a second polypeptide chain, said first polypeptide chain comprising at least a portion of an immunoglobulin constant region and a biologically active molecule, and said second polypeptide chain comprising at least a portion of an immunoglobulin constant region without the biologically active molecule of the first chain. The invention also relates to methods of using and methods of making the chimeric monomer-dimer hybrid protein of the invention.

48 Claims, 27 Drawing Sheets

U.S. PATENT DOCUMENTS

| | | | |
|---|---|---|---|
| 6,329,176 B1 | 12/2001 | Woldike et al. | |
| 6,469,136 B1 | 10/2002 | Bray et al. | |
| 6,475,491 B1 | 11/2002 | Johnson et al. | |
| 6,485,726 B1 | 11/2002 | Blumberg et al. | 424/178.1 |
| 6,518,013 B1 | 2/2003 | Barney et al. | |
| 6,660,843 B1 | 12/2003 | Feige et al. | |
| 2002/0081664 A1 | 6/2002 | Lo et al. | 435/69.5 |
| 2002/0106374 A1 | 8/2002 | Olson et al. | |
| 2003/0053984 A1* | 3/2003 | Tschopp et al. | 424/85.1 |
| 2003/0119727 A1* | 6/2003 | Dennis et al. | 514/9 |
| 2003/0180287 A1 | 9/2003 | Gambotz et al. | |
| 2003/0235536 A1 | 12/2003 | Blumberg et al. | 424/45 |
| 2004/0077022 A1 | 4/2004 | Feige et al. | |
| 2005/0027109 A1 | 2/2005 | Mezo et al. | |
| 2005/0037941 A1 | 2/2005 | Bitonti et al. | |

FOREIGN PATENT DOCUMENTS

| | | |
|---|---|---|
| FR | 2 641 468 A | 7/1990 |
| WO | WO 88/09810 | 12/1988 |
| WO | WO 89/10134 | 2/1989 |
| WO | WO 90/11364 | 10/1991 |
| WO | WO 92/10209 | 6/1992 |
| WO | WO 93/11162 | 6/1993 |
| WO | WO 00/18881 A2 | 5/2000 |
| WO | WO 01/02439 | 1/2001 |
| WO | WO 01/36637 | 5/2001 |
| WO | WO 01/58935 | 8/2001 |
| WO | WO 01/91780 | 12/2001 |
| WO | WO 02/18417 | 3/2002 |
| WO | WO 02/46208 | 6/2002 |
| WO | WO 02/089828 | 11/2002 |
| WO | 03/077834 | 9/2003 |
| WO | WO 03/077834 | 9/2003 |
| WO | WO 2004/03176 | 1/2004 |
| WO | WO 2004/006962 | 1/2004 |
| WO | WO 2004/101740 | 11/2004 |
| WO | WO 2005/001025 | 1/2005 |

OTHER PUBLICATIONS

International Search Report for PCT/US04/14064 dated Apr. 6, 2006.
Ghetie et al., "Multiple Roles for the Major Histocompatibility Complex Class I-Related Receptor FcRn," *Annu. Rev. Immunol.*, 18:739-766 (2000).
Jelesarov et al., "Thermodynamic Characterization of the Coupled Folding and Association of Heterodimeric Coiled Coils (Leucine Zippers)," *J. Mol. Biol.*, 263:344-358 (1996).
Swaminathan et al., "Affinity Purification of Recombinant Interferon-α on a Mimetic Ligand Adsorbent," *Protein Expression and Purification*, 15:236-242 (1999).
Aruffo et al., "CD44 Is the Principal Cell Surface Receptor for Hyaluronate," *Cell* 61:1303 (1990).
Ashkenazi et al., "Protection against endotoxic shock by a tumor necrosis factor receptor immunoadhesin," *Proc. Natl. Acad. Sci. USA* 88:10535 (1991).
Bennett et al., "Extracellular Domain-IgG Fusion Proteins for Three Human Natriuretic Peptide Receptors," *J. Biol. Chem.* 266:23060 (1991).
Brennan et al., "Preparation of Bispecific Antibodies by Chemical Recombination of Monoclonal Immunoglobulin $G_1$ Fragments," *Science* 229:81 (1985).
Byrn et al., "Biological properties of a CD4 immunoadhesin," *Natur*, 344:667 (1990).
Capon et al., "Designing CD4 immunoadhesins for AIDS therapy," *Nature* 337:525 (1989).
Chalupny et al., "T-cell activation molecule 4-1BB binds to extracellular matrix proteins," *Proc. Natl. Acad. Sci. USA* 89:10360 (1992).
Dawson et al., "Synthesis of Native Proteins by Chemical Ligation," *Annu. Rev. Biochem.* 69:923 (2000).
Gascoigne et al., "Secretion of a chimeric T-cell receptor-immunoglobulin protein," *Proc. Natl. Acad. Sci. USA* 84:2936 (1987).

Kostelny et al., "Formation of a bispecific antibody by the use of leucine zippers," *J. Immunol.* 148(5):1547 (1992).
Kurschner et al., "Construction, Purification, and Characterization of New Interferon $Y$ ($IFN_y$) Inhibitor Proteins," *J. Biol. Chem* 267:9354 (1992).
Lesslauer et al., "Recombinant soluble tumor necrosis factor receptor proteins mice from lipopolysaccharide-induced lethality," *Eur. J. Immunol.* 21:2883 (1991).
Linsley et al., "Binding of the B Cell Activation Antigen B7 to CD28 Costimulates T Cell Proliferation and Interleukin 2 mRNA Accumulation," *J. Exp. Med* 173:721 (1991).
Linsley et al., "CTLA-4 Is a Seond Receptor for the B Cell Activation Antigen B7," *J. Exp. Med.* 174:561 (1991).
Louis et al., "Design and Properties of $N_{CCG}$-gp41, a Chimeric gp41 Molecule with Nanomolar HIV Fusion Inhibitory Activity," *J. Biol. Chem.* 276:(31)29485 (2001).
Peppel et al., "A Tumor Necrosis Factor (TNF) Receptor-IgG Heavy Chain Chimeric Protein as a Bivalent Antagonist of TNF Activity," *J. Exp. Med.* 174:1483 (1991).
Ridgeway and Gorman, "Expression and Activity of IgE Receptor Alpha Chain-IgG Chimeric Molecules," *J. Cell. Biol* 115, Abstract No. 1448 (1991).
Root et al., "Protein Design of an HIV-1 Entry Inhibitor," *Science* 291:884 (2001).
Stamenkovic et al., "The B Lymphocyte Adhesion Molecule CD22 Interacts with Leukocyte Common Antigen CD45RO on T Cells and α2-6 Sialytransferase, CD75, on B Cells," *Cell* 66:1133 (1991).
Traunecker et al., "Highly efficient neutralization of HIV with recombinant CD4-immunoglobulin molecules," *Nature* 339:68 (1989).
Watson et al., "A Homing Receptor-IgG Chimera as a Probe for Adhesive Ligands of Lymph Node High Endothelial Venules," *J. Cell. Biol.* 110:2221 (1990).
Watson et al., "Neutrophil influx into an inflammatory site inhibited by a soluble homing receptor-IgG chimaera," *Nature* 349:164 (1991).
Zettmeissl et al., "Expression and Characterization of Human CD4: Immunoglobulin Fusion Proteins," *DNA Cell Biol. USA* 9:347 (1990).
Zheng et al., "Administration of Noncytolytic IL-10/Fc in Murine Models of Lipopolysaccharide-Induced Septic Shock and Allogenic Islet Transplantation," *J. Immun.* 154:5590 (1995).
U.S. Appl. No. 10/841,819, Rivera et al.
U.S. Appl. No. 10/841,956, Hehir et al.
Armour et al., "Recombinant human IgG molecules lacking Fc? receptor I binding and monocyte triggering activities," *Eur. J. Immunol.*, 29:2613-2624 (1999).
Bahlmann, Ferdinand H. et al., "Erythropoietin: is it more than correcting anaemia?," *Nephrol. Dial. Transplant.*, 19:20-22 (2004).
Barre-Sinoussi et al., Isolation of a T-Lymphotropic Retrovirus from a Patient at Risk for Acquired Immune Deficiency Syndrome (AIDS), Science 220:868 (1983).
Broze et al., "Purification and Properties of Human Coagulation Factor VII," J. Biol. Chem., 255:1242 (1980).
Burmeister et al., "Crystal structure at 2.2 A resolution of the MHC-related neonatal Fc receptor," Nature, 372:323-324 (1994).
Carter et al., "Structure of Serum Albumin," Adv. Prot. Chem. 45:153 (1994).
Chan et al., HIV Entry and Its Inhibition, Cell 93:681 (1998).
Clerc et al., "Primary structure control of recombinant proteins using high-performance liquid chromatography, mass spectrometry and microsequencing," J. Chromatography 662:245 (1994).
Cohen et al., "Acquired inhibitors," Bailiere's Clinical Hematology, 9(2):331 (1996).
International Search Report for PCT/US06/000140 dated Jun. 2, 2006.
Dagleish et al., The CD4 (T4) antigen is an essential component of the receptor for the AIDS retrovirus, Nature 312:763 (1984).
Davis et al., Preparation and characterization of antibodies with specificity for the amino-terminal tetrapeptide sequence of the platelet-derived connective tissue activating peptide-III, Biochem. Intl. 10(3):394 (1985).
De Clerq et al., New Anti-HIV Agents and Targets, Med. Res. Rev. 22(6):531 (2002).

Dugaiczyk et al., "Nucleotide sequence and the encoded amino acids of human serum albumin mRNA," Proc. Nat. Acad. Sci. USA 79:71 (1982).

Erickson et al., Solid-phase peptide synthesis, The Proteins (3d ed.) 3:257 (1976).

Finn et al., The synthesis of peptides by solution methods with emphasis on peptide hormones, The Proteins (3d ed.) 2:105 (1976).

Fischer et al., "The effects of postponing prophylactic treatment on long-term outcome in patients with severe hemophilia," Blood, 99(7):2337 (2002).

Friend et al., "Phase I study of an engineered aglycosylated humanized CD3 antibody in renal transplant rejection," Transplantation, 68:1632-1637 (1999).

Frostell-Karlsson et al., "Biosensor analysis of the interaction between immobilized human serum albumin and drug compounds for prediction of human serum albumin binding levels," J. Med. Chem. 43:1986 (2000).

Gallo et al., Frequent Detection and Isolation of Cytopathic Retroviruses (HTLV-III) from Patents with AIDS and at Risk for AIDS, Science 224:500 (1984).

Geoghegan et al., Side-directed conjugation of nonpeptide groups to peptides and proteins via periodate oxidation of a 2-amino alcohol. Application to modification at N-terminal serine, Bioconjugate Chem. 3:138 (1992).

Hage et al., "Recent advances in chromatographic and electrophoretic methods for the study of drug-protein interactions," J. Chromatography 699:499 (1997).

Hagen et al., "Characterization of a cDNA coding for human factor VII," Proc. Natl. Acad. Sci. USA, 83:2412 (1986).

Hammarskjold et al., The molecular biology of the human immunodeficiency virus, Biochem. Biophys. Acta 989:269 (1989).

Israel et al., "Expression of the neonatal Fc receptor, FcRn, on human intestinal epithelial cells," Immunol., 92:69-74 (1997).

Johannessen et al., "Comparison of the factor VII:C clot analysis and a modified activated factor VII analysis for monitoring factor VII activity in patients treated with recombinant activated factor VII (NovoSeven®)," Blood Coagulation and Fibrinolysis, 11(Suppl. 1):S159 (2000).

Jones et al., "Replacing the complementarity-determining regions in a human antibody with those from a mouse ," Nature, 321:522-525 (1986).

Kang et al., "Linkage of recognition and replication functions by assembling combinatorial antibody Fab libraries along phage surfaces," Proc. Natl. Acad. Sci. USA, 88:4363-4366 (1991).

Kasper, "Hereditary plasma clotting factor disorders and their management," Haemophilia, 6(Suppl. 1):13, (2000).

Kilby et al., Potent suppression of HIV-1 replication in humans by T-20, a peptide inhibitor of gp41-mediated virus entry, Nat. Med. 4(11):1302 (1998).

Kobayashi et al., "FcRn-mediated transcytosis of immunoglobulin G in human renal proximal tubular epithelial cells," Am. J. Physiol. Renal Physiol., 282:F358-F365 (2002).

Lemaitre et al., "Specific antiviral activity of a poly(L-lysine)-conjugated oligodeoxyribonucleotide sequence complementary to vesicular stomatitis virus N protein mRNA initiation site," Proc. Natl. Acad. Sci. USA, 84:648-652 (1987).

Letsinger et al., "Cholesteryl-conjugated oligonucleotides: synthesis, properties, and activity as inhibitors of replication of human immunodeficiency virus in cell culture," Proc. Natl. Acad. Sci. USA, 86:6553-6536 (1989).

Maddon et al., The T4 Gene Encodes the AIDS Virus Receptor and Is Expressed in the Immune System and the Brain, Cell 47:333 (1986).

Maeda et al., Effective renaturation of denatured and reduced immunoglobulin G in vitro without assistance of chaperone, Protein Eng. 9(1):95 (1996).

Mark et al., "By-passing immunization: Building high affinity antibodies by chain shuffling," Bio/Technol., 10:779-783 (1992).

Masui et al., "Cytotoxicity against human tumor cells mediated by the conjugate of anti-epidermal growth factor receptor monoclonal antibody to recombinant ricin A chain," Cancer Res 49:3482-88 (1989).

McCafferty et al., "Phage antibodies: filamentous phage displaying antibody variable domains," Nature, 348:552-554 (1990).

McPherson et al., Synthesis of an RNA-peptide conjugate by orthogonal ligation, Synlett. S1:978 (1999).

Merrifield, Solid phase peptide synthesis, II The Synthesis of a Tetrapeptide, J. Am. Chem. Soc. 85:2149 (1963).

Merrifield, Solid-phase peptide synthesis, The Chemistry of Polypeptides, Katsoyannis, pp. 335-361 (1973).

Muir et al., Expressed protein ligation: A general method for protein engineering, Proc. Natl. Acad. Sci. USA, 95:6705 (1998).

Nilsson, "The Management of Hemophilia Patients With Inhibitors," Transfusion Medicine Review, 6(4):285 (1992).

Nussbaum et al., Fusogenic Mechanisms of Enveloped-Virus Glycoproteins Analyzed by a Novel Recombinant Vaccinia Virus-Based Assay Quantitating Cell Fusion-Dependent Reporter Gene Activation, J. Virol. 68(9):5411 (1994).

Oravcova et al., "Drug-protein binding studies new trends in analytical and experimental methodology," J. Chromatography 677:1 (1996).

Pederson et al., "Autoactivation of Human Recombinant Coagulation Factor VII," Biochemistry, 28:9331 (1989).

Petrini, "What factors should influence the dosage and interval of prophylactic treatment in patients with severe haemophilia A and B?" Hsemophilia, 7:99 (2001).

Rahimipour et al., "Design, synthesis, and evaluation of a long-acting, potent analogue of gonadotropin-releasing hormone," J. Med. Chem. 44:3645 (2001).

Routledge et al., "The effct of aglycosylation on the immunogenicity of a humanized therapeutic CD3 monoclonal antibody," Transplantation, 60:847-853 (1995).

Sarin et al., Inhibition of acquired immunodeficiency syndrome virus by oligodeoxynucleoside methylphosphonates, Proc. Natl. Acad. Sci. USA 85:7448 (1988).

Sarver et al., "Ribozymes as potential anti-HIV-1 therapeutic agents," Science, 247:1222-1225 (1990).

Seelig et al., "Synthetic mimics of juxtaposed amino- and carboxyl-terminal peptide domains of human gamma interferon block ligand binding to human gamma interferon receptor," J Biol Chem 1:358-63 (1994).

Severinov et al., "Expressed Protein Ligation, a Novel Method for Studying Protein-Protein Interactions in Transcription," J Biol Chem 273:16205-09 (1998).

Shields et al., "High resolution mapping of the binding site on human IgG1 for Fc gamma RI, FcgammaRII, FcgammaRIII, and FcRn and design of IgG1 variants with improved binding to the FcgammaR," J. Biol. Chem., 276(9):6591-6604 (2001).

Solulink Biosciences Bioconjugation, Immobilization & Detection Reagents, Kits and Services Catalog (p. 4), 2005, retrieved Dec. 22, 2005, from http://www.solulink.com/solulink_catalog.pdf.

Stein et al., Physiocochemical properties of phosphorothioate oligodeoxynucleotides, Nucl. Acids Res. 16(8):3209 (1988).

Stetsenko et al., Efficient Conjugation of Peptides to Oligonucleotides by 'Native Ligation', Journal of Organic Chemistry, 65:4900-4908 (2000).

Story et al., "A major histocompatibility complex class I-like Fc receptor cloned from human placenta: possible role in transfer of immunoglobulin G from mother to fetus," J. Exp. Med., 180(6):2377-2381 (1994).

Ueda et al., Favourable interaction between heavy and light chains arrests the undesirable oligomerization of heavy chains in the refolding of denatured and reduced immunoglobulin G, Cell Mol. Life Sci. 53:929 (1997).

van der Krol et al., "Modulation of eukaryotic gene expression by complementary RNA or DNA sequences," Bio Techniques, 6(10):958-976 (1988).

van der Meer, et al., "Erythropoietin in cardiovascular diseases," Eur. Heart J., 25:285-291 (2004).

Van der Meer, P., et al., "Erythropoietin improves left ventricular function and coronary flow in an experimental model of ischemia-reperfusion injury," Eur. J. Heart Fail., 6(7):853-859 (2004).

Waldmann, T.A., "Albumin Catabolism," Albumin Structure, Function and Uses, Pergamon Press, Princeton, NJ (1977).

Ward et al., "The effector functions of immunoglobulins: implications for therapy," Ther. Immunol., 2(2):77-94 (1995).

Waterhouse et al., "Combinatorial infection and in vivo recombination: a strategy for making large phage antibody repertoires," Nucl. Acid Res., 21:2265-2266 (1993).

Wild et al., A synthetic peptide inhibitor of human immunodeficiency virus replication: Correlation between solution structure and viral inhibition, Proc. Natl. Acad. Sci USA 89:10537 (1992).

Wild et al., Peptides corresponding to a predictive alpha-helical domain of human immunodeficiency virus type 1 gp41 are potent inhibitors of virus infection, Proc. Natl. Acad. Sci USA 91: 9770 (1994).

Zatsepin et al., Synthesis of peptide-oligonucleotide conjugates with single and multiple peptides attached to 2'-aldehydes through thiazolidine, oxime, and hydrazine linkages, Bioconjugate Chem., 13:822 (2002).

Zhang et al., Preparation of functionally active cell-permeable peptides by single-step ligation of two peptide molecules, Proc. Nat. Acad. Sci. USA, 95:9184 (1998).

Zon, "Oligonucleotide analogues as potential chemotherapeutic agents," Pharm. Res., 5:539-549 (1988).

Glennie, M.J. et al., "Univalent Antibodies Kill Tumor Cells In-Vitro and In-Vivo." *Nature*, 295:712-714 (1982).

Ketas, Thomas J. et al., Human Immunodeficiency Virus Type 1 Attachment, Coreceptor, and Fusion Inhibitors Are Active Against Both Direct and Trans Infection of Primary Cells. *Journal of Virology*, 77:2762-2767 (2003).

Stevenson, G.T. et al., "Chimeric Univalent Antibodies For Treating Lymphoid Malignancies." *Medical Oncology and Tumor Pharmacotherapy*, 1:275-278 (1984).

Supplementary European Search Report, European Patent Office, App. No. EP 04 77 5946, Dec. 1, 2006.

Xu, Danzhu et al., "Mimetic Ligand-Based Affinity Purification of Immune Complexes and Immunoconjugates." *Journal of Chromatography B*, 706:217-229 (1998).

Office Action dated Jul. 27, 2007, U.S. Appl. No. 10/841,819, filed May 6, 2004.

US 6,020,459, 02/2000, Barney et al. (withdrawn)

\* cited by examiner

FACTOR VII-Fc AMINO ACID SEQUENCE (SIGNAL PEPTIDE UNDERLINED, PROPEPTIDE IN BOLD)

```
  1 MVSQALRLLC LLLGLQGCLA AVFVTQEEAH GVLHRRRRAN AFLEELRPGS
 51 LERECKEEQC SFEEAREIFK DAERTKLFWI SYSDGDQCAS SPCQNGGSCK
101 DQLQSYICFC LPAFEGRNCE THKDDQLICV NENGGCEQYC SDHTGTKRSC
151 RCHEGYSLLA DGVSCTPTVE YPCGKIPILE KRNASKPQGR IVGGKVCPKG
201 ECPWQVLLLV NGAQLCGGTL INTIWVVSAA HCFDKIKNWR NLIAVLGEHD
251 LSEHDGDEQS RRVAQVIIPS TYVPGTTNHD IALLRLHQPV VLTDHVVPLC
301 LPERTFSERT LAFVRFSLVS GWGQLLDRGA TALELMVLNV PRLMTQDCLQ
351 QSRKVGDSPN ITEYMFCAGY SDGSKDSCKG DSGGPHATHY RGTWYLTGIV
401 SWGQGCATVG HFGVYTRVSQ YIEWLQKLMR SEPRPGVLLR APFPDKTHTC
451 PPCPAPELLG GPSVFLFPPK PKDTLMISRT PEVTCVVVDV SHEDPEVKFN
501 WYVDGVEVHN AKTKPREEQY NSTYRVVSVL TVLHQDWLNG KEYKCKVSNK
551 ALPAPIEKTI SKAKGQPREP QVYTLPPSRD ELTKNQVSLT CLVKGFYPSD
601 IAVEWESNGQ PENNYKTTPP VLDSDGSFFL YSKLTVDKSR WQQGNVFSCS
651 VMHEALHNHY TQKSLSLSPG K
```

FIG. 2A

FACTOR IX-Fc AMINO ACID SEQUENCE (SIGNAL PEPTIDE UNDERLINED, PROPEPTIDE IN BOLD)

```
  1 MQRVNMIMAE SPGLITICLL GYLLSAECTV FLDHENANKI LNRPKRYNSG
 51 KLEEFVQGNL ERECMEEKCS FEEAREVFEN TERTTEFWKQ YVDGDQCESN
101 PCLNGGSCKD DINSYECWCP FGFEGKNCEL DVTCNIKNGR CEQFCKNSAD
151 NKVVCSCTEG YRLAENQKSC EPAVPFCGR VSVSQTSKLT RAETVFPDVD
201 YVNSTEAETI LDNITQSTQS FNDFTRVVGG EDAKPGQFPW QVVLNGKVDA
251 FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS
351 GYVSGWGRVF HKGRSALVLQ YLRVPLVDRA TCLRSTKFTI YNNMFCAGFH
401 EGGRDSCQGD SGGPHVTEVE GTSFLTGIIS WGEECAMKGK YGIYTKVSRY
451 VNWIKEKTKL TEFAGAAAVD KTHTCPPCPA PELLGGPSVF LFPPKPKDTL
501 MISRTPEVTC VVVDVSHEDP EVKFNWYVDG VEVHNAKTKP REEQYNSTYR
551 VVSVLTVLHQ DWLNGKEYKC KVSNKALPAP IEKTISKAKG QPREPQVYTL
601 PPSRDELTKN QVSLTCLVKG FYPSDIAVEW ESNGQPENNY KTTPPVLDSD
651 GSFFLYSKLT VDKSRWQQGN VFSCSVMHEA LHNHYTQKSL SLSPGK
```

FIG. 2B

IFNα-Fc AMINO ACID SEQUENCE (8 AMINO ACID LINKER) (SIGNAL SEQUENCE UNDERLINED)

```
  1 MALTFALLVA LLVLSCKSSC SVGCDLPQTH SLGSRRTLML LAQMRRISLF
 51 SCLKDRHDFG FPQEEFGNQF QKAETIPVLH EMIQQIFNLF STKDSSAAWD
101 ETLLDKFYTE LYQQLNDLEA CVIQGVGVTE TPLMKEDSIL AVRKYFQRIT
151 LYLKEKKYSP CAWEVVRAEI MRSFSLSTNL QESLRSKEEF AGAAAVDKTH
201 TCPPCPAPEL LGGPSVFLFP PKPKDTLMIS RTPEVTCVVV DVSHEDPEVK
251 FNWYVDGVEV HNAKTKPREE QYNSTYRVVS VLTVLHQDWL NGKEYKCKVS
301 NKALPAPIEK TISKAKGQPR EPQVYTLPPS RDELTKNQVS LTCLVKGFYP
351 SDIAVEWESN GQPENNYKTT PPVLDSDGSF FLYSKLTVDK SRWQQGNVFS
401 CSVMHEALHN HYTQKSLSLS PGK
```

FIG. 2C

IFNα-Fc Δ LINKER AMINO ACID SEQUENCE (SIGNAL SEQUENCE UNDERLINED)

```
  1 MALTFALLVA LLVLSCKSSC SVGCDLPQTH SLGSRRTLML LAQMRRISLF
 51 SCLKDRHDFG FPQEEFGNQF QKAETIPVLH EMIQQIFNLF STKDSSAAWD
101 ETLLDKFYTE LYQQLNDLEA CVIQGVGVTE TPLMKEDSIL AVRKYFQRIT
151 LYLKEKKYSP CAWEVVRAEI MRSFSLSTNL QESLRSKEDK THTCPPCPAP
201 ELLGGPSVFL FPPKPKDTLM ISRTPEVTCV VVDVSHEDPE VKFNWYVDGV
251 EVHNAKTKPR EEQYNSTYRV VSVLTVLHQD WLNGKEYKCK VSNKALPAPI
301 EKTISKAKGQ PREPQVYTLP PSRDELTKNQ VSLTCLVKGF YPSDIAVEWE
351 SNGQPENNYK TTPPVLDSDG SFFLYSKLTV DKSRWQQGNV FSCSVMHEAL
401 HNHYTQKSLS LSPGK
```

FIG. 2D

FLAGFc AMINO ACID SEQUENCE (SIGNAL SEQUENCE UNDERLINED)

```
  1 METDTLLLWV LLLWVPGSTG DDYKDDDDKD KTHTCPPCPA PELLGGPSVF
 51 LFPPKPKDTL MISRTPEVTC VVVDVSHEDP EVKFNWYVDG VEVHNAKTKP
101 REEQYNSTYR VVSVLTVLHQ DWLNGKEYKC KVSNKALPAP IEKTISKAKG
151 QPREPQVYTL PPSRDELTKN QVSLTCLVKG FYPSDIAVEW ESNGQPENNY
201 KTTPPVLDSD GSFFLYSKLT VDKSRWQQGN VFSCSVMHEA LHNHYTQKSL
251 SLSPGK
```

FIG. 2E

Epo-CCA-Fc AMINO ACID SEQUENCE (K$^b$ SIGNAL SEQUENCE UNDERLINED, ACIDIC COILED COIL IN BOLD)

```
  1  MVPCTLLLLL AAALAPTQTR AGSRAPPRLI CDSRVLQRYL LEAEAENIT
 51  TGCAEHCSLN ENITVPDTKV NFYAWKRMEV GQQAVEVWQG LALLSEAVLR
101  GQALLVNSSQ PWEPLQLHVD KAVSGLRSLT TLLRALGAQK EAISPPDAAS
151  AAPLRTITAD TFRKLFRVYS NFLRGKLKLY TGEACRTGDR EFGGEYQALE
201  KEVAQLEAEN QALEKEVAQL EHEGGGPAPE LLGGPSVFLF PPKPKDTLMI
251  SRTPEVTCVV VDVSHEDPEV KFNWYVDGVE VHNAKTKPRE EQYNSTYRVV
301  SVLTVLHQDW LNGKEYKCKV SNKALPAPIE KTISKAKGQP REPQVYTLPP
351  SRDELTKNQV SLTCLVKGFY PSDIAVEWES NGQPENNYKT TPPVLDSDGS
401  FFLYSKLTVD KSRWQQGNVF SCSVMHEALH NHYTQKSLSL SPGK
```

FIG. 2F

CCB-Fc AMINO ACID SEQUENCE (K$^b$ SIGNAL SEQUENCE UNDERLINED, BASIC COILED COIL IN BOLD)

```
  1  MVPCTLLLLL AAALAPTQTR AGEFGGEYQA LKKKVAQLKA KNQALKKKVA
 51  QLKHKGGGPA PELLGGPSVF LFPPKPKDTL MISRTPEVTC VVVDVSHEDP
101  EVKFNWYVDG VEVHNAKTKP REEQYNSTYR VVSVLTVLHQ DWLNGKEYKC
151  KVSNKALPAP IEKTISKAKG QPREPQVYTL PPSRDELTKN QVSLTCLVKG
201  FYPSDIAVEW ESNGQPENNY KTTPPVLDSD GSFFLYSKLT VDKSRWQQGN
251  VFSCSVMHEA LHNHYTQKSL SLSPGK
```

FIG. 2G

CysFc AMINO ACID SEQUENCE (hIFNa SIGNAL SEQUENCE UNDERLINED)

```
  1  MALTFALLVA LLVLSCKSSC SVGCPPCPAP ELLGGPSVFL FPPKPKDTLM
 51  ISRTPEVTCV VVDVSHEDPE VKFNWYVDGV EVHNAKTKPR EEQYNSTYRV
101  VSVLTVLHQD WLNGKEYKCK VSNKALPAPI EKTISKAKGQ PREPQVYTLP
151  PSRDELTKNQ VSLTCLVKGF YPSDIAVEWE SNGQPENNYK TTPPVLDSDG
201  SFFLYSKLTV DKSRWQQGNV FSCSVMHEAL HNHYTQKSLS LSPGK
```

FIG. 2H

IFNα GS15 Fc PROTEIN SEQUENCE (SIGNAL SEQUENCE UNDERLINED):

```
  1  MALTFALLVA LLVLSCKSSC SVGCDLPQTH SLGSRRTLML LAQMRRISLF
 51  SCLKDRHDFG FPQEEFGNQF QKAETIPVLH EMIQQIFNLF STKDSSAAWD
101  ETLLDKFYTE LYQQLNDLEA CVIQGVGVTE TPLMKEDSIL AVRKYFQRIT
151  LYLKEKKYSP CAWEVVRAEI MRSFSLSTNL QESLRSKEGG GGSGGGGSGG
201  GGSDKTHTCP PCPAPELLGG PSVFLFPPKP KDTLMISRTP EVTCVVVDVS
251  HEDPEVKFNW YVDGVEVHNA KTKPREEQYN STYRVVSVLT VLHQDWLNGK
301  EYKCKVSNKA LPAPIEKTIS KAKGQPREPQ VYTLPPSRDE LTKNQVSLTC
351  LVKGFYPSDI AVEWESNGQP ENNYKTTPPV LDSDGSFFLY SKLTVDKSRW
401  QQGNVFSCSV MHEALHNHYT QKSLSLSPGK
```

FIG. 2I

EpoFc AMINO ACID SEQUENCE (SIGNAL SEQUENCE UNDERLINED, LINKER IN BOLD)

```
  1  MGVHECPAWL WLLLSLLSLP LGLPVLGAPP RLICDSRVLE RYLLEAKEAE
 51  NITTGCAEHC SLNENITVPD TKVNFYAWKR MEVGQQAVEV WQGLALLSEA
101  VLRGQALLVN SSQPWEPLQL HVDKAVSGLR SLTTLLRALG AQKEAISPPD
151  AASAAPLRTI TADTFRKLFR VYSNFLRGKL KLYTGEACRT GDREFAGAAA
201  VDKTHTCPPC PAPELLGGPS VFLFPPKPKD TLMISRTPEV TCVVVDVSHE
251  DPEVKFNWYV DGVEVHNAKT KPREEQYNST YRVVSVLTVL HQDWLNGKEY
301  KCKVSNKALP APIEKTISKA KGQPREPQVY TLPPSRDELT KNQVSLTCLV
351  KGFYPSDIAV EWESNGQPEN NYKTTPPVLD SDGSFFLYSK LTVDKSRWQQ
401  GNVFSCSVMH EALHNHYTQK SLSLSPGK
```

FIG. 2J

FACTOR VII-FC NUCLEOTIDE SEQUENCE (SIGNAL PEPTIDE UNDERLINED, PROPPEPTIDE IN BOLD)

<u>atggtctcccaggccctcaggctcctctgccttctgcttgggcttcagggctgcctggctgcag</u>
tcttcgtaacccaggaggaagcccacggcgtcctgcaccggcgccggcgcgccaacgcgttcct
ggaggagctgcggccgggctccctggagagggagtgcaaggaggagcagtgctccttcgaggag
gcccgggagatcttcaaggacgcggagaggacgaagctgttctggatttcttacagtgatgggg
accagtgtgcctcaagtccatgccagaatgggggctcctgcaaggaccagctccagtcctatat
ctgcttctgcctccctgccttcgagggccggaactgtgagacgcacaaggatgaccagctgatc
tgtgtgaacgagaacggcggctgtgagcagtactgcagtgaccacacgggcaccaagcgctcct
gtcggtgccacgaggggtactctctgctggcagacggggtgtcctgcacacccacagttgaata
tccatgtggaaaaatacctattctagaaaaaagaaatgccagcaaaccccaaggccgaattgtg
gggggcaaggtgtgccccaaaggggagtgtccatggcaggtcctgttgttggtgaatggagctc
agttgtgtgggggggaccctgatcaacaccatctgggtggtctccgcggcccactgtttcgacaa
aatcaagaactggaggaacctgatcgcggtgctgggcgagcacgacctcagcgagcacgacggg
gatgagcagagccggcgggtggcgcaggtcatcatccccagcacgtacgtcccgggcaccacca
accacgacatcgcgctgctccgcctgcaccagcccgtggtcctcactgaccatgtggtgcccct
ctgcctgcccgaacggacgttctctgagaggacgctggccttcgtgcgcttctcattggtcagc
ggctggggccagctgctggaccgtggcgccacggccctggagctcatggtcctcaacgtgcccc
ggctgatgacccaggactgcctgcagcagtcacggaaggtgggagactccccaaatatcacgga
gtacatgttctgtgccggctactcggatggcagcaaggactcctgcaagggggcacgtggaggc
ccacatgccacccactaccggggcacgtggtacctgacgggcatcgtcagctggggccagggct
gcgcaaccgtgggccactttggggtgtacaccagggtctcccagtacatcgagtggctgcaaaa
gctcatgcgctcagagccacgcccaggagtcctcctgcgagcccccatttcccgacaaaactcac
acgtgcccgccgtgcccagctccggaactgctgggcggaccgtcagtcttcctcttcccccaa
aacccaaggacacccctcatgatctcccggacccctgaggtcacatgcgtggtggtggacgtgag
ccacgaagaccctgaggtcaagttcaactggtacgtggacggcgtggaggtgcataatgccaag
acaaagccgcgggaggagcagtacaacagcacgtaccgtgtggtcagcgtcctcaccgtcctgc
accaggactggctgaatggcaaggagtacaagtgcaaggtctccaacaaagccctcccagcccc
catcgagaaaaccatctccaaagccaaagggcagccccgagaaccacaggtgtacaccctgccc
ccatcccgggatgagctgaccaagaaccaggtcagcctgacctgcctggtcaaaggcttctatc
ccagcgacatcgccgtggagtgggagagcaatgggcagccggagaacaactacaagaccacgcc
tcccgtgttggactccgacggctccttcttcctctacagcaagctcaccgtggacaagagcagg
tggcagcaggggaacgtcttctcatgctccgtgatgcatgaggctctgcacaaccactacacgc
agaagagcctctccctgtctccgggtaaatga

FIG. 3A

FACTOR IX-FC NUCLEOTIDE SEQUENCE (SIGNAL PEPTIDE UNDERLINED, PROPPEPTIDE IN BOLD)

<u>atgcagcgcgtgaacatgatcatggcagaatcaccaggcctcatcaccatctgccttttaggat</u>
<u>atctactcagtgctgaa</u>tgtcacgttttcttgatcatgaaaacgccaacaaaattctgaatcg
gccaaagagggtataattcaggtaaattggaagagtttgttcaagggaaccttgagagagaatgt
atggaagaaagtgtagttttgaagaagcacgagaagttttgaaaacactgaaagaacaactg
aattttggaagcagtatgttgatggagatcagtgtgagtccaatccatgtttaaatggcggcag
ttgcaaggatgacattaattcctatgaatgttggtgtccctttggatttgaaggaaagaactgt
gaattagatgtaacatgtaacattaagaatggcagatgcgagcagttttgtaaaaatagtgctg
ataacaaggtggtttgctcctgtactgagggatatcgacttgcagaaaaccagaagtcctgtga
accagcagtgccatttccatgtggaagagtttctgtttcacaaacttctaagctcacccgtgct
gagactgttttcctgatgtggactatgtaaattctactgaagctgaaaccatttggataaca
tcactcaagcacccaatcatttaatgacttcactcgggttgttggtggagaagatgccaaacc
aggtcaattcccttggcaggttgttttgaatggtaaagttgatgcattctgtggaggctctatc
gttaatgaaaaatggattgtaactgctgcccactgtgttgaaactggtgttaaaattacagttg
tcgcaggtgaacataatattgaggagacagaacatacagagcaaaagcgaaatgtgattcgaat
tattcctcaccacaactacaatgcagctattaataagtacaaccatgacattgcccttctggaa
ctggacgaacccttagtgctaaacagctacgttacacctatttgcattgctgacaaggaataca
cgaacatcttcctcaaatttggatctggctatgtaagtggctggggaagagtcttccacaaagg
gagatcagctttagttcttcagtaccttagagttccacttgtgaccgagccacatgtcttcga
tctacaaagttcaccatctataacaacatgttctgtgctggcttccatgaaggaggtagagatt
catgtcaaggagatagtggggggaccccatgttactgaagtggaagggaccagtttcttaactgg
aattattagctggggtgaagagtgtgcaatgaaaggcaaatatggaatatataccaaggtatcc
cggtatgtcaactggattaaggaaaaaacaaagctcactgaattcgccggcgccgctgcggtcg
acaaaactcacacgtgcccgccgtgcccagctccggaactgctgggcggaccgtcagtcttcct
cttccccccaaaacccaaggacaccctcatgatctcccggacccctgaggtcacatgcgtggtg
gtggacgtgagccacgaagaccctgaggtcaagttcaactggtacgtggacggcgtggaggtgc
ataatgccaagacaaagccgcggggaggagcagtacaacagcacgtaccgtgtggtcagcgtcct
caccgtcctgcaccaggactggctgaatggcaaggagtacaagtgcaaggtctccaacaaagcc
ctcccagcccccatcgagaaaaccatctccaaagccaaagggcagccccgagaaccacaggtgt
acaccctgcccccatcccgggatgagctgaccaagaaccaggtcagcctgacctgcctggtcaa
aggcttctatcccagcgacatcgccgtggagtgggagagcaatgggcagccggagaacaactac
aagaccacgcctcccgtgttggactccgacggctccttcttcctctacagcaagctcaccgtgg
acaagagcaggtggcagcaggggaacgtcttctcatgctccgtgatgcatgaggctctgcacaa
ccactacacgcagaagagcctctccctgtctccgggtaaatga

FIG. 3B

IFNα-Fc NUCLEOTIDE SEQUENCE (8 AMINO ACID LINKER)

<u>atggccttgacctttgctttactggtggccctcctggtgctcagctgcaagtcaagctgctctg
tgggc</u>tgtgatctgcctcaaacccacagcctgggtagcaggaggaccttgatgctcctggcaca
gatgaggagaatctctcttttctcctgcttgaaggacagacatgactttggatttccccaggag
gagtttggcaaccagttccaaaaggctgaaaccatccctgtcctccatgagatgatccagcaga
tcttcaatctcttcagcacaaaggactcatctgctgcttgggatgagaccctcctagacaaatt
ctacactgaactctaccagcagctgaatgacctggaagcctgtgtgatacagggggtggggtg
acagagactcccctgatgaaggaggactccattctggctgtgaggaaatacttccaaagaatca
ctctctatctgaaagagaagaaatacagcccttgtgcctgggaggttgtcagagcagaaatcat
gagatctttttctttgtcaacaaacttgcaagaaagtttaagaagtaaggaagaattcgccggc
gccgctgcggtcgacaaaactcacacatgcccaccgtgcccagcacctgaactcctggggggac
cgtcagtcttcctcttccccccaaaacccaaggacaccctcatgatctcccggacccctgaggt
cacatgcgtggtggtggacgtgagccacgaagaccctgaggtcaagttcaactggtacgtggac
ggcgtggaggtgcataatgccaagacaaagccgcgggaggagcagtacaacagcacgtaccgtc
tggtcagcgtcctcaccgtcctgcaccaggactggctgaatggcaaggagtacaagtgcaaggt
ctccaacaaagccctcccagcccccatcgagaaaaccatctccaaagccaaagggcagccccga
gaaccacaggtgtacaccctgcccccatcccgggatgagctgaccaagaaccaggtcagcctga
cctgcctggtcaaaggcttctatcccagcgacatcgccgtggagtgggagagcaatgggcagcc
ggagaacaactacaagaccacgcctcccgtgttggactccgacggctccttcttcctctacagc
aagctcaccgtggacaagagcaggtggcagcaggggaacgtcttctcatgctccgtgatgcatg
aggctctgcacaaccactacacgcagaagagcctctccctgtctccgggtaaatga

FIG. 3C

IFNα-Fc Δ LINKER NUCLEOTIDE SEQUENCE

<u>atggccttgacctttgctttactggtggccctcctggtgctcagctgcaagtcaagctgctctg</u>
<u>tgggc</u>tgtgatctgcctcaaacccacagcctggggtagcaggaggaccttgatgctcctggcaca
gatgaggagaatctctcttttctcctgcttgaaggacagacatgactttggatttccccaggag
gagtttggcaaccagttccaaaaggctgaaaccatccctgtcctccatgagatgatccagcaga
tcttcaatctcttcagcacaaaggactcatctgctgcttgggatgagaccctcctagacaaatt
ctacactgaactctaccagcagctgaatgacctggaagcctgtgtgatacaggggggtggggtg
acagagactcccctgatgaaggaggactccattctggctgtgaggaaatacttccaaagaatca
ctctctatctgaaagagaagaaatacagcccttgtgcctgggaggttgtcagagcagaaatcat
gagatcttttctttgtcaacaaacttgcaagaaagtttaagaagtaaggaagacaaaactcac
acgtgcccgccgtgcccagctccggaactgctgggcggaccgtcagtcttcctcttccccccaa
aacccaaggacaccctcatgatctcccggacccctgaggtcacatgcgtggtggtggacgtgag
ccacgaagaccctgaggtcaagttcaactggtacgtggacggcgtggaggtgcataatgccaag
acaaagccgcgggaggagcagtacaacagcacgtaccgtgtggtcagcgtcctcaccgtcctgc
accaggactggctgaatggcaaggagtacaagtgcaaggtctccaacaaagccctcccagcccc
catcgagaaaaccatctccaaagccaaagggcagccccgagaaccacaggtgtacaccctgccc
ccatcccgggatgagctgaccaagaaccaggtcagcctgacctgcctggtcaaaggcttctatc
ccagcgacatcgccgtggagtgggagagcaatgggcagccggagaacaactacaagaccacgcc
tcccgtgttggactccgacggctccttcttcctctacagcaagctcaccgtggacaagagcagg
tggcagcaggggaacgtcttctcatgctccgtgatgcatgaggctctgcacaaccactacacgc
agaagagcctctccctgtctccgggtaaatga

FIG. 3D

FLAGFc NUCLEOTIDE SEQUENCE

<u>atggagacagacacactcctgctatgggtactgctgctctggttccaggttccactggt</u>gacg
actacaaggacgacgatgacaaggacaaaactcacacatgcccaccgtgcccagctccggaact
cctggggggaccgtcagtcttcctcttccccccaaaacccaaggacaccctcatgatctcccgg
acccctgaggtcacatgcgtggtggtggacgtgagccacgaagaccctgaggtcaagttcaact
ggtacgtggacggcgtggaggtgcataatgccaagacaaagccgcgggaggagcagtacaacag
cacgtaccgtgtggtcagcgtcctcaccgtcctgcaccaggactggctgaatggcaaggagtac
aagtgcaaggtctccaacaaagccctcccagcccccatcgagaaaaccatctccaaagccaaag
ggcagccccgagaaccacaggtgtacaccctgcccccatcccgggatgagctgaccaagaacca
ggtcagcctgacctgcctggtcaaaggcttctatcccagcgacatcgccgtggagtgggagagc
aatgggcagccggagaacaactacaagaccacgcctcccgtgttggactccgacggctccttct
cctctacagcaagctcaccgtggacaagagcaggtggcagcaggggaacgtcttctcatgctc
cgtgatgcatgaggctctgcacaaccactacacgcagaagagcctctccctgtctccgggtaaa
tga

FIG. 3E

Epo-CCA-Fc NUCLEOTIDE SEQUENCE (K^b SIGNAL SEQUENCE UNDERLINED, ACIDIC COILED COIL IN BOLD)

<u>atggtaccgtgcacgctgctcctgctgttggcggccgccctggctccgactcagacccgcgccg</u>gctctagagcccccaccacgcctcatctgtgacagccgagtcctgcagaggtacctcttggaggccaaggaggccgagaatatcacgacgggctgtgctgaacactgcagcttgaatgagaatatcactgtcccagacaccaaagttaatttctatgcctggaagaggatggaggtcgggcagcaggccgtagaagtctggcagggcctggccctgctgtcggaagctgtcctgcggggccaggccctgttggtcaactcttcccagccgtgggagcccctgcagctgcatgtggataaagccgtcagtggccttcgcagcctcaccactctgcttcgggctctgggagcccagaaggaagccatctcccctccagatgcggcctcagctgctccactccgaacaatcactgctgacactttccgcaaactcttccgagtctactccaatttcctccggggaaagctgaagctgtacacaggggaggcctgcaggaccggtgacagggaattcggtggtgagtaccaggccctggagaaggaggtggcccagctggaggccgagaaccaggccctggagaaggaggtggcccagctggagcacgagggtggtggtcccgcacccgagctgctgggcggaccgtcagtcttcctcttccccccaaaacccaaggacaccctcatgatctcccggacccctgaggtcacatgcgtggtggtggacgtgagccacgaagaccctgaggtcaagttcaactggtacgtggacggcgtggaggtgcataatgccaagacaaagccgcgggaggagcagtacaacagcacgtaccgtgtggtcagcgtcctcaccgtcctgcaccaggactggctgaatggcaaggagtacaagtgcaaggtctccaacaaagccctcccagcccccatcgagaaaaccatctccaaagccaaagggcagccccgagaaccacaggtgtacaccctgcccccatcccgggatgagctgaccaagaaccaggtcagcctgacctgcctggtcaaaggcttctatcccagcgacatcgccgtggagtgggagagcaatgggcagccggagaacaactacaagaccacgcctcccgtgttggactccgacggctccttcttcctctacagcaagctcaccgtggacaagagcaggtggcagcaggggaacgtcttctcatgctccgtgatgcatgaggctctgcacaaccactacacgcagaagagcctctccctgtctccgggtaaatga

FIG. 3F

CCB-Fc NUCLEOTIDE SEQUENCE (SIGNAL SEQUENCE UNDERLINED, BASIC COILED COIL IN BOLD)

<u>atggtaccgtgcacgctgctcctgctgttggcggccgccctggctccgactcagacccgcgccg</u>gcgaattcggtggtgagtaccaggccctgaagaagaaggtggcccagctgaaggccaagaaccaggccctgaagaagaaggtggcccagctgaagcacaagggcggcggccccgccccagagctcctgggcggaccgtcagtcttcctcttccccccaaaacccaaggacaccctcatgatctcccggacccctgaggtcacatgcgtggtggtggacgtgagccacgaagaccctgaggtcaagttcaactggtacgtggacggcgtggaggtgcataatgccaagacaaagccgcgggaggagcagtacaacagcacgtaccgtgtggtcagcgtcctcaccgtcctgcaccaggactggctgaatggcaaggagtacaagtgcaaggtctccaacaaagccctcccagcccccatcgagaaaaccatctccaaagccaaagggcagccccgagaaccacaggtgtacaccctgcccccatcccgggatgagctgaccaagaaccaggtcagcctgacctgcctggtcaaaggcttctatcccagcgacatcgccgtggagtgggagagcaatggcagccggagaacaactacaagaccacgcctcccgtgttggactccgacggctccttcttcctctacagcaagctcaccgtggacaagagcaggtggcagcaggggaacgtcttctcatgctccgtgatgcatgaggctctgcacaaccactacacgcagaagagcctctccctgtctccgggtaaatga

FIG. 3G

CysFc NUCLEOTIDE SEQUENCE (hIFNα SIGNAL SEQUENCE UNDERLINED)

<u>atggccttgacctttgctttactggtggccctcctggtgctcagctgcaagtcaagctgctctg
tgggctg</u>cccgccgtgcccagctccggaactgctgggcggaccgtcagtcttcctcttcccccc
aaaacccaaggacaccctcatgatctcccggacccctgaggtcacatgcgtggtggtggacgtg
agccacgaagaccctgaggtcaagttcaactggtacgtggacggcgtggaggtgcataatgcca
agacaaagccgcgggaggagcagtacaacagcacgtaccgtgtggtcagcgtcctcaccgtcct
gcaccaggactggctgaatggcaaggagtacaagtgcaaggtctccaacaaagccctcccagcc
cccatcgagaaaaccatctccaaagccaaagggcagccccgagaaccacaggtgtacaccctgc
ccccatcccgggatgagctgaccaagaaccaggtcagcctgacctgcctggtcaaaggcttcta
tcccagcgacatcgccgtggagtgggagagcaatgggcagccggagaacaactacaagaccacg
cctcccgtgttggactccgacggctccttcttcctctacagcaagctcaccgtggacaagagca
ggtggcagcaggggaacgtcttctcatgctccgtgatgcatgaggctctgcacaaccactacac
gcagaagagcctctccctgtctccgggtaaatga

FIG. 3H

IFNα GS15 Fc NUCLEOTIDE SEQUENCE (SIGNAL SEQUENCE UNDERLINED):

<u>atggccttgacctttgctttactggtggccctcctggtgctcagctgcaagtcaagctgctctg
tgggct</u>gtgatctgcctcaaacccacagcctgggtagcaggaggaccttgatgctcctggcaca
gatgaggagaatctctcttttctcctgcttgaaggacagacatgactttggatttccccaggag
gagtttggcaaccagttccaaaaggctgaaaccatccctgtcctccatgagatgatccagcaga
tcttcaatctcttcagcacaaaggactcatctgctgcttgggatgagaccctcctagacaaatt
ctacactgaactctaccagcagctgaatgacctggaggcctgtgtgatacaggggggtgggggtg
acagagactcccctgatgaaggaggactccattctggctgtgaggaaatacttccaaagaatca
ctctctatctgaaagagaagaaatacagcccttgtgcctgggaggttgtcagagcagaaatcat
gagatctttttctttgtcaacaaacttgcaagaaagtttacgtagtaaggaaggtggcggcgga
tccggtggaggcgggtccggcggtggagggagcgacaaaactcacacgtgcccgccgtgcccag
ctccggaactgctgggcggaccgtcagtcttcctcttccccccaaaacccaaggacaccctcat
gatctcccggacccctgaggtcacatgcgtggtggtggacgtgagccacgaagaccctgaggtc
aagttcaactggtacgtggacggcgtggaggtgcataatgccaagacaaagccgcgggaggagc
agtacaacagcacgtaccgtgtggtcagcgtcctcaccgtcctgcaccaggactggctgaatgg
caaggagtacaagtgcaaggtctccaacaaagccctcccagcccccatcgagaaaaccatctcc
aaagccaaagggcagccccgagaaccacaggtgtacaccctgcccccatcccgggatgagctga
ccaagaaccaggtcagcctgacctgcctggtcaaaggcttctatcccagcgacatcgccgtgga
gtgggagagcaatgggcagccggagaacaactacaagaccacgcctcccgtgttggactccgac
ggctccttcttcctctacagcaagctcaccgtggacaagagcaggtggcagcaggggaacgtct
tctcatgctccgtgatgcatgaggctctgcacaaccactacacgcagaagagcctctccctgtc
tccgggtaaatga

FIG. 3I

EpoFc NUCLEOTIDE SEQUENCE (SIGNAL SEQUENCE UNDERLINED, LINKER IN BOLD)

<u>atgggagtgcacgaatgtcctgcctggctgtggcttctcctgtccctgctgtcgctccctctgg
gcctcccagtcctgggc</u>gccccaccacgcctcatctgtgacagccgagtcctggagaggtacct
cttggaggccaaggaggccgagaatatcacgacgggctgtgctgaacactgcagcttgaatgag
aatatcactgtcccagacaccaaagttaatttctatgcctggaagaggatggaggtcggggcagc
aggccgtagaagtctggcagggcctggccctgctgtcggaagctgtcctgcggggccaggccct
gttggtcaactcttcccagccgtgggagcccctgcagctgcatgtggataaagccgtcagtggc
cttcgcagcctcaccactctgcttcgggctctgggagcccagaaggaagccatctcccctccag
atgcggcctcagctgctccactccgaacaatcactgctgacactttccgcaaactcttccgagt
ctactccaatttcctccggggaaagctgaagctgtacacaggggaggcctgcagaacaggggac
agagagttcgccggcgccgctgcggtcgacaaaactcacacatgcccaccgtgcccagctccgg
aactcctgggcggaccgtcagtcttcctcttccccccaaaacccaaggacaccctcatgatctc
ccggacccctgaggtcacatgcgtggtggtggacgtgagccacgaagaccctgaggtcaagttc
aactggtacgtggacggcgtggaggtgcataatgccaagacaaagccgcgggaggagcagtaca
acagcacgtaccgtgtggtcagcgtcctcaccgtcctgcaccaggactggctgaatggcaagga
gtacaagtgcaaggtctccaacaaagccctcccagcccccatcgagaaaaccatctccaaagcc
aaagggcagccccgagaaccacaggtgtacaccctgcccccatcccgggatgagctgaccaaga
accaggtcagcctgacctgcctggtcaaaggcttctatcccagcgacatcgccgtggagtggga
gagcaatgggcagccggagaacaactacaagaccacgcctcccgtgttggactccgacggctcc
ttcttcctctacagcaagctcaccgtggacaagagcaggtggcagcaggggaacgtcttctcat
gctccgtgatgcatgaggctctgcacaaccactacacgcagaagagcctctccctgtctccggg
taaatga

FIG. 3J

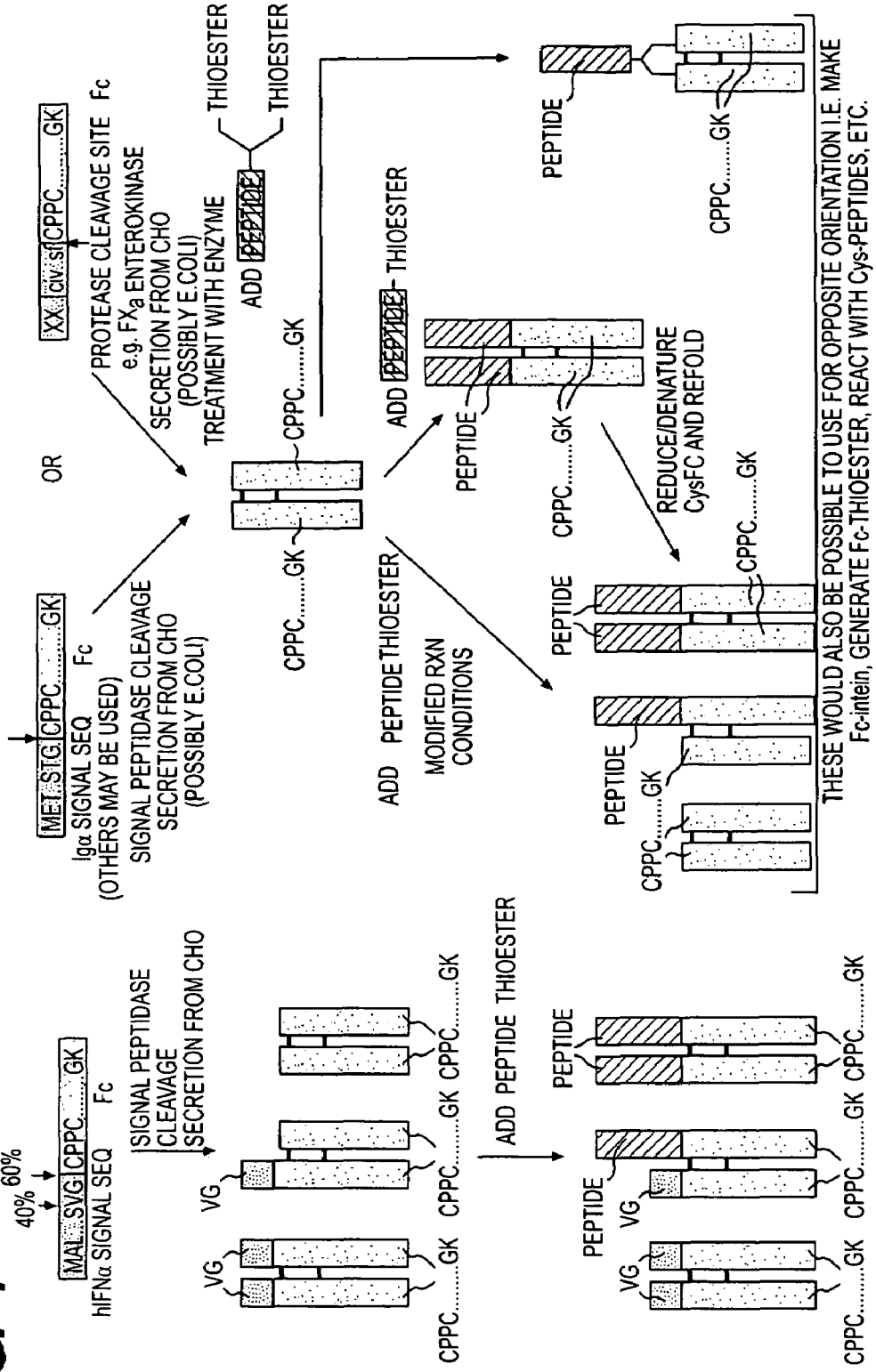

Amino acid sequence of Fc-MESNA (produced in pTWIN1 vector from NEB; when Fc-Intein-CED is eluted from chitin beads with MESNA, produces the following protein with a C-terminal thioester on the final Phe residue)

```
  1    MGIEGRGAAA VDTSHTCPPC PAPELLGGPS VFLFPPKPKD TLMISRTPEV
 51    TCVVVDVSHE DPEVKFNWYV DGVEVHNAKT KPREEQYNST YRVVSVLTVL
101    HQDWLNGKEY KCKVSNKALP APIEKTISKA KGQPREPQVY TLPPSRDELT
151    KNQVSLTCLV KGFYPSDIAV EWESNGQPEN NYKTTPPVLD SDGSFFLYSK
201    LTVDKSRWQQ GNVFSCSVMH EALHNHYTQK SLSLSPGF
```

FIG. 5A

Nucleotide sequence of Fc CDS in pTWIN1 (the final F residue, ttt, directly abuts the Mxe GyrA intein CDS in pTWIN1)

```
atgggcattgaaggcagaggcgccgctgcggtcgatactagtcacacatgcccaccgtgcccag
cacctgaactcctgggggggaccgtcagtcttcctcttccccccaaaacccaaggacacccctcat
gatctcccggaccctgaggtcacatgcgtggtggtggacgtgagccacgaagaccctgaggtc
aagttcaactggtacgtggacggcgtggaggtgcataatgccaagacaaagccgcgggaggagc
agtacaacagcacgtaccgtgtggtcagcgtcctcaccgtcctgcaccaggactggctgaatgg
caaggagtacaagtgcaaggtctccaacaaagccctcccagcccccatcgagaaaaccatctcc
aaagccaaagggcagccccgagaaccacaggtgtacaccctgcccccatcccgggatgagctga
ccaagaaccaggtcagcctgacctgcctggtcaaaggcttctatcccagcgacatcgccgtgga
gtgggagagcaatgggcagccggagaacaactacaagaccacgcctcccgtgttggactccgac
ggctccttcttcctctacagcaagctcaccgtggacaagagcaggtggcagcaggggaacgtct
tctcatgctccgtgatgcatgaggctctgcacaaccactacacgcagaagagtctctccctgtc
tccgggtttt
```

FIG. 5B

IFNβ-Fc NUCLEOTIDE SEQUENCE (SIGNAL PEPTIDE UNDERLINED)

<u>atgaccaacaagtgtctcctccaaattgctctcctgttgtgcttctccactacagctctttcca</u>
tgagctacaacttgcttggattcctacaagaagcagcaattttcagtgtcagaagctcctgtg
gcaattgaatgggaggcttgaatattgcctcaaggacaggatgaactttgacatccctgaggag
attaagcagctgcagcagttccagaaggaggacgccgcattgaccatctatgagatgctccaga
acatctttgctattttcagacaagattcatctagcactggctggaatgagactattgttgagaa
cctcctggctaatgtctatcatcagataaaccatctgaagacagtcctggaagaaaaactggag
aaagaagatttcaccaggggaaaactcatgagcagtctgcacctgaaaagatattatgggagga
ttctgcattacctgaaggccaaggagtacagtcactgtgcctggaccatagtcagagtggaaat
cctaaggaacttttacttcattaacagacttacaggttacctccgaaacgagttcgccggcgcc
gctgcggtcgacaaaactcacacatgcccaccgtgcccagctccggaactcctgggcggaccgt
cagtcttcctcttccccccaaaacccaaggacaccctcatgatctcccggacccctgaggtcac
atgcgtggtggtggacgtgagccacgaagaccctgaggtcaagttcaactggtacgtggacggc
gtggaggtgcataatgccaagacaaagccgcgggaggagcagtacaacagcacgtaccgtgtgg
tcagcgtcctcaccgtcctgcaccaggactggctgaatggcaaggagtacaagtgcaaggtctc
caacaaagccctcccagcccccatcgagaaaaccatctccaaagccaaagggcagccccgagaa
ccacaggtgtacaccctgcccccatcccgggatgagctgaccaagaaccaggtcagcctgacct
gcctggtcaaaggcttctatcccagcgacatcgccgtggagtgggagagcaatgggcagccgga
gaacaactacaagaccacgcctcccgtgttggactccgacggctccttcttcctctacagcaag
ctcaccgtggacaagagcaggtggcagcaggggaacgtcttctcatgctccgtgatgcatgagg
ctctgcacaaccactacacgcagaagagcctctccctgtctccgggtaaatga

FIG. 17A

IFNβ-Fc AMINO ACID SEQUENCE (SIGNAL SEQUENCE UNDERLINED, LINKER SEQUENCE IN BOLD, N297 IN BOLD UNDERLINED).

```
1    MTNKCLLQIA  LLLCFSTTAL  SMSYNLLGFL  QRSSNFQCQK  LLWQLNGRLE
51   YCLKDRMNFD  IPEEIKQLQQ  FQKEDAALTI  YEMLQNIFAI  FRQDSSSTGW
101  NETIVENLLA  NVYHQINHLK  TVLEEKLEKE  DFTRGKLMSS  LHLKRYYGRI
151  LHYLKAKEYS  HCAWTIVRVE  ILRNFYFINR  LTGYLRNEFA  GAAAVDKTHT
201  CPPCPAPELL  GGPSVFLFPP  KPKDTLMISR  TPEVTCVVVD  VSHEDPEVKF
251  NWYVDGVEVH  NAKTKPREEQ  YNSTYRVVSV  LTVLHQDWLN  GKEYKCKVSN
301  KALPAPIEKT  ISKAKGQPRE  PQVYTLPPSR  DELTKNQVSL  TCLVKGFYPS
351  DIAVEWESNG  QPENNYKTTP  PVLDSDGSFF  LYSKLTVDKS  RWQQGNVFSC
401  SVMHEALHNH  YTQKSLSLSP  GK
```

FIG. 17B

YTSLIHSLIEESQNQQEKNEQELLELDKWASLWNWF (SEQ ID NO: 1).

FIG. 18A

NNLRAIEAQQHLLQLTVWGIKQLQARILAVERYLKDQ (SEQ ID NO: 2)

FIG. 18B

WQEWEQKITALLEQAQIQQEKNEYELQKLDKWASLWEWF (SEQ ID NO: 3)

IMMUNOGLOBULIN CHIMERIC MONOMER-DIMER HYBRIDS

DESCRIPTION OF THE INVENTION

This application claims priority to U.S. Provisional Appln. No. 60/469,600 filed May 6, 2003, U.S. Provisional Appln. No. 60/487,964 filed Jul. 17, 2003, and U.S. Provisional Appln. No. 60/539,207 filed Jan. 26, 2004, all of which are incorporated by reference in their entirety. The U.S. nonprovisional application entitled Methods for Chemically Synthesizing Immunoglobulin Chimeric Proteins, filed concurrently on May 6, 2004, is incorporated by reference.

FIELD OF THE INVENTION

The invention relates generally to therapeutic chimeric proteins, comprised of two polypeptide chains, wherein the first chain is comprised of a therapeutic biologically active molecule and the second chain is not comprised of the therapeutic biologically active molecule of the first chain. More specifically, the invention relates to chimeric proteins, comprised of two polypeptide chains, wherein both chains are comprised of at least a portion of an immunoglobulin constant region wherein the first chain is modified to further comprise a biologically active molecule, and the second chain is not so modified. The invention, thus relates to a chimeric protein that is a monomer-dimer hybrid, i.e., a chimeric protein having a dimeric aspect and a monomeric aspect, wherein the dimeric aspect relates to the fact that it is comprised of two polypeptide chains each comprised of a portion of an immunoglobulin constant region, and wherein the monomeric aspect relates to the fact that only one of the two chains is comprised of a therapeutic biologically active molecule. FIG. 1 illustrates one example of a monomer-dimer hybrid wherein the biologically active molecule is erythropoietin (EPO) and the portion of an immunoglobulin constant region is an IgG Fc region.

BACKGROUND OF THE INVENTION

Immunoglobulins are comprised of four polypeptide chains, two heavy chains and two light chains, which associate via disulfide bonds to form tetramers. Each chain is further comprised of one variable region and one constant region. The variable regions mediate antigen recognition and binding, while the constant regions, particularly the heavy chain constant regions, mediate a variety of effector functions, e.g., complement binding and Fc receptor binding (see, e.g., U.S. Pat. Nos. 6,086,875; 5,624,821; 5,116,964).

The constant region is further comprised of domains denoted CH (constant heavy) domains (CH1, CH2, etc.). Depending on the isotype, (i.e. IgG, IgM, IgA IgD, IgE) the constant region can be comprised of three or four CH domains. Some isotypes (e.g. IgG) constant regions also contain a hinge region Janeway et al. 2001, *Immunobiology*, Garland Publishing, N.Y., N.Y.

The creation of chimeric proteins comprised of immunoglobulin constant regions linked to a protein of interest, or fragment thereof, has been described (see, e.g., U.S. Pat. Nos. 5,480,981 and 5,808,029; Gascoigne et al. 1987, *Proc. Natl. Acad. Sci. USA* 84:2936; Capon et al. 1989, *Nature* 337:525; Traunecker et al. 1989, *Nature* 339:68; Zettmeissl et al. 1990, *DNA Cell Biol. USA* 9:347; Byrn et al. 1990, *Nature* 344:667; Watson et al. 1990, *J. Cell. Biol.* 110:2221; Watson et al. 1991, *Nature* 349:164; Aruffo et al. 1990, *Cell* 61:1303; Linsley et al. 1991, *J. Exp. Med.* 173:721; Linsley et al. 1991, *J. Exp. Med.* 174:561; Stamenkovic et al., 1991, *Cell* 66:1133; Ashkenazi et al. 1991, *Proc. Natl. Acad. Sci. USA* 88:10535; Lesslauer et al. 1991, *Eur. J. Immunol.* 27:2883; Peppel et al. 1991, *J. Exp. Med.* 174:1483; Bennett et al. 1991, *J. Biol. Chem.* 266:23060; Kurschner et al. 1992, *J. Biol. Chem.* 267: 9354; Chalupny et al. 1992, *Proc. Natl. Acad. Sci. USA* 89:10360; Ridgway and Gorman, 1991, *J. Cell. Biol.* 115, Abstract No. 1448; Zheng et al. 1995, *J. Immun.* 154:5590). These molecules usually possess both the biological activity associated with the linked molecule of interest as well as the effector function, or some other desired characteristic associated with the immunoglobulin constant region (e.g. biological stability, cellular secretion).

The Fc portion of an immunoglobulin constant region, depending on the immunoglobulin isotype can include the CH2, CH3, and CH4 domains, as well as the hinge region. Chimeric proteins comprising an Fc portion of an immunoglobulin bestow several desirable properties on a chimeric protein including increased stability, increased serum half life (see Capon et al. 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1).

FcRn is active in adult epithelial tissue and expressed in the lumen of the intestines, pulmonary airways, nasal surfaces, vaginal surfaces, colon and rectal surfaces (U.S. Pat. No. 6,485,726). Chimeric proteins comprised of FcRn binding partners (e.g. IgG, Fc fragments) can be effectively shuttled across epithelial barriers by FcRn, thus providing a non-invasive means to systemically administer a desired therapeutic molecule. Additionally, chimeric proteins comprising an FcRn binding partner are endocytosed by cells expressing the FcRn. But instead of being marked for degradation, these chimeric proteins are recycled out into circulation again, thus increasing the in vivo half life of these proteins.

Portions of immunoglobulin constant regions, e.g., FcRn binding partners typically associate, via disulfide bonds and other non-specific interactions, with one another to form dimers and higher order multimers. The instant invention is based in part upon the surprising discovery that transcytosis of chimeric proteins comprised of FcRn binding partners appears to be limited by the molecular weight of the chimeric protein, with higher molecular weight species being transported less efficiently.

Chimeric proteins comprised of biologically active molecules, once administered, typically will interact with a target molecule or cell. The instant invention is further based in part upon the surprising discovery that monomer-dimer hybrids, with one biologically active molecule, but two portions of an immunoglobulin constant region, e.g., two FcRn binding partners, function and can be transported more effectively than homodimers, also referred to herein simply as "dimers" or higher order multimers with two or more copies of the biologically active molecule. This is due in part to the fact that chimeric proteins, comprised of two or more biologically active molecules, which exist as dimers and higher order multimers, can be sterically hindered from interacting with their target molecule or cell, due to the presence of the two or more biologically active molecules in close proximity to one another and that the biologically active molecule can have a high affinity for itself.

Accordingly one aspect of the invention provides chimeric proteins comprised of a biologically active molecule that is transported across the epithelium barrier. An additional aspect of the invention provides chimeric proteins comprised of at least one biologically active molecule that is able to interact with its target molecule or cell with little or no steric hindrance or self aggregation.

The aspects of the invention provide for chimeric proteins comprising a first and second polypeptide chain, the first chain comprising at least a portion of immunoglobulin constant region, wherein the portion of an immunoglobulin constant region has been modified to include a biologically active molecule and the second chain comprising at least a portion of immunoglobulin constant region, wherein the portion of an immunoglobulin constant region has not been so modified to include the biologically active molecule of the first chain.

SUMMARY OF THE INVENTION

The invention relates to a chimeric protein comprising one biologically active molecule and two molecules of at least a portion of an immunoglobulin constant region. The chimeric protein is capable of interacting with a target molecule or cell with less steric hindrance compared to a chimeric protein comprised of at least two biologically active molecules and at least a portion of two immunoglobulin constant regions. The invention also relates to a chimeric protein comprising at least one biologically active molecule and two molecules of at least a portion of an immunoglobulin constant region that is transported across an epithelium barrier more efficiently than a corresponding homodimer, i.e., wherein both chains are linked to the same biologically active molecule. The invention, thus relates to a chimeric protein comprising a first and a second polypeptide chain linked together, wherein said first chain comprises a biologically active molecule and at least a portion of an immunoglobulin constant region, and said second chain comprises at least a portion of an immunoglobulin constant region, but no immunoglobulin variable region and without any biologically active molecule attached.

The invention relates to a chimeric protein comprising a first and a second polypeptide chain linked together, wherein said first chain comprises a biologically active molecule and at least a portion of an immunoglobulin constant region, and said second chain comprises at least a portion of an immunoglobulin constant region without an immunoglobulin variable region or any biologically active molecule and wherein said second chain is not covalently bonded to any molecule having a molecular weight greater than 1 kD, 2 kD, 5 kD, 10 kD, or 20 kD. In one embodiment, the second chain is not covalently bonded to any molecule having a molecular weight greater than 0-2 kD. In one embodiment, the second chain is not covalently bonded to any molecule having a molecular weight greater than 5-10 kD. In one embodiment, the second chain is not covalently bonded to any molecule having a molecular weight greater than 15-20 kD.

The invention relates to a chimeric protein comprising a first and a second polypeptide chain linked together, wherein said first chain comprises a biologically active molecule and at least a portion of an immunoglobulin constant region, and said second chain comprises at least a portion of an immunoglobulin constant region not covalently linked to any other molecule except the portion of an immunoglobulin of said first polypeptide chain.

The invention relates to a chimeric protein comprising a first and a second polypeptide chain linked together, wherein said first chain comprises a biologically active molecule and at least a portion of an immunoglobulin constant region, and said second chain consists of at least a portion of an immunoglobulin constant region and optionally an affinity tag.

The invention relates to a chimeric protein comprising a first and a second polypeptide chain linked together, wherein said first chain comprises a biologically active molecule and at least a portion of an immunoglobulin constant region, and said second chain consists essentially of at least a portion of an immunoglobulin constant region and optionally an affinity tag.

The invention relates to a chimeric protein comprising a first and a second polypeptide chain linked together, wherein said first chain comprises a biologically active molecule and at least a portion of an immunoglobulin constant region, and said second chain comprises at least a portion of an immunoglobulin constant region without an immunoglobulin variable region or any biologically active molecule and optionally a molecule with a molecular weight less than 10 kD, 5 kD, 2 kD or 1 kD. In one embodiment, the second chain comprises a molecule less than 15-20 kD. In one embodiment, the second chain comprises a molecule less than 5-10 kD. In one embodiment, the second chain comprises a molecule less than 1-2 kD.

The invention relates to a chimeric protein comprising a first and second polypeptide chain, wherein said first chain comprises a biologically active molecule, at least a portion of an immunoglobulin constant region, and at least a first domain, said first domain having at least one specific binding partner, and wherein said second chain comprises at least a portion of an immunoglobulin constant region, and at least a second domain, wherein said second domain is a specific binding partner of said first domain, without any immunoglobulin variable region or a biologically active molecule.

The invention relates to a method of making a chimeric protein comprising a first and second polypeptide chain, wherein the first polypeptide chain and the second polypeptide chain are not the same, said method comprising transfecting a cell with a first DNA construct comprising a DNA molecule encoding a first polypeptide chain comprising a biologically active molecule and at least a portion of an immunoglobulin constant region and optionally a linker, and a second DNA construct comprising a DNA molecule encoding a second polypeptide chain comprising at least a portion of an immunoglobulin constant region without any biologically active molecule or an immunoglobulin variable region, and optionally a linker, culturing the cells under conditions such that the polypeptide chain encoded by the first DNA construct is expressed and the polypeptide chain encoded by the second DNA construct is expressed and isolating monomer-dimer hybrids comprised of the polypeptide chain encoded by the first DNA construct and the polypeptide chain encoded by the second DNA construct.

The invention relates to a method of making a chimeric protein comprising a first and second polypeptide chain, wherein the first polypeptide chain and the second polypeptide chain are not the same, and wherein said first polypeptide chain comprises a biologically active molecule, at least a portion of an immunoglobulin constant region, and at least a first domain, said first domain, having at least one specific binding partner, and wherein said second polypeptide chain comprises at least a portion of an immunoglobulin constant region and a second domain, wherein said second domain, is a specific binding partner of said first domain, without any biologically active molecule or an immunoglobulin variable region, said method comprising transfecting a cell with a first DNA construct comprising a DNA molecule encoding said first polypeptide chain and a second DNA construct comprising a DNA molecule encoding, said second polypeptide chain, culturing the cells under conditions such that the polypeptide chain encoded by the first DNA construct is expressed and the polypeptide chain encoded by the second DNA construct is expressed and isolating monomer-dimer hybrids comprised of the polypeptide chain encoded by the first DNA construct and polypeptide chain encoded by the second DNA construct.

The invention relates to a method of making a chimeric protein of the invention said method comprising transfecting a cell with a first DNA construct comprising a DNA molecule encoding a first polypeptide chain comprising a biologically active molecule and at least a portion of an immunoglobulin constant region and optionally a linker, culturing the cell under conditions such that the polypeptide chain encoded by the first DNA construct is expressed, isolating the polypeptide chain encoded by the first DNA construct and transfecting a cell with a second DNA construct comprising a DNA molecule encoding a second polypeptide chain comprising at least a portion of an immunoglobulin constant region without any biologically active molecule or immunoglobulin variable region, culturing the cell under conditions such that the polypeptide chain encoded by the second DNA construct is expressed, isolating the polypeptide chain, encoded by the second DNA construct, combining the polypeptide chain, encoded by the first DNA construct and the polypeptide chain encoded by the second DNA construct under conditions such that monomer-dimer hybrids comprising the polypeptide chain encoded by the first DNA construct and the polypeptide chain encoded by the second DNA construct form, and isolating said monomer-dimer hybrids.

The invention relates to a method of making a chimeric protein comprising a first and second polypeptide chain, wherein the first polypeptide chain and the second polypeptide chain are not the same, said method comprising transfecting a cell with a DNA construct comprising a DNA molecule encoding a polypeptide chain comprising at least a portion of an immunoglobulin constant region, culturing the cells under conditions such that the polypeptide chain encoded by the DNA construct is expressed with an N terminal cysteine such that dimers of the polypeptide chain form and isolating dimers comprised of two copies of the polypeptide chain encoded by the DNA construct and chemically reacting the isolated dimers with a biologically active molecule, wherein said biologically active molecule has a C terminus thioester, under conditions such that the biologically active molecule reacts predominantly with only one polypeptide chain of the dimer thereby forming a monomer-dimer hybrid.

The invention relates to a method of making a chimeric protein comprising a first and second polypeptide chain, wherein the first polypeptide chain and the second polypeptide chain are not the same, said method comprising transfecting a cell with a DNA construct comprising a DNA molecule encoding a polypeptide chain comprising at least a portion of an immunoglobulin constant region, culturing the cells under conditions such that the polypeptide chain encoded by the DNA construct is expressed with an N terminal cysteine such that dimers of the polypeptide chains form, and isolating dimers comprised of two copies of the polypeptide chain encoded by the DNA construct, and chemically reacting the isolated dimers with a biologically active molecule, wherein said biologically active molecule has a C terminus thioester, such that the biologically active molecule is linked to each chain of the dimer, denaturing the dimer comprised of the portion of the immunoglobulin linked to the biologically active molecule such that monomeric chains form, combining the monomeric chains with a polypeptide chain comprising at least a portion of an immunoglobulin constant region without a biologically active molecule linked to it, such that monomer-dimer hybrids form, and isolating the monomer-dimer hybrids.

The invention relates to a method of making a chimeric protein comprising a first and second polypeptide chain, wherein the first polypeptide chain and the second polypeptide chain are not the same, said method comprising transfecting a cell with a DNA construct comprising a DNA molecule encoding a polypeptide chain comprising at least a portion of an immunoglobulin constant region, culturing the cells under conditions such that the polypeptide chain encoded by the DNA construct is expressed as a mixture of two polypeptide chains, wherein the mixture comprises a polypeptide with an N terminal cysteine, and a polypeptide with a cysteine in close proximity to the N terminus, isolating dimers comprised of the mixture of polypeptide chains encoded by the DNA construct and chemically reacting the isolated dimers with a biologically active molecule, wherein said biologically active molecule has an active thioester, such that at least some monomer-dimer hybrid forms and isolating the monomer-dimer hybrid from said mixture.

The invention relates to a method of treating a disease or condition comprising administering a chimeric protein of the invention thereby treating the disease or condition.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 2a is the amino acid sequence of the chimeric protein Factor VII-Fc (SEQ ID NO: 6). Included in the sequence is the signal peptide (underlined), which is cleaved by the cell and the propeptide (bold), which is recognized by the vitamin K-dependent γ carboxylase which modifies the Factor VII to achieve full activity. The sequence is subsequently cleaved by PACE to yield Factor VII-Fc.

FIG. 2b is the amino acid sequence of the chimeric protein Factor IX-Fc (SEQ ID NO: 8). Included in the sequence is the signal peptide (underlined) which is cleaved by the cell and the propeptide (bold) which is recognized by the vitamin K-dependent γ carboxylase which modifies the Factor IX to achieve full activity. The sequence is subsequently cleaved by PACE to yield Factor IX-Fc.

FIG. 2c is the amino acid sequence of the chimeric protein IFNα-Fc (SEQ ID NO: 10). Included in the sequence is the signal peptide (underlined), which is cleaved by the cell resulting in the mature IFNα-Fc.

FIG. 2d is the amino acid sequence of the chimeric protein IFNα-Fc Δ linker (SEQ ID NO: 12). Included in the sequence is the signal peptide (underlined) which is cleaved by the cell resulting in the mature IFNα-Fc Δ linker.

FIG. 2e is the amino acid sequence of the chimeric protein Flag-Fc (SEQ ID NO: 14). Included in the sequence is the signal peptide (underlined), which is cleaved by the cell resulting in the mature Flag-Fc.

FIG. 2f is the amino acid sequence of the chimeric protein Epo-CCA-Fc (SEQ ID NO: 16). Included in the sequence is the signal peptide (underlined), which is cleaved by the cell resulting in the mature Epo-CCA-Fc. Also shown in bold is the acidic coiled coil domain.

FIG. 2g is the amino acid sequence of the chimeric protein CCB-Fc (SEQ ID NO: 18). Included in the sequence is the signal peptide (underlined), which is cleaved by the cell resulting in the mature CCB-Fc. Also shown in bold is the basic coiled coil domain.

FIG. 2h is the amino acid sequence of the chimeric protein Cys-Fc (SEQ ID NO: 20). Included in the sequence is the signal peptide (underlined), which is cleaved by the cell resulting in the mature Cys-Fc. When this sequence is produced in CHO cells a percentage of the molecules are incorrectly cleaved by the signal peptidase such that two extra amino acids are left on the N terminus, thus preventing the linkage of a biologically active molecule with a C terminal thioester (e.g., via native ligation). When these improperly cleaved species dimerize with the properly cleaved Cys-Fc and are subsequently reacted with biologically active molecules with C terminal thioesters, monomer-dimer hybrids form.

FIG. 2i is the amino acid sequence of the chimeric protein IFNα-GS15-Fc (SEQ ID NO: 22). Included in the sequence is the signal peptide (underlined) which is cleaved by the cell resulting in the mature-IFNα-GS15-Fc.

FIG. 2j is the amino acid sequence of the chimeric protein Epo-Fc (SEQ ID NO: 24). Included in the sequence is the signal peptide (underlined), which is cleaved by the cell resulting in the mature Epo-Fc. Also shown in bold is the 8 amino acid linker.

FIG. 3a is the nucleic acid sequence of the chimeric protein Factor VII-Fc (SEQ ID NO: 7). Included in the sequence is the signal peptide (underlined) and the propeptide (bold) which is recognized by the vitamin K-dependent γ carboxylase which modifies the Factor VII to achieve full activity. The translated sequence is subsequently cleaved by PACE to yield mature Factor VII-Fc.

FIG. 3b is the nucleic acid sequence of the chimeric protein Factor IX-Fc (SEQ ID NO: 9). Included in the sequence is the signal peptide (underlined) and the propeptide (bold) which is recognized by the vitamin K-dependent γ carboxylase which modifies the Factor IX to achieve full activity. The translated sequence is subsequently cleaved by PACE to yield mature Factor IX-Fc.

FIG. 3c is the nucleic acid sequence of the chimeric protein IFNα-Fc (SEQ ID NO: 11). Included in the sequence is the signal peptide (underlined), which is cleaved by the cell after translation resulting in the mature IFNα-Fc.

FIG. 3d is the nucleic acid sequence of the chimeric protein IFNα-Fc Δ linker (SEQ ID NO: 13). Included in the sequence is the signal peptide (underlined) which is cleaved by the cell after translation resulting in the mature IFNα-Fc Δ linker.

FIG. 3e is the amino acid sequence of the chimeric protein Flag-Fc (SEQ ID NO: 15). Included in the sequence is the signal peptide (underlined), which is cleaved by the cell after translation resulting in the mature Flag-Fc.

FIG. 3f is the nucleic acid sequence of the chimeric protein Epo-CCA-Fc (SEQ ID NO: 17). Included in the sequence is the signal peptide (underlined), which is cleaved by the cell after translation resulting in the mature Epo-CCA-Fc. Also shown in bold is the acidic coiled coil domain.

FIG. 3g is the nucleic acid sequence of the chimeric protein CCB-Fc (SEQ ID NO: 19). Included in the sequence is the signal peptide (underlined), which is cleaved by the cell after translation resulting in the mature CCB-Fc. Also shown in bold is the basic coiled coil domain.

FIG. 3h is the nucleic acid sequence of the chimeric protein Cys-Fc (SEQ ID NO: 21). Included in the sequence is the signal peptide (underlined), which is cleaved by the cell after translation resulting in the mature Cys-Fc.

FIG. 3i is the nucleic acid sequence of the chimeric protein IFNα-GS15-Fc (SEQ ID NO: 23). Included in the sequence is the signal peptide (underlined) which is cleaved by the cell after translation resulting in the mature IFNα-GS15-Fc.

FIG. 3j is the nucleic acid sequence of the chimeric protein Epo-Fc (SEQ ID NO: 25). Included in the sequence is the signal peptide (underlined), which is cleaved by the cell after translation resulting in the mature Epo-Fc. Also shown in bold is a nucleic acid sequence encoding the 8 amino acid linker.

FIG. 4 demonstrates ways to form monomer-dimer hybrids through native ligation. SVGCPPC, VGCPPC, STGCPPC and CPPC disclosed as SEQ ID NOS 87-90, respectively.

FIG. 5a shows the amino acid sequence of Fc MESNA (SEQ ID NO:4).

FIG. 5b shows the DNA sequence of Fc MESNA (SEQ ID NO:5).

FIG. 17a shows the nucleotide sequence of interferon β-Fc (SEQ ID NO: 98); FIG. 17b shows the amino acid sequence of interferon β-Fc (SEQ ID NO: 99).

FIG. 18 shows the amino acid sequence of T20(a; SEQ ID NO: 1); T21(b; SEQ ID NO: 2) and T1249(c; SEQ ID NO: 3).

DESCRIPTION OF THE EMBODIMENTS

A. Definitions

Figure 1:
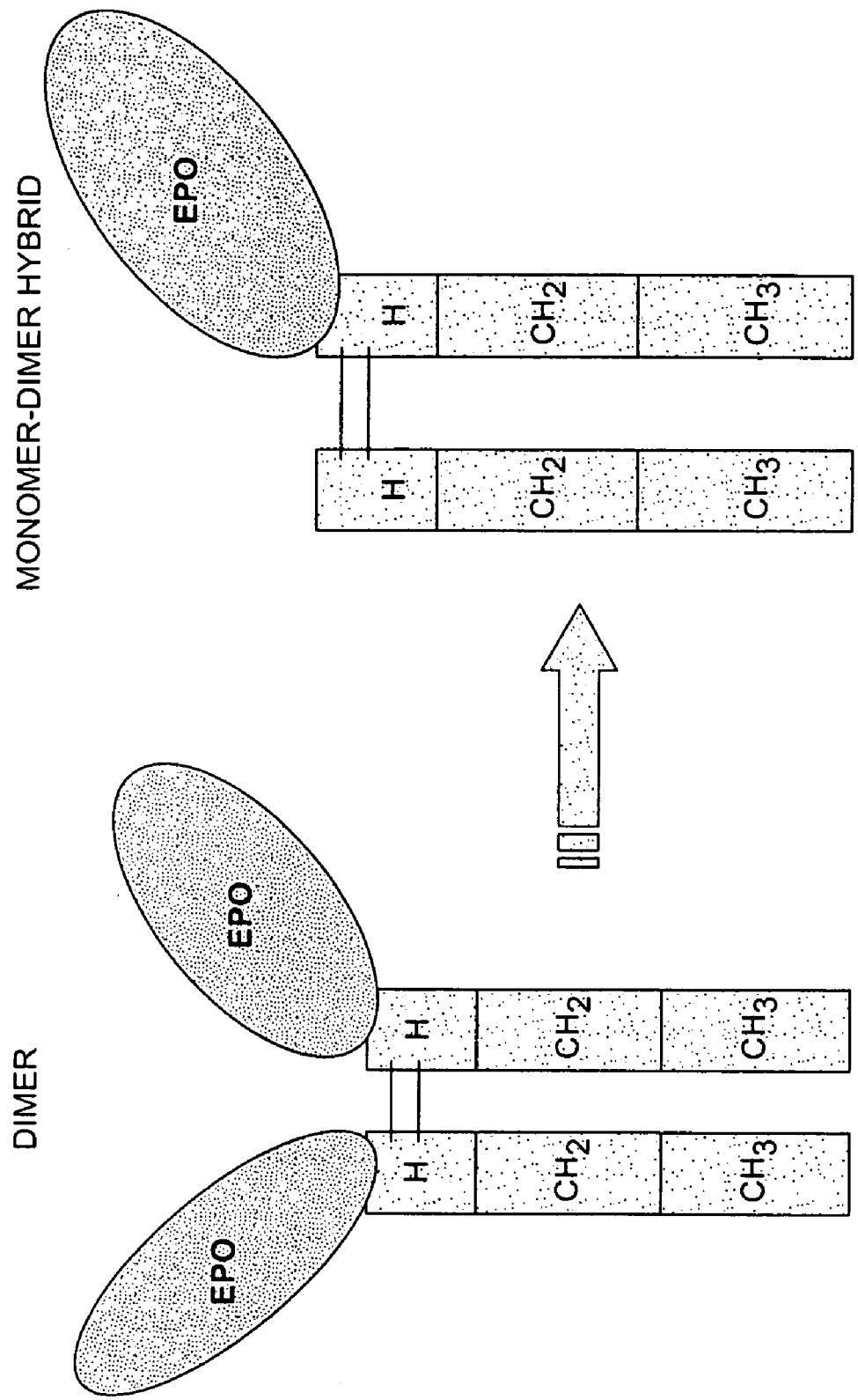
FIG. 1 is a schematic diagram comparing the structure of an EPO-Fc homodimer, or dimer, and the structure of an Epo-FC monomer-dimer hybrid.

Affinity tag, as used herein, means a molecule attached to a second molecule of interest, capable of interacting with a specific binding partner for the purpose of isolating or identifying said second molecule of interest.

Analogs of chimeric proteins of the invention, or proteins or peptides substantially identical to the chimeric proteins of the invention, as used herein, means that a relevant amino acid sequence of a protein or a peptide is at least 70%, 75%, 80%, 85%, 90%, 95%, 97%, 98%, 99%, or 100% identical to a given sequence. By way of example, such sequences may be variants derived from various species, or they may be derived from the given sequence by truncation, deletion, amino acid substitution or addition. Percent identity between two amino acid sequences is determined by standard alignment algorithms such as, for example, Basic Local Alignment Tool (BLAST) described in Altschul et al. 1990, *J. Mol. Biol.*, 215:403-410, the algorithm of Needleman et al. 1970, *J. Mol. Biol.*, 48:444-453; the algorithm of Meyers et al. 1988, *Comput. Appl. Biosci.*, 4:11-17; or Tatusova et al. 1999, *FEMS Microbiol. Lett.*, 174:247-250, etc. Such algorithms are incorporated into the BLASTN, BLASTP and "BLAST 2 Sequences" programs (see www.ncbi.nlm.nih.gov/BLAST). When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON.

Bioavailability, as used herein, means the extent and rate at which a substance is absorbed into a living system or is made available at the site of physiological activity.

Biologically active molecule, as used herein, means a non-immunoglobulin molecule or fragment thereof, capable of treating a disease or condition or localizing or targeting a molecule to a site of a disease or condition in the body by performing a function or an action, or stimulating or responding to a function, an action or a reaction, in a biological context (e.g. in an organism, a cell, or an in vitro model thereof). Biologically active molecules may comprise at least one of polypeptides, nucleic acids, small molecules such as small organic or inorganic molecules.

A chimeric protein, as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A chimeric protein can also include a protein derived from at least 2 different synthetic sources or a protein derived from at least one biological source and at least one synthetic source. A chimeric protein may also comprise a first amino acid sequence derived from a first source, covalently or non-covalently linked to a nucleic acid, derived from any source or a small organic or inorganic molecule derived from any source. The chimeric protein may comprise a linker molecule between the first and second amino acid sequence or between the first amino acid sequence and the nucleic acid, or between the first amino acid sequence and the small organic or inorganic molecule.

Clotting factor, as used herein, means any molecule, or analog thereof, naturally occurring or recombinantly produced which prevents or decreases the duration of a bleeding episode in a subject with a hemostatic disorder. In other words, it means any molecule having clotting activity.

Clotting activity, as used herein, means the ability to participate in a cascade of biochemical reactions that culminates in the formation of a fibrin clot and/or reduces the severity, duration or frequency of hemorrhage or bleeding episode.

Dimer as used herein refers to a chimeric protein comprising a first and second polypeptide chain, wherein the first and second chains both comprise a biologically active molecule, and at least a portion of an immunoglobulin constant region. A homodimer refers to a dimer where both biologically active molecules are the same.

Dimerically linked monomer-dimer hybrid refers to a chimeric protein comprised of at least a portion of an immunloglobulin constant region, e.g. an Fc fragment of an immunoglobulin, a biologically active molecule and a linker which links the two together such that one biologically active molecule is bound to 2 polypeptide chains, each comprising a portion of an immunoglobulin constant region. FIG. 4 shows an example of a dimerically linked monomer-dimer hybrid.

DNA construct, as used herein, means a DNA molecule, or a clone of such a molecule, either single- or double-stranded that has been modified through human intervention to contain segments of DNA combined in a manner that as a whole would not otherwise exist in nature. DNA constructs contain the information necessary to direct the expression of polypeptides of interest. DNA constructs can include promoters, enhancers and transcription terminators. DNA constructs containing the information necessary to direct the secretion of a polypeptide will also contain at least one secretory signal sequence.

Domain, as used herein, means a region of a polypeptide (including proteins as that term is defined) having some distinctive physical feature or role including for example an independently folded structure composed of one section of a polypeptide chain. A domain may contain the sequence of the distinctive physical feature of the polypeptide or it may contain a fragment of the physical feature which retains its binding characteristics (i.e., it can bind to a second domain). A domain may be associated with another domain. In other words, a first domain may naturally bind to a second domain.

A fragment, as used herein, refers to a peptide or polypeptide comprising an amino acid sequence of at least 2 contiguous amino acid residues, of at least 5 contiguous amino acid residues, of at least 10 contiguous amino acid residues, of at least 15 contiguous amino acid residues, of at least 20 contiguous amino acid residues, of at least 25 contiguous amino acid residues, of at least 40 contiguous amino acid residues, of at least 50 contiguous amino acid residues, of at least 100 contiguous amino acid residues, or of at least 200 contiguous amino acid residues or any deletion or truncation of a protein, peptide, or polypeptide.

Hemostasis, as used herein, means the stoppage of bleeding or hemorrhage; or the stoppage of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot.

Linked, as used herein, refers to a first nucleic acid sequence covalently joined to a second nucleic acid sequence. The first nucleic acid sequence can be directly joined or juxtaposed to the second nucleic acid sequence or alternatively an intervening sequence can covalently join the first sequence to the second sequence. Linked as used herein can also refer to a first amino acid sequence covalently, or non-covalently, joined to a second amino acid sequence. The first amino acid sequence can be directly joined or juxtaposed to the second amino acid sequence or alternatively an intervening sequence can covalently join the first amino acid sequence to the second amino acid sequence.

Operatively linked, as used herein, means a first nucleic acid sequence linked to a second nucleic acid sequence such that both sequences are capable of being expressed as a biologically active protein or peptide.

Polypeptide, as used herein, refers to a polymer of amino acids and does not refer to a specific length of the product; thus, peptides, oligopeptides, and proteins are included within the definition of polypeptide. This term does not exclude post-expression modifications of the polypeptide, for example, glycosylation, acetylation, phosphorylation, pegylation, addition of a lipid moiety, or the addition of any organic or inorganic molecule. Included within the definition, are for example, polypeptides containing one or more analogs of an amino acid (including, for example, unnatural amino acids) and polypeptides with substituted linkages, as well as other modifications known in the art, both naturally occurring and non-naturally occurring.

High stringency, as used herein, includes conditions readily determined by the skilled artisan based on, for example, the length of the DNA. Generally, such conditions are defined in Sambrook et al. *Molecular Cloning: A Laboratory Manual,* 2 ed. Vol. 1, pp. 1.101-104, Cold Spring Harbor Laboratory Press (1989), and include use of a pre-washing solution for the nitrocellulose filters 5×SSC, 0.5% SDS, 1.0 mM EDTA (PH 8.0), hybridization conditions of 50% formamide, 6×SSC at 42° C. (or other similar hybridization solution, such as Stark's solution, in 50% formamide at 42° C., and with washing at approximately 68° C., 0.2× SSC, 0.1% SDS. The skilled artisan will recognize that the temperature and wash solution salt concentration can be adjusted as necessary according to factors such as the length of the probe.

Moderate stringency, as used herein, include conditions that can be readily determined by those having ordinary skill in the art based on, for example, the length of the DNA. The basic conditions are set forth by Sambrook et al. *Molecular Cloning: A Laboratory Manual,* 2d ed. Vol. 1, pp. 1.101-104, Cold Spring Harbor Laboratory Press (1989), and include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

A small inorganic molecule, as used herein means a molecule containing no carbon atoms and being no larger than 50 kD.

A small organic molecule, as used herein means a molecule containing at least one carbon atom and being no larger than 50 kD.

Treat, treatment, treating, as used herein means, any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition, the prophylaxis of one or more symptoms associated with a disease or condition.

B. Improvements Offered by Certain Embodiments of the Invention

The invention provides for chimeric proteins (monomer-dimer hybrids) comprising a first and a second polypeptide chain, wherein said first chain comprises a biologically active molecule and at least a portion of an immunoglobulin constant region, and said second chain comprises at least a portion of an immunoglobulin constant region without any biologically active molecule or variable region of an immunoglobulin. FIG. 1 contrasts traditional fusion protein dimers with one example of the monomer-dimer hybrid of the invention. In this example, the biologically active molecule is EPO and the portion of an immunoglobulin is IgG Fc region.

Like other chimeric proteins comprised of at least a portion of an immunoglobulin constant region, the invention provides for chimeric proteins which afford enhanced stability and increased bioavailability of the chimeric protein compared to the biologically active molecule alone. Additionally, however, because only one of the two chains comprises the biologically active molecule, the chimeric protein has a lower molecular weight than a chimeric protein wherein all chains comprise a biologically active molecule and while not wishing to be bound by any theory, this may result in the chimeric protein being more readily transcytosed across the epithelium barrier, e.g., by binding to the FcRn receptor thereby increasing the half-life of the chimeric protein. In one embodiment, the invention thus provides for an improved non-invasive method (e.g. via any mucosal surface, such as, orally, buccally, sublingually, nasally, rectally, vaginally, or via pulmonary or occular route) of administering a therapeutic chimeric protein of the invention. The invention thus provides methods of attaining therapeutic levels of the chimeric proteins of the invention using less frequent and lower doses compared to previously described chimeric proteins (e.g. chimeric proteins comprised of at least a portion of an immunoglobulin constant region and a biologically active molecule, wherein all chains of the chimeric protein comprise a biologically active molecule).

In another embodiment, the invention provides an invasive method, e.g., subcutaneously, intravenously, of administering a therapeutic chimeric protein of the invention. Invasive administration of the therapeutic chimeric protein of the invention provides for an increased half life of the therapeutic chimeric protein which results in using less frequent and lower doses compared to previously described chimeric proteins (e.g. chimeric proteins comprised of at least a portion of an immunoglobulin constant region and a biologically active molecule, wherein all chains of the chimeric protein comprise a biologically active molecule).

Yet another advantage of a chimeric protein wherein only one of the chains comprises a biologically active molecule is the enhanced accessibility of the biologically active molecule for its target cell or molecule resulting from decreased steric hindrance, decreased hydrophobic interactions, decreased ionic interactions, or decreased molecular weight compared to a chimeric protein wherein all chains are comprised of a biologically active molecule.

C. Chimeric Proteins

The invention relates to chimeric proteins comprising one biologically active molecule, at least a portion of an immunoglobulin constant region, and optionally at least one linker. The portion of an immunoglobulin will have both an N, or an amino terminus, and a C, or carboxy terminus. The chimeric protein may have the biologically active molecule linked to the N terminus of the portion of an immunoglobulin. Alternatively, the biologically active molecule may be linked to the C terminus of the portion of an immunoglobulin. In one embodiment, the linkage is a covalent bond. In another embodiment, the linkage is a non-covalent bond.

The chimeric protein can optionally comprise at least one linker; thus, the biologically active molecule does not have to be directly linked to the portion of an immunoglobulin constant region. The linker can intervene in between the biologically active molecule and the portion of an immunoglobulin constant region. The linker can be linked to the N terminus of the portion of an immunoglobulin constant region, or the C terminus of the portion of an immunoglobulin constant region. If the biologically active molecule is comprised of at least one amino acid the biologically active molecule will have an N terminus and a C terminus and the linker can be linked to the N terminus of the biologically active molecule, or the C terminus the biologically active molecule.

The invention relates to a chimeric protein of the formula $X-L_a-F:F$ or $F:F-L_a-X$, wherein X is a biologically active molecule, L is an optional linker, F is at least a portion of an immunoglobulin constant region and, a is any integer or zero. The invention also relates to a chimeric protein of the formula $T_a-X-L_a-F:F$ or $T_a-F:F-L_a-X$, wherein X is a biologically active molecule, L is an optional linker, F is at least a portion of an immunoglobulin constant region, a is any integer or zero, T is a second linker or alternatively a tag that can be used to facilitate purification of the chimeric protein, e.g., a FLAG tag, a histidine tag, a GST tag, a maltose binding protein tag and (:) represents a chemical association, e.g. at least one non-peptide bond. In certain embodiments, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, a hydrogen bond. It will be understood by the skilled artisan that when a equals zero X will be directly linked to F. Thus, for example, a may be 0, 1, 2, 3, 4, 5, or more than 5.

In one embodiment, the chimeric protein of the invention comprises the amino acid sequence of FIG. 2a (SEQ ID NO:6). In one embodiment, the chimeric protein of the invention comprises the amino acid sequence of FIG. 2b (SEQ ID NO:8). In one embodiment, the chimeric protein of the invention comprises the amino acid sequence of FIG. 2c (SEQ ID NO:10). In one embodiment, the chimeric protein of the invention comprises the amino acid sequence of FIG. 2d (SEQ ID NO:12). In one embodiment, the chimeric protein of the invention comprises the amino acid sequence of FIG. 2e (SEQ ID NO:14). In one embodiment, the chimeric protein of the invention comprises the amino acid sequence of FIG. 2f (SEQ ID NO:16). In one embodiment, the chimeric protein of the invention comprises the amino acid sequence of FIG. 2g (SEQ ID NO:18). In one embodiment, the chimeric protein of the invention comprises the amino acid sequence of FIG. 2h (SEQ ID NO:20). In one embodiment, the chimeric protein of the invention comprises the amino acid sequence of FIG. 2i (SEQ ID NO:22). In one embodiment, the chimeric protein of the invention comprises the amino acid sequence of FIG. 2j (SEQ ID NO:24). In one embodiment, the chimeric protein of the invention comprises the amino acid sequence of FIG. 17b (SEQ ID NO: 99).

1. Chimeric Protein Variants

Derivatives of the chimeric proteins of the invention, antibodies against the chimeric proteins of the invention and antibodies against binding partners of the chimeric proteins of the invention are all contemplated, and can be made by altering their amino acids sequences by substitutions, additions, and/or deletions/truncations or by introducing chemical modification that result in functionally equivalent molecules. It will be understood by one of ordinary skill in the art that certain amino acids in a sequence of any protein may be substituted for other amino acids without adversely affecting the activity of the protein.

Various changes may be made in the amino acid sequences of the chimeric proteins of the invention or DNA sequences encoding therefore without appreciable loss of their biological activity, function, or utility. Derivatives, analogs, or mutants resulting from such changes and the use of such derivatives is within the scope of the present invention. In a specific embodiment, the derivative is functionally active, i.e., capable of exhibiting one or more activities associated with the chimeric proteins of the invention, e.g., FcRn binding, viral inhibition, hemostasis, production of red blood cells. Many assays capable of testing the activity of a chimeric protein comprising a biologically active molecule are known in the art. Where the biologically active molecule is an HIV inhibitor, activity can be tested by measuring reverse transcriptase activity using known methods (see, e.g., Barre-Sinoussi et al. 1983, *Science* 220:868; Gallo et al. 1984, *Science* 224:500). Alternatively, activity can be measured by measuring fusogenic activity (see, e.g., Nussbaum et al. 1994, *J. Virol.* 68(9):5411). Where the biological activity is hemostasis, a StaCLot FVIIa-rTF assay can be performed to assess activity of Factor VIIa derivatives (Johannessen et al. 2000, *Blood Coagulation and Fibrinolysis* 11:S159).

Substitutes for an amino acid within the sequence may be selected from other members of the class to which the amino acid belongs (see Table 1). Furthermore, various amino acids are commonly substituted with neutral amino acids, e.g., alanine, leucine, isoleucine, valine, proline, phenylalanine, tryptophan, and methionine (see, e.g., MacLennan et al. 1998, *Acta Physiol. Scand. Suppl.* 643:55-67; Sasaki et al. 1998, *Adv. Biophys.* 35:1-24).

TABLE 1

| Original Residues | Exemplary Substitutions | Typical Substitutions |
| --- | --- | --- |
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |

TABLE 1-continued

| Original Residues | Exemplary Substitutions | Typical Substitutions |
|---|---|---|
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

2. Biologically Active Molecules

The invention contemplates the use of any biologically active molecule as the therapeutic molecule of the invention. The biologically active molecule can be a polypeptide. The biologically active molecule can be a single amino acid. The biologically active molecule can include a modified polypeptide.

The biologically active molecule can include a lipid molecule (e.g. a steroid or cholesterol, a fatty acid, a triacylglycerol, glycerophospholipid, or sphingolipid). The biologically active molecule can include a sugar molecule (e.g. glucose, sucrose, mannose). The biologically active molecule can include a nucleic acid molecule (e.g. DNA, RNA). The biologically active molecule can include a small organic molecule or a small inorganic molecule.

a. Cytokines and Growth Factors

In one embodiment, the biologically active molecule is a growth factor, hormone or cytokine or analog or fragment thereof. The biologically active molecule can be any agent capable of inducing cell growth and proliferation. In a specific embodiment, the biologically active molecule is any agent which can induce erythrocytes to proliferate. Thus, one example of a biologically active molecule contemplated by the invention is EPO. The biologically active molecule can also include, but is not limited to, RANTES, MIP1α, MIP1β, IL-2, IL-3, GM-CSF, growth hormone, tumor necrosis factor (e.g. TNFα or β).

The biologically active molecule can include interferon α, whether synthetically or recombinantly produced, including but not limited to, any one of the about twenty-five structurally related subtypes, as for example interferon-α2a, now commercially available for clinical use (ROFERON®, Roche) and interferon-α2b also approved for clinical use (INTRON®, Schering) as well as genetically engineered versions of various subtypes, including, but not limited to, commercially available consensus interferon α (INFERGEN®, Intermune, developed by Amgen) and consensus human leukocyte interferon see, e.g., U.S. Pat. Nos. 4,695,623; 4,897,471, interferon β, epidermal growth factor, gonadotropin releasing hormone (GnRH), leuprolide, follicle stimulating hormone, progesterone, estrogen, or testosterone.

A list of cytokines and growth factors which may be used in the chimeric protein of the invention has been previously described (see, e.g., U.S. Pat. Nos. 6,086,875, 6,485,726, 6,030,613; WO 03/077834; US2003-0235536A1).

b. Antiviral Agents

In one embodiment, the biologically active molecule is an antiviral agent, including fragments and analogs thereof. An antiviral agent can include any molecule that inhibits or prevents viral replication, or inhibits or prevents viral entry into a cell, or inhibits or prevents viral egress from a cell. In one embodiment, the antiviral agent is a fusion inhibitor. In one embodiment, the antiviral agent is a cytokine which inhibits viral replication. In another embodiment, the antiviral agent is interferon α.

The viral fusion inhibitor for use in the chimeric protein can be any molecule which decreases or prevents viral penetration of a cellular membrane of a target cell. The viral fusion inhibitor can be any molecule that decreases or prevents the formation of syncytia between at least two susceptible cells. The viral fusion inhibitor can be any molecule that decreases or prevents the joining of a lipid bilayer membrane of a eukaryotic cell and a lipid bilayer of an enveloped virus. Examples of enveloped virus include, but are not limited to HIV-1, HIV-2, SIV, influenza, parainfluenza, Epstein-Barr virus, CMV, herpes simplex 1, herpes simplex 2 and respiratory syncytia virus.

The viral fusion inhibitor can be any molecule that decreases or prevents viral fusion including, but not limited to, a polypeptide, a small organic molecule or a small inorganic molecule. In one embodiment, the fusion inhibitor is a polypeptide. In one embodiment, the viral fusion inhibitor is a polypeptide of 3-36 amino acids. In another embodiment, the viral fusion inhibitor is a polypeptide of 3-50 amino acids, 10-65 amino acids, 10-75 amino acids. The polypeptide can be comprised of a naturally occurring amino acid sequence (e.g. a fragment of gp41) including analogs and mutants thereof or the polypeptide can be comprised of an amino acid sequence not found in nature, so long as the polypeptide exhibits viral fusion inhibitory activity.

In one embodiment, the viral fusion inhibitor is a polypeptide, identified as being a viral fusion inhibitor using at least one computer algorithm, e.g., ALLMOTI5, 107×178×4 and PLZIP (see, e.g., U.S. Pat. Nos. 6,013,263; 6,015,881; 6,017,536; 6,020,459; 6,060,065; 6,068,973; 6,093,799; and 6,228,983).

In one embodiment, the viral fusion inhibitor is an HIV fusion inhibitor. In one embodiment, HIV is HIV-1. In another embodiment, HIV is HIV-2. In one embodiment, the HIV fusion inhibitor is a polypeptide comprised of a fragment of the gp41 envelope protein of HIV-1. The HIV fusion inhibitor can comprise, e.g., T20 (SEQ ID NO:1) or an analog thereof, T21 (SEQ ID NO:2) or an analog thereof, T1249 (SEQ ID NO:3) or an analog thereof, $N_{CCG}gp41$ (Louis et al. 2001, *J. Biol. Chem.* 276:(31)29485) or an analog thereof, or 5 helix (Root et al. 2001, *Science* 291:884) or an analog thereof.

Assays known in the art can be used to test for viral fusion inhibiting activity of a polypeptide, a small organic molecule, or a small inorganic molecule. These assays include a reverse transcriptase assay, a p24 assay, or syncytia formation assay (see, e.g., U.S. Pat. No. 5,464,933).

A list of antiviral agents which may be used in the chimeric protein of the invention has been previously described (see, e.g., U.S. Pat. Nos. 6,086,875, 6,485,726, 6,030,613; WO 03/077834; US2003-0235536A1).

c. Hemostatic Agents

In one embodiment, the biologically active molecule is a clotting factor or other agent that promotes hemostasis, including fragments and analogs thereof. The clotting factor can include any molecule that has clotting activity or activates a molecule with clotting activity. The clotting factor can be comprised of a polypeptide. The clotting factor can be, as an example, but not limited to Factor VIII, Factor IX, Factor XI, Factor XII, fibrinogen, prothrombin, Factor V, Factor VII, Factor X, Factor XIII or von Willebrand Factor. In one embodiment, the clotting factor is Factor VII or Factor VIIa. The clotting factor can be a factor that participates in the extrinsic pathway. The clotting factor can be a factor that participates in the intrinsic pathway. Alternatively, the clotting factor can be a factor that participates in both the extrinsic and intrinsic pathway.

The clotting factor can be a human clotting factor or a non-human clotting factor, e.g., derived from a non-human primate, a pig or any mammal. The clotting factor can be chimeric clotting factor, e.g., the clotting factor can comprise a portion of a human clotting factor and a portion of a porcine clotting factor or a portion of a first non-human clotting factor and a portion of a second non-human clotting factor.

The clotting factor can be an activated clotting factor. Alternatively, the clotting factor can be an inactive form of a clotting factor, e.g., a zymogen. The inactive clotting factor can undergo activation subsequent to being linked to at least a portion of an immunoglobulin constant region. The inactive clotting factor can be activated subsequent to administration to a subject. Alternatively, the inactive clotting factor can be activated prior to administration.

In certain embodiments an endopeptidase, e.g., paired basic amino acid cleaving enzyme (PACE), or any PACE family member, such as PCSK1-9, including truncated versions thereof, or its yeast equivalent Kex2 from S. cerevisiae and truncated versions of Kex2 (Kex2 1-675) (see, e.g., U.S. Pat. Nos. 5,077,204; 5,162,220; 5,234,830; 5,885,821; 6,329,176) may be used to cleave a propetide to form the mature chimeric protein of the invention (e.g. factor VII, factor IX).

d. Other Proteinaceous Biologically Active Molecules

In one embodiment, the biologically active molecule is a receptor or a fragment or analog thereof. The receptor can be expressed on a cell surface, or alternatively the receptor can be expressed on the interior of the cell. The receptor can be a viral receptor, e.g., CD4, CCR5, CXCR4, CD21, CD46. The biologically active molecule can be a bacterial receptor. The biologically active molecule can be an extra-cellular matrix protein or fragment or analog thereof, important in bacterial colonization and infection (see, e.g., U.S. Pat. Nos. 5,648,240; 5,189,015; 5,175,096) or a bacterial surface protein important in adhesion and infection (see, e.g., U.S. Pat. No. 5,648,240). The biologically active molecule can be a growth factor, hormone or cytokine receptor, or a fragment or analog thereof, e.g., TNFα receptor, the erythropoietin receptor, CD25, CD122, or CD132.

A list of other proteinaceous molecules which may be used in the chimeric protein of the invention has been previously described (see, e.g., U.S. Pat. Nos. 6,086,875; 6,485,726; 6,030,613; WO 03/077834; US2003-0235536A1).

e. Nucleic Acids

In one embodiment, the biologically active molecule is a nucleic acid, e.g., DNA, RNA. In one specific embodiment, the biologically active molecule is a nucleic acid that can be used in RNA interference (RNAi). The nucleic acid molecule can be as an example, but not as a limitation, an anti-sense molecule or a ribozyme or an aptamer.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as polypeptides (e.g. for targeting host cell receptors in vivo), or agents facilitating transport across the cell membrane (see, e.g., Letsinger et al. 1989, *Proc. Natl. Acad. Sci. USA* 86:6553; Lemaitre et al. 1987, *Proc. Natl. Acad. Sci. USA* 84:648; WO 88/09810,) or the blood-brain barrier (see, e.g., WO 89/10134), hybridization-triggered cleavage agents (see, e.g., Krol et al. 1988, *BioTechniques* 6:958) or intercalating agents (see, e.g., Zon 1988, *Pharm. Res.* 5:539). To this end, the oligonucleotide may be conjugated to another molecule, e.g., a polypeptide, hybridization triggered cross-linking agent, transport agent, or hybridization-triggered cleavage agent.

Ribozyme molecules designed to catalytically cleave target gene mRNA transcripts can also be used to prevent translation of target gene mRNA and, therefore, expression of target gene product. (See, e.g., WO 90/11364; Sarver et al. 1990, *Science* 247, 1222-1225).

Ribozymes are enzymatic RNA molecules capable of catalyzing the specific cleavage of RNA. (See Rossi 1994, *Current Biology* 4:469). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246.

In one embodiment, ribozymes that cleave mRNA at site specific recognition sequences can be used to destroy target gene mRNAs. In another embodiment, the use of hammerhead ribozymes is contemplated. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers 1995, *Molecular Biology and Biotechnology: A Comprehensive Desk Reference*, VCH Publishers, New York, and in Haseloff and Gerlach 1988, *Nature*, 334:585.

f. Small Molecules

The invention also contemplates the use of any therapeutic small molecule or drug as the biologically active molecule in the chimeric protein of the invention. A list of small molecules and drugs which may be used in the chimeric protein of the invention has been previously described (see, e.g., U.S. Pat. Nos. 6,086,875; 6,485,726; 6,030,613; WO 03/077834; US2003-0235536A1).

2. Immunoglobulins

The chimeric proteins of the invention comprise at least a portion of an immunoglobulin constant region. Immunoglobulins are comprised of four protein chains that associate covalently-two heavy chains and two light chains. Each chain is further comprised of one variable region and one constant region. Depending upon the immunoglobulin isotype, the heavy chain constant region is comprised of 3 or 4 constant region domains (e.g. CH1, CH2, CH3, CH4). Some isotypes are further comprised of a hinge region.

The portion of an immunoglobulin constant region can be obtained from any mammal. The portion of an immunoglobulin constant region can include a portion of a human immunoglobulin constant region, a non-human primate immunoglobulin constant region, a bovine immunoglobulin constant region, a porcine immunoglobulin constant region, a murine immunoglobulin constant region, an ovine immunoglobulin constant region or a rat immunoglobulin constant region.

The portion of an immunoglobulin constant region can be produced recombinantly or synthetically. The immunoglobulin can be isolated from a cDNA library. The portion of an immunoglobulin constant region can be isolated from a phage library (See, e.g., McCafferty et al. 1990, *Nature* 348:552, Kang et al. 1991, *Proc. Natl. Acad. Sci. USA* 88:4363; EP 0 589 877 B1). The portion of an immunoglobulin constant region can be obtained by gene shuffling of known sequences (Mark et al. 1992, *Bio/Technol.* 10:779). The portion of an immunoglobulin constant region can be isolated by in vivo recombination (Waterhouse et al. 1993, *Nucl. Acid Res.* 21:2265). The immunoglobulin can be a humanized immunoglobulin (U.S. Pat. No. 5,585,089, Jones et al. 1986, *Nature* 332:323).

The portion of an immunoglobulin constant region can include a portion of an IgG, an IgA, an IgM, an IgD, or an IgE. In one embodiment, the immunoglobulin is an IgG. In another embodiment, the immunoglobulin is IgG1. In another embodiment, the immunoglobulin is IgG2.

The portion of an immunoglobulin constant region can include the entire heavy chain constant region, or a fragment or analog thereof. In one embodiment, a heavy chain constant region can comprise a CH1 domain, a CH2 domain, a CH3 domain, and/or a hinge region. In another embodiment, a heavy chain constant region can comprise a CH1 domain, a CH2 domain, a CH3 domain, and/or a CH4 domain.

The portion of an immunoglobulin constant region can include an Fc fragment. An Fc fragment can be comprised of the CH2 and CH3 domains of an immunoglobulin and the hinge region of the immunoglobulin. The Fc fragment can be the Fc fragment of an IgG1, an IgG2, an IgG3 or an IgG4. In one specific embodiment, the portion of an immunoglobulin constant region is an Fc fragment of an IgG1. In another embodiment, the portion of an immunoglobulin constant region is an Fc fragment of an IgG2.

In another embodiment, the portion of an immunoglobulin constant region is an Fc neonatal receptor (FcRn) binding partner. An FcRn binding partner is any molecule that can be specifically bound by the FcRn receptor with consequent active transport by the FcRn receptor of the FcRn binding partner. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

The FcRn receptor has been isolated from several mammalian species including humans. The sequences of the human FcRn, monkey FcRn rat FcRn, and mouse FcRn are known (Story et al. 1994, *J. Exp. Med.* 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, *Immunology* 92:69) renal proximal tubular epithelium (Kobayashi et al. 2002, *Am. J. Physiol. Renal Physiol.* 282:F358) as well as nasal epithelium, vaginal surfaces, and biliary tree surfaces.

FcRn binding partners of the present invention encompass any molecule that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, *Nature* 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, *Sequences of Proteins of Immunological Interest*, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A,N384A, Q386A, E388A, N389A, N390A, Y391F, K392A, L398A, S400A, D401 A, D413A, K414A, R416A, Q418A, Q419A, N421 A, V422A, S424A, E430A, N434A, T437A, Q438A, K439A, S440A, S444A, and K447A, where for example P238A represents wildtype proline substituted by alanine at position number 238. As an example, one specific embodiment, incorporates the N297A mutation, removing a highly conserved N-glycosylation site. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Moreover, one of the FcRn binding partners of the monomer-dimer hybrid may be mutated and the other FcRn binding partner not mutated at all, or they both may be mutated but with different mutations. Any of the mutations described herein, including N297A, may be used to modify Fc, regardless of the biologically active molecule (e.g., EPO, IFN, Factor IX, T20).

Certain of the above mutations may confer new functionality upon the FcRn binding partner. For example, one embodiment incorporates N297A, removing a highly conserved N-glycosylation site. The effect of this mutation is to reduce immunogenicity, thereby enhancing circulating half life of the FcRn binding partner, and to render the FcRn binding partner incapable of binding to FcγRI, FcγRIIA, FcγRIIB, and FcγRIIIA, without compromising affinity for FcRn (Routledge et al. 1995, *Transplantation* 60:847; Friend et al. 1999, *Transplantation* 68:1632; Shields et al. 1995, *J. Biol. Chem.* 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, *J. Biol. Chem.* 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" (SEQ ID NO: 84) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, *Therapeutic Immunology* 2:77 and Armour et al. 1999, *Eur. J. Immunol.* 29:2613.

In one embodiment, the FcRn binding partner is a polypeptide including the sequence PKNSSMISNTP (SEQ ID NO:26) and optionally further including a sequence selected from HQSLGTQ (SEQ ID NO:27), HQNLSDGK (SEQ ID NO:28), HQNISDGK (SEQ ID NO:29), or VISSHLGQ (SEQ ID NO:30) (U.S. Pat. No. 5,739,277).

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

The skilled artisan will understand that portions of an immunoglobulin constant region for use in the chimeric protein of the invention can include mutants or analogs thereof, or can include chemically modified immunoglobulin constant regions (e.g. pegylated), or fragments thereof (see, e.g., Aslam and Dent 1998, *Bioconjugation: Protein Coupling Techniques For the Biomedical Sciences Macmilan Reference*, London). In one instance, a mutant can provide for enhanced binding of an FcRn binding partner for the FcRn. Also contemplated for use in the chimeric protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display or via chemical library screening (see, e.g., McCafferty et al. 1990, *Nature* 348:552, Kang et al. 1991, *Proc. Natl. Acad. Sci. USA* 88:4363; EP 0 589 877 B1).

3. Optional Linkers

The chimeric protein of the invention can optionally comprise at least one linker molecule. The linker can be comprised of any organic molecule. In one embodiment, the linker is polyethylene glycol (PEG). In another embodiment, the linker is comprised of amino acids. The linker can comprise 1-5 amino acids, 1-10 amino acids, 1-20 amino acids, 10-50 amino acids, 50-100 amino acids, 100-200 amino acids. In one embodiment, the linker is the eight amino acid linker EFAGAAAV (SEQ ID NO:31). Any of the linkers described herein may be used in the chimeric protein of the invention, e.g., a monomer-dimer hybrid, including EFAGAAAV (SEQ ID NO: 31), regardless of the biologically active molecule (e.g. EPO, IFN, Factor IX).

The linker can comprise the sequence $G_n$ (SEQ ID NO: 85). The linker can comprise the sequence $(GA)_n$ (SEQ ID NO:32). The linker can comprise the sequence $(GGS)_n$ (SEQ ID NO:33). The linker can comprise the sequence $(GGS)_n (GGGGS)_n$ (SEQ ID NO:34). In these instances, n may be an integer from 1-10, i.e., 1, 2, 3, 4, 5, 6, 7, 8, 9, 10. Examples of linkers include, but are not limited to, GGG (SEQ ID NO:35), SGGSGGS (SEQ ID NO:36), GGSGGSGGSGGSGGG (SEQ ID NO:37), GGSGGSGGGGSGGGGS (SEQ ID NO:38), GGSGGSGGSGGSGGSGGS (SEQ ID NO:39). The linker does not eliminate or diminish the biological activity of the chimeric protein. Optionally, the linker enhances the biological activity of the chimeric protein, e.g., by further diminishing the effects of steric hindrance and making the biologically active molecule more accessible to its target binding site.

In one specific embodiment, the linker for interferon α is 15-25 amino acids long. In another specific embodiment, the linker for interferon α is 15-20 amino acids long. In another specific embodiment, the linker for interferon α is 10-25 amino acids long. In another specific embodiment, the linker for interferon α is 15 amino acids long. In one embodiment, the linker for interferon α is $(GGGGS)_n$ (SEQ ID NO:40) where G represents glycine, S represents serine and n is an integer from 1-10. In a specific embodiment, n is 3 (SEQ ID NO: 60).

The linker may also incorporate a moiety capable of being cleaved either chemically (e.g. hydrolysis of an ester bond), enzymatically (i.e. incorporation of a protease cleavage sequence) or photolytically (e.g., a chromophore such as 3-amino-3-(2-nitrophenyl) proprionic acid (ANP)) in order to release the biologically active molecule from the Fc protein.

4. Chimeric Protein Dimerization Using Specific Binding Partners

In one embodiment, the chimeric protein of the invention comprises a first polypeptide chain comprising at least a first domain, said first domain having at least one specific binding partner, and a second polypeptide chain comprising at least a second domain, wherein said second domain, is a specific binding partner of said first domain. The chimeric protein thus comprises a polypeptide capable of dimerizing with another polypeptide due to the interaction of the first domain and the second domain. Methods of dimerizing antibodies using heterologous domains are known in the art (U.S. Pat. Nos. 5,807,706 and 5,910,573; Kostelny et al. 1992, *J. Immunol.* 148(5): 1547).

Dimerization can occur by formation of a covalent bond, or alternatively a non-covalent bond, e.g., hydrophobic interaction, Van der Waal's forces, interdigitation of amphiphilic peptides such as, but not limited to, alpha helices, charge-charge interactions of amino acids bearing opposite charges, such as, but not limited to, lysine and aspartic acid, arginine and glutamic acid. In one embodiment, the domain is a helix bundle comprising a helix, a turn and another helix. In another embodiment, the domain is a leucine zipper comprising a peptide having several repeating amino acids in which every seventh amino acid is a leucine residue. In one embodiment, the specific binding partners are fos/jun. (see Branden et al. 1991, *Introduction To Protein Structure*, Garland Publishing, New York).

In another embodiment, binding is mediated by a chemical linkage (see, e.g., Brennan et al. 1985, *Science* 229:81). In this embodiment, intact immunoglobulins, or chimeric proteins comprised of at least a portion of an immunoglobulin constant region are cleaved to generate heavy chain fragments. These fragments are reduced in the presence of the dithiol complexing agent sodium arsenite to stabilize vicinal dithiols and prevent intermolecular disulfide formation. The fragments generated are then converted to thionitrobenzoate (TNB) derivatives. One of the TNB derivatives is then reconverted to the heavy chain fragment thiol by reduction with mercaptoethylamine and is then mixed with an equimolar amount of the other TNB derivative to form a chimeric dimer.

D. Nucleic Acids

The invention relates to a first nucleic acid construct and a second nucleic acid construct each comprising a nucleic acid sequence encoding at least a portion of the chimeric protein of the invention. In one embodiment, the first nucleic acid construct comprises a nucleic acid sequence encoding a portion of an immunoglobulin constant region operatively linked to a second DNA sequence encoding a biologically active molecule, and said second DNA construct comprises a DNA sequence encoding an immunoglobulin constant region without the second DNA sequence encoding a biologically active molecule.

The biologically active molecule can include, for example, but not as a limitation, a viral fusion inhibitor, a clotting factor, a growth factor or hormone, or a receptor, or analog, or fragment of any of the preceding. The nucleic acid sequences can also include additional sequences or elements known in the art (e.g., promoters, enhancers, poly A sequences, affinity tags). In one embodiment, the nucleic acid sequence of the second construct can optionally include a nucleic acid sequence encoding a linker placed between the nucleic acid sequence encoding the biologically active molecule and the portion of the immunoglobulin constant region. The nucleic acid sequence of the second DNA construct can optionally include a linker sequence placed before or after the nucleic acid sequence encoding the biologically active molecule and/ or the portion of the immunoglobulin constant region.

In one embodiment, the nucleic acid construct is comprised of DNA. In another embodiment, the nucleic acid construct is comprised of RNA. The nucleic acid construct can be a vector, e.g., a viral vector or a plasmid. Examples of viral vectors include, but are not limited to adeno virus vector, an adeno associated virus vector or a murine leukemia virus vector. Examples of plasmids include but are not limited to pUC, pGEM and pGEX.

In one embodiment, the nucleic acid construct comprises the nucleic acid sequence of FIG. 3*a* (SEQ ID NO:7). In one embodiment, the nucleic acid construct comprises the nucleic acid sequence of FIG. 3*b* (SEQ ID NO:9). In one embodiment, the nucleic acid construct comprises the nucleic acid sequence of FIG. 3*c* (SEQ ID NO:11). In one embodiment, the nucleic acid construct comprises the nucleic acid sequence of FIG. 3*d* (SEQ ID NO:13). In one embodiment, the nucleic acid construct comprises the nucleic acid sequence of FIG. 3*e* (SEQ ID NO:15). In one embodiment, the nucleic acid construct comprises the nucleic acid sequence of FIG. 3*f* (SEQ ID NO:17). In one embodiment, the nucleic acid construct comprises the nucleic acid sequence of FIG. 3*g* (SEQ ID NO:19). In one embodiment, the nucleic acid construct comprises the nucleic acid sequence of FIG. 3*h* (SEQ ID NO:21). In one embodiment, the nucleic acid construct comprises the nucleic acid sequence of FIG. 3*i* (SEQ ID NO:23). In one embodiment, the nucleic acid construct comprises the nucleic acid sequence of FIG. 3*j* (SEQ ID NO:25). In one embodiment, the nucleic acid construct comprises the nucleic acid sequence of FIG. 17*a* (SEQ ID NO: 98).

Due to the known degeneracy of the genetic code, wherein more than one codon can encode the same amino acid, a DNA sequence can vary from that shown in SEQ ID NOS:7, 9, 11, 13, 15, 17, 19, 21, 23, 25 or 98 and still encode a polypeptide having the corresponding amino acid sequence of SEQ ID NOS:6, 8, 10, 12, 14, 16, 18, 20, 22, 24 or 99 respectively. Such variant DNA sequences can result from silent mutations (e.g. occurring during PCR amplification), or can be the product of deliberate mutagenesis of a native sequence. The invention thus provides isolated DNA sequences encoding polypeptides of the invention, chosen from: (a) DNA comprising the nucleotide sequence of SEQ ID NOS:7, 9, 11, 13, 15, 17, 19, 21, 23, 25 or 98; (b) DNA encoding the polypeptides of SEQ ID NOS:6, 8, 10, 12, 14, 16, 18, 20, 22, 24 or 99; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

In another embodiment, the nucleic acid molecules comprising a sequence encoding the chimeric protein of the invention can also comprise nucleotide sequences that are at least 80% identical to a native sequence. Also contemplated are embodiments in which a nucleic acid molecules comprising a sequence encoding the chimeric protein of the invention comprises a sequence that is at least 90% identical, at least 95% identical, at least 98% identical, at least 99% identical, or at least 99.9% identical to a native sequence. A native sequence can include any DNA sequence not altered by the human hand. The percent identity may be determined by visual inspection and mathematical calculation. Alternatively, the percent identity of two nucleic acid sequences can be determined by comparing sequence information using the GAP computer program, version 6.0 described by Devereux et al. 1984, *Nucl. Acids Res.* 12:387, and available from the University of Wisconsin Genetics Computer Group (UWGCG). The preferred default parameters for the GAP program include: (1) a unary comparison matrix (containing a value of 1 for identities and 0 for non identities) for nucleotides, and the weighted comparison matrix of Gribskov and Burgess 1986, *Nucl. Acids Res.* 14:6745, as described by Schwartz and Dayhoff, eds. 1979, *Atlas of Protein Sequence and Structure*, National Biomedical Research Foundation, pp. 353-358; (2) a penalty of 3.0 for each gap and an additional 0.10 penalty for each symbol in each gap; and (3) no penalty for end gaps. Other programs used by one skilled in the art of sequence comparison may also be used.

E. Synthesis of Chimeric Proteins

Chimeric proteins comprising at least a portion of an immunoglobulin constant region and a biologically active molecule can be synthesized using techniques well known in the art. For example, the chimeric proteins of the invention can be synthesized recombinantly in cells (see, e.g., Sambrook et al. 1989, *Molecular Cloning A Laboratory Manual*, Cold Spring Harbor Laboratory, N.Y. and Ausubel et al. 1989, *Current Protocols in Molecular Biology*, Greene Publishing Associates and Wiley Interscience, N.Y.). Alternatively, the chimeric proteins of the invention can be synthesized using known synthetic methods such as solid phase synthesis. Synthetic techniques are well known in the art (see, e.g., Merrifield, 1973, *Chemical Polypeptides*, (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, *The Proteins* (3d ed.) 2:105; Erikson et al. 1976, *The Proteins* (3d ed.) 2:257; U.S. Pat. No. 3,941,763. Alternatively, the chimeric proteins of the invention can be synthesized using a combination of recombinant and synthetic methods. In certain applications, it may be beneficial to use either a recombinant method or a combination of recombinant and synthetic methods.

Nucleic acids encoding a biologically active molecule can be readily synthesized using recombinant techniques well known in the art. Alternatively, the peptides themselves can be chemically synthesized. Nucleic acids of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. 1988, *Nucl. Acids Res.* 16:3209, methylphosphonate oligonucleotides can be prepared by use of controlled pore glass polymer supports as described in Sarin et al. 1988, *Proc. Natl. Acad. Sci. USA* 85:7448. Additional methods of nucleic acid synthesis are known in the art. (see, e.g., U.S. Pat. Nos. 6,015,881; 6,281,331; 6,469,136).

DNA sequences encoding immunoglobulin constant regions, or fragments thereof, may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA sequences (see, for example, Hieter et al. 1980, *Cell* 22:197-207). The polymerase chain reaction (PCR) method disclosed by Mullis et al. (U.S. Pat. No. 4,683,195) and Mullis (U.S. Pat. No. 4,683,202) may be used. The choice of library and selection of probes for the isolation of such DNA sequences is within the level of ordinary skill in the art. Alternatively, DNA sequences encoding immunoglobulins or fragments thereof can be obtained from vectors known in the art to contain immunoglobulins or fragments thereof.

For recombinant production, a first polynucleotide sequence encoding a portion of the chimeric protein of the invention (e.g. a portion of an immunoglobulin constant region) and a second polynucleotide sequence encoding a portion of the chimeric protein of the invention (e.g. a portion of an immunoglobulin constant region and a biologically active molecule) are inserted into appropriate expression vehicles, i.e. vectors which contains the necessary elements for the transcription and translation of the inserted coding sequence, or in the case of an RNA viral vector, the necessary elements for replication and translation. The nucleic acids encoding the chimeric protein are inserted into the vector in proper reading frame.

The expression vehicles are then transfected or co-transfected into a suitable target cell, which will express the polypeptides. Transfection techniques known in the art include, but are not limited to, calcium phosphate precipitation (Wigler et al. 1978, *Cell* 14:725) and electroporation (Neumann et al. 1982, *EMBO, J.* 1:841), and liposome based reagents. A variety of host-expression vector systems may be utilized to express the chimeric proteins described herein including both prokaryotic or eukaryotic cells. These include, but are not limited to, microorganisms such as bacteria (e.g. *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g. baculovirus) containing an appropriate coding sequence; plant cell systems infected with recombinant virus expression vectors (e.g. cauliflower mosaic virus or tobacco mosaic virus) or transformed with recombinant plasmid expression vectors (e.g. Ti plasmid) containing an appropriate coding sequence; or animal cell systems, including mammalian cells (e.g. CHO, Cos, HeLa cells).

When the chimeric protein of the invention is recombinantly synthesized in a prokaryotic cell it may be desirable to refold the chimeric protein. The chimeric protein produced by this method can be refolded to a biologically active conformation using conditions known in the art, e.g., denaturing under reducing conditions and then dialyzed slowly into PBS.

Depending on the expression system used, the expressed chimeric protein is then isolated by procedures well-established in the art (e.g. affinity chromatography, size exclusion chromatography, ion exchange chromatography).

The expression vectors can encode for tags that permit for easy purification of the recombinantly produced chimeric protein. Examples include, but are not limited to vector pUR278 (Ruther et al. 1983, *EMBO J.* 2:1791) in which the chimeric protein described herein coding sequences may be ligated into the vector in frame with the lac z coding region so that a hybrid protein is produced; pGEX vectors may be used to express chimeric proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PreScission Protease™ (Pharmacia, Peapack, N.J.)) for easy removal of the tag after purification.

To increase efficiency of production, the polynucleotides can be designed to encode multiple units of the chimeric protein of the invention separated by enzymatic cleavage sites. The resulting polypeptide can be cleaved (e.g. by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase yield of polypeptide driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene. Another amplifiable marker is the DHFR cDNA (Simonsen and Levinson 1983, *Proc. Natl. Acad. Sci. USA* 80:2495). Selectable markers are reviewed by Thilly (*Mammalian Cell Technology*, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage A, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the chimeric proteins of the invention may be driven by any of a number of promoters. For example, viral promoters such as the 35S RNA and 19S RNA promoters of CaMV (Brisson et al. 1984, *Nature* 310:511-514), or the coat protein promoter of TMV (Takamatsu et al. 1987, *EMBO J.* 6:307-311) may be used; alternatively, plant promoters such as the small subunit of RUBISCO (Coruzzi et al. 1984, *EMBO J.* 3:1671-1680; Broglie et al. 1984, *Science* 224:838-843) or heat shock promoters, e.g., soybean hsp17.5-E or hsp17.3-B (Gurley et al. 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach 1988, *Methods for Plant Molecular Biology*, Academic Press, NY, Section VIII, pp. 421-463; and Grierson & Corey 1988, *Plant Molecular Biology*, 2d Ed., Blackie, London, Ch. 7-9.

In one insect expression system that may be used to produce the chimeric proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an AcNPV promoter (for example, the polyhedron promoter). Successful insertion of a coding sequence will result in inactivation of the polyhedron gene and production of non-occluded recombinant virus (i.e. virus lacking the proteinaceous coat coded for by the polyhedron gene). These recombinant viruses are then used to infect *Spodoptera frugiperda* cells in which the inserted gene is expressed. (see, e.g., Smith et al. 1983, *J. Virol.* 46:584; U.S. Pat. No. 4,215,051). Further examples of this expression system may be found in Ausubel et al., eds. 1989, *Current Protocols in Molecular Biology*, Vol. 2, Greene Publish. Assoc. & Wiley Interscience.

Another system which can be used to express the chimeric proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing peptide in infected hosts (see, e.g., Logan & Shenk 1984, *Proc. Natl. Acad. Sci. USA* 81:3655). Alternatively, the vaccinia 7.5 K promoter may be used (see, e.g., Mackett et al. 1982, *Proc. Natl. Acad. Sci. USA* 79:7415; Mackett et al. 1984, *J. Virol.* 49:857; Panicali et al. 1982, *Proc. Natl. Acad. Sci. USA* 79:4927).

In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing peptide in infected hosts (see, e.g., Logan & Shenk 1984, *Proc. Natl. Acad. Sci. USA* 81:3655). Alternatively, the vaccinia 7.5 K promoter may be used (see, e.g., Mackett et al. 1982, *Proc. Nat. Acad. Sci. USA* 79:7415; Mackett et al. 1984, *J. Virol.* 49:857; Panicali et al. 1982, *Proc. Natl. Acad. Sci. USA* 79:4927).

Host cells containing DNA constructs of the chimeric protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. Optionally the media can contain bovine calf serum or fetal calf serum. In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g. MEM, DMEM). Selection of a medium appropriate for the particular cell line used is within the level of ordinary skill in the art.

The recombinantly produced chimeric protein of the invention can be isolated from the culture media. The culture medium from appropriately grown transformed or transfected host cells is separated from the cell material, and the presence of chimeric proteins is demonstrated. One method of detecting the chimeric proteins, for example, is by the binding of the chimeric proteins or portions of the chimeric proteins to a specific antibody recognizing the chimeric protein of the invention. An anti-chimeric protein antibody may be a monoclonal or polyclonal antibody raised against the chimeric protein in question. For example, the chimeric protein contains at least a portion of an immunoglobulin constant region. Antibodies recognizing the constant region of many immunoglobulins are known in the art and are commercially available. An antibody can be used to perform an ELISA or a western blot to detect the presence of the chimeric protein of the invention.

The chimeric protein of the invention can be synthesized in a transgenic animal, such as a rodent, cow, pig, sheep, or goat. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, *Proc. Natl. Acad. Sci. USA* 82:4438). Methods of producing transgenic animals are known in the art, including transgenics that produce immunoglobulin molecules (Wagner et al. 1981, *Proc. Natl. Acad. Sci. USA* 78:6376; McKnight et al. 1983, *Cell* 34:335; Brinster et al. 1983, *Nature* 306:332; Ritchie et al. 1984, *Nature* 312:517; Baldassarre et al. 2003, *Theriogenology* 59:831; Robl et al. 2003, *Theriogenology* 59:107; Malassagne et al. 2003, *Xenotransplantation* 10(3):267).

The chimeric protein of the invention can also be produced by a combination of synthetic chemistry and recombinant techniques. For example, the portion of an immunoglobulin constant region can be expressed recombinantly as described above. The biologically active molecule, can be produced using known chemical synthesis techniques (e.g. solid phase synthesis).

The portion of an immunoglobulin constant region can be ligated to the biologically active molecule using appropriate ligation chemistry and then combined with a portion of an immunoglobulin constant region that has not been ligated to a biologically active molecule to form the chimeric protein of the invention. In one embodiment, the portion of an immunoglobulin constant region is an Fc fragment. The Fc fragment can be recombinantly produced to form Cys-Fc and reacted with a biologically active molecule expressing a thioester to make a monomer-dimer hybrid. In another embodiment, an Fc-thioester is made and reacted with a biologically active molecule expressing an N terminus Cysteine (FIG. 4).

In one embodiment, the portion of an immunoglobulin constant region ligated to the biologically active molecule will form homodimers. The homodimers can be disrupted by exposing the homodimers to denaturing and reducing conditions (e.g. beta-mercaptoethanol and 8M urea) and then subsequently combined with a portion of an immunoglobulin constant region not linked to a biologically active molecule to form monomer-dimer hybrids. The monomer-dimer hybrids are then renatured and refolded by dialyzing into PBS and isolated, e.g., by size exclusion or affinity chromatography.

In another embodiment, the portion of an immunoglobulin constant region will form homodimers before being linked to a biologically active molecule. In this embodiment, reaction conditions for linking the biologically active molecule to the homodimer can be adjusted such that linkage of the biologically active molecule to only one chain of the homodimer is favored (e.g. by adjusting the molar equivalents of each reactant).

The biologically active molecule can be chemically synthesized with an N terminal cysteine. The sequence encoding a portion of an immunoglobulin constant region can be subcloned into a vector encoding intein linked to a chitin binding domain (New England Biolabs, Beverly, Mass.). The intein can be linked to the C terminus of the portion of an immunoglobulin constant region. In one embodiment, the portion of the immunoglobulin with the intein linked to its C terminus can be expressed in a prokaryotic cell. In another embodiment, the portion of the immunoglobulin with the intein linked to its C terminus can be expressed in a eukaryotic cell. The portion of immunoglobulin constant region linked to intein can be reacted with MESNA. In one embodiment, the portion of an immunoglobulin constant region linked to intein is bound to a column, e.g., a chitin column and then eluted with MESNA. The biologically active molecule and portion of an immunoglobulin can be reacted together such that nucleophilic rearrangement occurs and the biologically active molecule is covalently linked to the portion of an immunoglobulin via an amide bond. (Dawsen et al. 2000, *Annu. Rev. Biochem.* 69:923). The chimeric protein synthesized this way can optionally include a linker peptide between the portion of an immunoglobulin and the biologically active molecule. The linker can for example be synthesized on the N terminus of the biologically active molecule. Linkers can include peptides and/or organic molecules (e.g. polyethylene glycol and/or short amino acid sequences). This combined recombinant and chemical synthesis allows for the rapid screening of biologically active molecules and linkers to optimize desired properties of the chimeric protein of the invention, e.g., viral inhibition, hemostasis, production of red blood cells, biological half-life, stability, binding to serum proteins or some other property of the chimeric protein. The method also allows for the incorporation of non-natural amino acids into the chimeric protein of the invention which may be useful for optimizing a desired property of the chimeric protein of the invention. If desired, the chimeric protein produced by this method can be refolded to a biologically active conformation using conditions known in the art, e.g., reducing conditions and then dialyzed slowly into PBS.

Alternatively, the N-terminal cysteine can be on the portion of an immunoglobulin constant region, e.g., an Fc fragment. An Fc fragment can be generated with an N-terminal cysteine by taking advantage of the fact that a native Fc has a cysteine at position 226 (see Kabat et al. 1991, *Sequences of Proteins of Immunological Interest*, U.S. Department of Public Health, Bethesda, Md.).

To expose a terminal cysteine, an Fc fragment can be recombinantly expressed. In one embodiment, the Fc fragment is expressed in a prokaryotic cell, e.g., *E. coli*. The sequence encoding the Fc portion beginning with Cys 226 (EU numbering) can be placed immediately following a sequence endcoding a signal peptide, e.g., OmpA, PhoA, STII. The prokaryotic cell can be osmotically shocked to release the recombinant Fc fragment. In another embodiment, the Fc fragment is produced in a eukaryotic cell, e.g., a CHO cell, a BHK cell. The sequence encoding the Fc portion fragment can be placed directly following a sequence encoding a signal peptide, e.g., mouse Igκ light chain or MHC class I Kb signal sequence, such that when the recombinant chimeric protein is synthesized by a eukaryotic cell, the signal sequence will be cleaved, leaving an N terminal cysteine which can than be isolated and chemically reacted with a molecule bearing a thioester (e.g. a C terminal thioester if the molecule is comprised of amino acids).

The N terminal cysteine on an Fc fragment can also be generated using an enzyme that cleaves its substrate at its N terminus, e.g., Factor $X^a$, enterokinase, and the product isolated and reacted with a molecule with a thioester.

The recombinantly expressed Fc fragment can be used to make homodimers or monomer-dimer hybrids.

In a specific embodiment, an Fc fragment is expressed with the human α interferon signal peptide adjacent to the Cys at position 226. When a construct encoding this polypeptide is expressed in CHO cells, the CHO cells cleave the signal peptide at two distinct positions (at Cys 226 and at Val within the signal peptide 2 amino acids upstream in the N terminus direction). This generates a mixture of two species of Fc fragments (one with an N-terminal Val and one with an N-terminal Cys). This in turn results in a mixture of dimeric species (homodimers with terminal Val, homodimers with terminal Cys and heterodimers where one chain has a terminal Cys and the other chain has a terminal Val). The Fc fragments can be reacted with a biologically active molecule having a C terminal thioester and the resulting monomer-dimer hybrid can be isolated from the mixture (e.g. by size exclusion chromatography). It is contemplated that when other signal peptide sequences are used for expression of Fc fragments in CHO cells a mixture of species of Fc fragments with at least two different N termini will be generated.

In another embodiment, a recombinantly produced Cys-Fc can form a homodimer. The homodimer can be reacted with peptide that has a branched linker on the C terminus, wherein the branched linker has two C terminal thioesters that can be reacted with the Cys-Fc. In another embodiment, the biologically active molecule has a single non-terminal thioester that can be reacted with Cys-Fc. Alternatively, the branched linker can have two C terminal cysteines that can be reacted with an Fc thioester. In another embodiment, the branched linker has two functional groups that can be reacted with the Fc thioester, e.g., 2-mercaptoamine. The biologically active molecule may be comprised of amino acids. The biologically active molecule may include a small organic molecule or a small inorganic molecule.

F. Methods of Using Chimeric Proteins

The chimeric proteins of the invention have many uses as will be recognized by one skilled in the art, including, but not limited to methods of treating a subject with a disease or condition. The disease or condition can include, but is not limited to, a viral infection, a hemostatic disorder, anemia, cancer, leukemia, an inflammatory condition or an autoimmune disease (e.g. arthritis, psoriasis, lupus erythematosus, multiple sclerosis), or a bacterial infection (see, e.g., U.S. Pat. Nos. 6,086,875, 6,030,613, 6,485,726; WO 03/077834; US2003-0235536A1).

1. Methods of Treating a Subject with a Red Blood Cell Deficiency

The invention relates to a method of treating a subject having a deficiency of red blood cells, e.g., anemia, comprising administering a therapeutically effective amount of at least one chimeric protein, wherein the chimeric protein comprises a first and a second polypeptide chain, wherein the first chain comprises at least a portion of an immunoglobulin constant region and at least one agent capable of inducing proliferation of red blood cells, e.g., EPO, and the second polypeptide chain comprises at least a portion of an immunoglobulin without the agent capable of inducing red blood cell proliferation of the first chain.

2. Methods of Treating a Subject with a Viral Infection

The invention relates to a method of treating a subject having a viral infection or exposed to a virus comprising administering a therapeutically effective amount of at least one chimeric protein, wherein the chimeric protein comprises a first and a second polypeptide chain, wherein the first chain comprises at least a portion of an immunoglobulin constant region and at least one antiviral agent, e.g., a fusion inhibitor or interferon α and the second polypeptide chain comprises at least a portion of an immunoglobulin without the antiviral agent of the first chain. In one embodiment, the subject is infected with a virus which can be treated with IFNα, e.g., hepatitis C virus. In one embodiment, the subject is infected with HIV, such as HIV-1 or HIV-2.

In one embodiment, the chimeric protein of the invention inhibits viral replication. In one embodiment, the chimeric protein of the invention prevents or inhibits viral entry into target cells, thereby stopping, preventing, or limiting the spread of a viral infection in a subject and decreasing the viral burden in an infected subject. By linking a portion of an immunoglobulin to a viral fusion inhibitor the invention provides a chimeric protein with viral fusion inhibitory activity with greater stability and greater bioavailability compared to viral fusion inhibitors alone, e.g., T20, T21, T1249. Thus, in one embodiment, the viral fusion inhibitor decreases or prevents HIV infection of a target cell, e.g., HIV-1.

a. Conditions That May Be Treated

The chimeric protein of the invention can be used to inhibit or prevent the infection of a target cell by a hepatitis virus, e.g., hepatitis virus C. The chimeric protein may comprise an anti-viral agent which inhibits viral replication.

In one embodiment, the chimeric protein of the invention comprises a fusion inhibitor. The chimeric protein of the invention can be used to inhibit or prevent the infection of any target cell by any virus (see, e.g., U.S. Pat. Nos. 6,086,875, 6,030,613, 6,485,726; WO 03/077834; US2003-0235536A1). In one embodiment, the virus is an enveloped virus such as, but not limited to HIV, SIV, measles, influenza, Epstein-Barr virus, respiratory syncytia virus, or parainfluenza virus. In another embodiment, the virus is a non-enveloped virus such as rhino virus or polio virus The chimeric protein of the invention can be used to treat a subject already infected with a virus. The subject can be acutely infected with a virus. Alternatively, the subject can be chronically infected with a virus. The chimeric protein of the invention can also be used to prophylactically treat a subject at risk for contracting a viral infection, e.g., a subject known or believed to in close contact with a virus or subject believed to be infected or carrying a virus. The chimeric protein of the invention can be used to treat a subject who may have been exposed to a virus, but who has not yet been positively diagnosed.

In one embodiment, the invention relates to a method of treating a subject infected with HCV comprising administering to the subject a therapeutically effective amount of a chimeric protein, wherein the chimeric protein comprises an Fc fragment of an IgG and a cytokine, e.g., IFNα.

In one embodiment, the invention relates to a method of treating a subject infected with HIV comprising administering to the subject a therapeutically effective amount of a chimeric protein wherein the chimeric protein comprises an Fc fragment of an IgG and the viral fusion inhibitor comprises T20.

3. Methods of Treating a Subject Having a Hemostatic Disorder

The invention relates to a method of treating a subject having a hemostatic disorder comprising administering a therapeutically effective amount of at least one chimeric protein, wherein the chimeric protein comprises a first and a second chain, wherein the first chain comprises at least one clotting factor and at least a portion of an immunoglobulin constant region, and the second chain comprises at least a portion of an immunoglobulin constant region.

The chimeric protein of the invention treats or prevents a hemostatic disorder by promoting the formation of a fibrin clot. The chimeric protein of the invention can activate any member of a coagulation cascade. The clotting factor can be a participant in the extrinsic pathway, the intrinsic pathway or both. In one embodiment, the clotting factor is Factor VII or Factor VIIa. Factor VIIa can activate Factor X which interacts with Factor Va to cleave prothrombin to thrombin, which in turn cleaves fibrinogen to fibrin. In another embodiment, the clotting factor is Factor IX or Factor IXa. In yet another embodiment, the clotting factor is Factor VIII or Factor VIIIa. In yet another embodiment, the clotting factor is von Willebrand Factor, Factor XI, Factor XII, Factor V, Factor X or Factor XIII.

a. Conditions That May Be Treated

The chimeric protein of the invention can be used to treat any hemostatic disorder. The hemostatic disorders that may be treated by administration of the chimeric protein of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII.

In one embodiment, the hemostatic disorder is an inherited disorder. In one embodiment, the subject has hemophilia A, and the chimeric protein comprises Factor VII or Factor VIIIa. In another embodiment, the subject has hemophilia A and the chimeric protein comprises Factor VII or Factor VIIa. In another embodiment, the subject has hemophilia B and the chimeric protein comprises Factor IX or Factor IXa. In another embodiment, the subject has hemophilia B and the chimeric protein comprises Factor VII or Factor VIIa. In another embodiment, the subject has inhibitory antibodies to Factor VII or Factor VIIIa and the chimeric protein comprises Factor V11 or Factor VIIa. In yet another embodiment, the subject has inhibitory antibodies against Factor VII or Factor IXa and the chimeric protein comprises Factor VII or Factor VIIa.

The chimeric protein of the invention can be used to prophylactically treat a subject with a hemostatic disorder. The chimeric protein of the invention can be used to treat an acute bleeding episode in a subject with a hemostatic disorder In one embodiment, the hemostatic disorder is the result of a deficiency in a clotting factor, e.g., Factor IX, Factor VII. In another embodiment, the hemostatic disorder can be the result of a defective clotting factor, e.g., von Willebrand's Factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

4. Methods of Treating a Subject in Need of a General Hemostatic Agent

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of at least one chimeric protein, wherein the chimeric protein comprises a first and a second polypeptide chain wherein the first polypeptide chain comprises at least a portion of an immunoglobulin constant region and at least one clotting factor and the second chain comprises at least a portion of an immunoglobulin constant region without the clotting factor of the first polypeptide chain.

a. Conditions That May Be Treated

In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, or stem cell transplantation.

The chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

5. Treatment Modalities

The chimeric protein of the invention can be administered intravenously, subcutaneously, intramuscularly, or via any mucosal surface, e.g., orally, sublingually, buccally, sublingually, nasally, rectally, vaginally or via pulmonary route. The chimeric protein can be implanted within or linked to a biopolymer solid support that allows for the slow release of the chimeric protein to the desired site.

The dose of the chimeric protein of the invention will vary depending on the subject and upon the particular route of administration used. Dosages can range from 0.1 to 100,000 μg/kg body weight. In one embodiment, the dosing range is 0.1-1,000 μg/kg. The protein can be administered continuously or at specific timed intervals. In vitro assays may be employed to determine optimal dose ranges and/or schedules for administration. Many in vitro assays that measure viral infectivity are known in the art. For example, a reverse transcriptase assay, or an rt PCR assay or branched DNA assay can be used to measure HIV concentrations. A StaClot assay can be used to measure clotting activity. Additionally, effective doses may be extrapolated from dose-response curves obtained from animal models.

The invention also relates to a pharmaceutical composition comprising a viral fusion inhibitor, at least a portion of an immunoglobulin and a pharmaceutically acceptable carrier or excipient. Examples of suitable pharmaceutical carriers are described in *Remington's Pharmaceutical Sciences* by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets, lozenges or fast dissolving films according to conventional protocols.

For administration by inhalation, the compounds for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (i.e. intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

The pharmaceutical composition can also be formulated for rectal administration as a suppository or retention enema, e.g., containing conventional suppository bases such as cocoa butter or other glycerides.

6. Combination Therapy

The chimeric protein of the invention can be used to treat a subject with a disease or condition in combination with at least one other known agent to treat said disease or condition.

In one embodiment, the invention relates to a method of treating a subject infected with HIV comprising administering a therapeutically effective amount of at least one chimeric protein comprising a first and a second chain, wherein the first chain comprises an HIV fusion inhibitor and at least a portion of an immunoglobulin constant region and the second chain comprises at least a portion of an immunoglobulin without an HIV fusion inhibitor of the first chain, in combination with at least one other anti-HIV agent. Said other anti-HIV agent can be any therapeutic with demonstrated anti-HIV activity. Said other anti-HIV agent can include, as an example, but not as a limitation, a protease inhibitor (e.g. Amprenavir®, Crixivan®, Ritonivir®), a reverse transcriptase nucleoside analog (e.g. AZT, DDI, D4T, 3TC, Ziagen®), a nonnucleoside analog reverse transcriptase inhibitor (e.g. Sustiva®), another HIV fusion inhibitor, a neutralizing antibody specific to HIV, an antibody specific to CD4, a CD4 mimic, e.g., CD4-IgG2 fusion protein (U.S. patent application Ser. No. 09/912,824) or an antibody specific to CCR5, or CXCR4, or a specific binding partner of CCR5, or CXCR4.

In another embodiment, the invention relates to a method of treating a subject with a hemostatic disorder comprising administering a therapeutically effective amount of at least one chimeric protein comprising a first and a second chain, wherein the first chain comprises at least one clotting factor and at least a portion of an immunoglobulin constant region and the second chain comprises at least a portion of an immunoglobulin constant region without the clotting factor of the first chain, in combination with at least one other clotting factor or agent that promotes hemostasis. Said other clotting factor or agent that promotes hemostasis can be any therapeutic with demonstrated clotting activity. As an example, but not as a limitation, the clotting factor or hemostatic agent can include Factor V, Factor VII, Factor VIII, Factor IX, Factor X, Factor XI, Factor XII, Factor XIII, prothrombin, or fibrinogen or activated forms of any of the preceding. The clotting factor of hemostatic agent can also include anti-fibrinolytic drugs, e.g., epsilon-amino-caproic acid, tranexamic acid.

7. Methods of Inhibiting Viral Fusion With a Target Cell

The invention also relates to an in vitro method of inhibiting HIV fusion with a mammalian cell comprising combining the mammalian cell with at least one chimeric protein, wherein the chimeric protein comprises a first and a second chain, wherein the first chain comprises at least a portion of an immunoglobulin constant region and an HIV inhibitor and the second chain comprises at least a portion of an immunoglobulin constant region without the HIV inhibitor of the first chain. The mammalian cell can include any cell or cell line susceptible to infection by HIV including but not limited to primary human CD4$^+$ T cells or macrophages, MOLT-4 cells, CEM cells, AA5 cells or HeLa cells which express CD4 on the cell surface.

G. Methods of Isolating Chimeric Proteins

Typically, when chimeric proteins of the invention are produced they are contained in a mixture of other molecules such as other proteins or protein fragments. The invention thus provides for methods of isolating any of the chimeric proteins described supra from a mixture containing the chimeric proteins. It has been determined that the chimeric proteins of the invention bind to dye ligands under suitable conditions and that altering those conditions subsequent to binding can disrupt the bond between the dye ligand and the chimeric protein, thereby providing a method of isolating the chimeric protein. In some embodiments the mixture may comprise a monomer-dimer hybrid, a dimer and at least a portion of an immunoglobulin constant region, e.g., an Fc. Thus, in one embodiment, the invention provides a method of isolating a monomer-dimer hybrid. In another embodiment, the invention provides a method of isolating a dimer.

Accordingly, in one embodiment, the invention provides a method of isolating a monomer-dimer hybrid from a mixture, where the mixture comprises a) the monomer-dimer hybrid comprising a first and second polypeptide chain, wherein the first chain comprises a biologically active molecule, and at least a portion of an immunoglobulin constant region and wherein the second chain comprises at least a portion of an immunoglobulin constant region without a biologically active molecule or immunoglobulin variable region;

b) a dimer comprising a first and second polypeptide chain, wherein the first and second chains both comprise a biologically active molecule, and at least a portion of an immunoglobulin constant region; and c) a portion of an immunoglobulin constant region; said method comprising 1) contacting the mixture with a dye ligand linked to a solid support under suitable conditions such that both the monomer-dimer hybrid and the dimer bind to the dye ligand;

2) removing the unbound portion of an immunoglobulin constant region;

3) altering the suitable conditions of 1) such that the binding between the monomer-dimer hybrid and the dye ligand linked to the solid support is disrupted;

4) isolating the monomer-dimer hybrid.

In some embodiments, prior to contacting the mixture with a dye ligand, the mixture may be contacted with a chromatographic substance such as protein A sepharose or the like. The mixture is eluted from the chromatographic substance using an appropriate elution buffer (e.g. a low pH buffer) and the eluate containing the mixture is then contacted with the dye ligand.

Suitable conditions for contacting the mixture with the dye ligand may include a buffer to maintain the mixture at an appropriate pH. An appropriate pH may include a pH of from, 3-10, 4-9, 5-8. In one embodiment, the appropriate pH is 8.0. Any buffering agent known in the art may be used so long as it maintains the pH in the appropriate range, e.g., tris, HEPES, PIPES, MOPS. Suitable conditions may also include a wash buffer to elute unbound species from the dye ligand. The wash buffer may be any buffer which does not disrupt binding of a bound species. For example, the wash buffer can be the same buffer used in the contacting step.

Once the chimeric protein is bound to the dye ligand, the chimeric protein is isolated by altering the suitable conditions. Altering the suitable conditions may include the addition of a salt to the buffer. Any salt may be used, e.g., NaCl, KCl. The salt should be added at a concentration that is high enough to disrupt the binding between the dye ligand and the desired species, e.g., a monomer-dimer hybrid.

In some embodiments where the mixture is comprised of an Fc, a monomer-dimer hybrid, and a dimer, it has been found that the Fc does not bind to the dye ligand and thus elutes with the flow through. The dimer binds more tightly to the dye ligand than the monomer-dimer hybrid. Thus a higher concentration of salt is required to disrupt the bond (e.g. elute) between the dimer and the dye ligand compared to the salt concentration required to disrupt the bond between the dye ligand and the monomer-dimer hybrid.

In some embodiments NaCl may be used to isolate the monomer-dimer hybrid from the mixture. In some embodiments the appropriate concentration of salt which disrupts the bond between the dye ligand and the monomer-dimer hybrid is from 200-700 mM, 300-600 mM, 400-500 mM. In one embodiment, the concentration of NaCl required to disrupt the binding between the dye ligand the monomer-dimer hybrid is 400 mM.

NaCl may also be used to isolate the dimer from the mixture. Typically, the monomer-dimer hybrid is isolated from the mixture before the dimer. The dimer is isolated by adding an appropriate concentration of salt to the buffer, thereby disrupting the binding between the dye ligand and the dimer. In some embodiments the appropriate concentration of salt which disrupts the bond between the dye ligand and the dimer is from 800 mM to 2 M, 900 mM to 1.5 M, 950 mM to 1.2 M. In one specific embodiment, 1 M NaCl is used to disrupt the binding between the dye ligand and the dimer.

The dye ligand may be a bio-mimetic. A bio-mimetic is a human-made substance, device, or system that imitates nature. Thus in some embodiments the dye ligand imitates a molecule's naturally occurring ligand. The dye ligand may be chosen from Mimetic Red 1™, Mimetic Red 2™, Mimetic Orange 1™, Mimetic Orange 2™, Mimetic Orange 3™, Mimetic Yellow 1™, Mimetic Yellow 2™, Mimetic Green 1™, Mimetic Blue 1™, and Mimetic Blue 2™ (Prometic Biosciences (USA) Inc., Wayne, N.J.). In one specific embodiment, the dye ligand is Mimetic Red 2™ (Prometic Biosciences (USA) Inc., Wayne, N.J.). In certain embodiments the dye ligand is linked to a solid support, e.g., from Mimetic Red 1A6XL™, Mimetic Red 2 A6XL™, Mimetic Orange 1 A6XL™, Mimetic Orange 2 A6XL™, Mimetic Orange 3 A6XL™, Mimetic Yellow 1 A6XL™, Mimetic Yellow 2 A6XL™, Mimetic Green 1 A6XL™, Mimetic Blue 1 A6XL™, and Mimetic Blue 2 A6XL™(Prometic Biosciences (USA) Inc., Wayne, N.J.).

The dye ligand may be linked to a solid support. The solid support may be any solid support known in the art (see, e.g., www.seperationsNOW.com). Examples of solid supports may include a bead, a gel, a membrane, a nanoparticle, or a microsphere. The solid support may comprise any material which can be linked to a dye ligand (e.g. agarose, polystyrene, sepharose, sephadex). Solid supports may comprise any synthetic organic polymer such as polyacrylic, vinyl polymers, acrylate, polymethacrylate, and polyacrylamide. Solid supports may also comprise a carbohydrate polymer, e.g., agarose, cellulose, or dextran. Solid supports may comprise inorganic oxides, such as silica, zirconia, titania, ceria, alumina, magnesia (i.e., magnesium oxide), or calcium oxide. Solid supports may also comprise combinations of some of the above-mentioned supports including, but not limited to, dextran-acrylamide.

EXAMPLES

Example 1

Molecular Weight Affects FcRn Mediated Trancytosis

Chimeric proteins comprised of various proteins of interest and IgG Fc were recombinantly produced (Sambrook et al. *Molecular Cloning: A Laboratory Manual*, 2 ed., Cold Spring Harbor Laboratory Press, (1989)) or in the case of contactin-Fc, MAB-β-gal, (a complex of a monoclonal antibody bound to β-gal) (Biodesign International, Saco, Me.) and MAB-GH (a complex of monoclonal antibody and growth hormone) (Research Diagnostics, Inc. Flanders, N.J.) were purchased commercially. Briefly, the genes encoding the protein of interest were cloned by PCR, and then sub-cloned into an Fc fusion expression plasmid. The plasmids were transfected into DG44 CHO cells and stable transfectants were selected and amplified with methotrexate. The chimeric protein homodimers were purified over a protein A column. The proteins tested included interferon α, growth hormone, erythropoietin, follicle stimulating hormone, Factor IX, beta-galactosidase, contactin, and Factor VI II. Linking the proteins to immunoglobulin portions, including the FcRn receptor binding partner, or using commercially available whole antibody (including the FcRn binding region)-antigen complexes permitted the investigation of transcytosis as a function of molecular weight (see U.S. Pat. No. 6,030,613). The chimeric proteins were administered to rats orally and serum levels were measured 2-4 hours post administration using an ELISA for recombinantly produced chimeric proteins and both a western blot and ELISA for commercially obtained antibody complexes and chimeric proteins. Additionally, all of the commercially obtained proteins or complexes as well as Factor VIII-Fc, Factor IX-Fc and Epo-Fc controls were iodinated using IODO beads (Pierce, Pittsburgh, Pa.). The results indicated serum levels of Fc and monoclonal antibody chimeric proteins orally administered to rats are directly related to the size of the protein. The apparent cutoff point for orally administered Fc chimeric proteins is between 200-285 kD. (Table 2).

TABLE 2

| Protein | Size (kD) | Transcytosis |
|---------|-----------|--------------|
| IFNα-Fc | 92 | ++++ |
| GH-Fc | 96 | +++ |
| Epo-Fc | 120 | +++ |
| FSH-Fc | 170 | +++ |
| MAB: GH | 172-194 | +++ |
| FIX-Fc | 200 | + |
| MAB: βGal | 285-420 | − |
| Contactin-Fc | 300 | − |
| FVIIIΔ-Fc | 380 | − |

Example 2

Cloning of pcDNA 3.1-Flag-Fc

The sequence for the FLAG peptide (Asp-Tyr-Lys-Asp-Asp-Asp-Asp-Lys; SEQ ID NO: 91), a common affinity tag used to identify or purify proteins, was cloned into the pcDNA 3.1-Fc plasmid, which contains the mouse Igκ signal sequence followed by the Fc fragment of human IgG1 (amino acids 221-447, EU numbering). The construct was created by overlapping PCR using the following primers:

```
FlagFc-F1:
5'- GCTGGCTAGCCACCATGGA -3'                              (SEQ ID NO:41)

Flag Fc-R1:
5'- CTTGTCATCGTCGTCCTTGTAGTCGTCA                         (SEQ ID NO:42)

CCAGTGGAACCTGGAAC -3'

FlagFc-F2:
5'- GACTACAAGG ACGACGATGA CAAGGACAAA ACTCACACAT          (SEQ ID NO:43)

GCCCACCGTG CCCAGCTCCG GAACTCC -3'

FlagFc-R2:
5'- TAGTGGATCCTCATTTACCCG -3'                            (SEQ ID NO:44)
```

The pcDNA 3.1-Fc template was then added to two separate PCR reactions containing 50 pmol each of the primer pairs FlagFc-F1/R1 or FlagFc-F2/R2 in a 50 µl reaction using Pfu Ultra DNA polymerase (Stratagene, Calif.) according to manufacturer's standard protocol in a MJ Thermocycler using the following cycles: 95° C. 2 minutes; 30 cycles of (95° C. 30 seconds, 52° C. 30 seconds, 72° C. 45 seconds), followed by 72° C. for 10 minutes. The products of these two reactions were then mixed in another PCR reaction (2 µl each) with 50 pmol of FlagFc-F1 and FlagFc-R2 primers in a 50 µl reaction using Pfu Ultra DNA polymerase (Stratagene, Calif.) according to manufacturer's standard protocol in a MJ Thermocycler using the following cycles: 95° C. 2 minutes; 30 cycles of (95° C. 30 seconds, 52° C. 30 seconds, 72° C. 45 seconds), followed by 72° C. for 10 minutes. The resulting fragment was gel purified, digested and inserted into the pcDNA 3.1-Fc plasmid NheI-Bam HI. The resulting plasmid contains the mouse Igκ signal sequence producing the FlagFc protein.

Example 3

Cloning of -Factor VII-Fc construct

The coding sequence for Factor VII, was obtained by RT-PCR from human fetal liver RNA (Clontech, Palo Alto, Calif.). The cloned region is comprised of the cDNA sequence from bp 36 to bp 1430 terminating just before the stop codon. A SbfI site was introduced on the N-terminus. A BspEI site was introduced on the C-terminus. The construct was cloned by PCR using the primers:

```
Downstream:
5' GCTACCTGCAGGCCACCATGGTCTCCCAGGCCCTCAGG 3'  (SEQ ID NO:45)

Upstream:
5' CAGTTCCGGAGCTGGGCACGGCGGGCACGTGTGAGTTT     (SEQ ID NO:46)

TGTCGGGAAAT GG 3'
``` and the following conditions: 95° C. for 5 minutes followed by 30 cycles of 95° C. for 30 seconds, 55° C. for 30 seconds, 72° C. for 1 minute and 45 seconds, and a final extension cycle of 72° C. for 10 minutes.

The fragment was digested SbfI-BspEI and inserted into pED.dC-Fc a plasmid encoding for the Fc fragment of an IgG1.

Example 4

Cloning of Factor IX-Fc Construct

The human Factor IX coding sequence, including the pre-propeptide sequence, was obtained by RT-PCR amplification from adult human liver RNA using the following primers:

```
natFIX-F:
5'-TTACTGCAGAAGGTTATGCAGCGCGTGAACATG- 3'      (SEQ ID NO:47)

F9-R:
5'-TTTTTCGAATTCAGTGAGCTTTGTTTTTTCCTTAATCC- 3' (SEQ ID NO:48)
```

20 ng of adult human liver RNA (Clontech, Palo Alto, Calif.) and 25 pmol each primer were added to a RT-PCR reaction using the SuperScript.™ One-Step RT-PCR with PLATINUM® Taq system (Invitrogen, Carlsbad, Calif.) according to manufacturers protocol. Reaction was carried out in a MJ Thermocycler using the following cycles: 50° C. 30 minutes; 94° C. 2 minutes; 35 cycles of (94° C. 30 seconds, 58° C. 30 seconds, 72° C. 1 minute), and a final 72° C. 10 minutes. The fragment was gel purified using Qiagen Gel Extraction Kit (Qiagen, Valencia, Calif.), and digested with PstI-EcoRI, gel purified, and cloned into the corresponding digest of the pED.dC.XFc plasmid.

Example 5

Cloning of PACE Construct

The coding sequence for human PACE (paired basic amino acid cleaving enzyme), an endoprotease, was obtained by RT-PCR. The following primers were used:

```
PACE-F1:
5'-GGTAAGCTTGCCATGGAGCTGAGGCCCTGGTTGC -3'    (SEQ ID NO:49)

PACE-R1:
5'-GTTTTCAATCTCTAGGACCCACTCGCC -3'           (SEQ ID NO:50)

PACE-F2:
5'-GCCAGGCCACATGACTACTCCGC -3'               (SEQ ID NO:51)

PACE-R2:
5'-GGTGAATTCTCACTCAGGCAGGTGTGAGGGCAGC -3'    (SEQ ID NO:52)
```

The PACE-F1 primer adds a HindIII site to the 5' end of the PACE sequence beginning with 3 nucleotides before the start codon, while the PACE-R2 primer adds a stop codon after amino acid 715, which occurs at the end of the extracellular domain of PACE, as well as adding an EcoRI site to the 3' end of the stop codon. The PACE-R1 and -F2 primers anneal on the 3' and 5' sides of an internal BamHI site, respectively. Two RT-PCR reactions were then set up using 25 pmol each of the primer pairs of PACE-F1/R1 or PACE-F2/R2 with 20 ng of adult human liver RNA (Clontech; Palo Alto, Calif.) in a 50 µl RT-PCR reaction using the SuperScript.™ One-Step RT-PCR with PLATINUM® Taq system (Invitrogen, Carlsbad, Calif.) according to manufacturers protocol. The reaction was carried out in a MJ Thermocycler using the following cycles: 50° C. 30 minutes; 94° C. 2 minutes; 30 cycles of (94° C. 30 seconds, 58° C. 30 seconds, 72° C. 2 minutes), followed by 72° C. 10 minutes. These fragments were each ligated into the vector pGEM T-Easy (Promega, Madison, Wis.) and sequenced fully. The F2-R2 fragment was then subcloned into pcDNA6 V5/His (Invitrogen, Carlsbad, Calif.) using the BamHI/EcoRI sites, and then the F1-R1 fragment was cloned into this construct using the HindIII/BamHI sites. The final plasmid, pcDNA6-PACE, produces a soluble form of PACE (amino acids 1-715), as the transmembrane region has been deleted. The sequence of PACE in pcDNA6-PACE is essentially as described in Harrison et al. 1998, Seminars in Hematology 35:4.

Example 6

Cloning of IFNα-Fc Eight Amino Acid Linker Construct

The human interferon α 2b (hIFNα) coding sequence, including the signal sequence, was obtained by PCR from human genomic DNA using the following primers:

```
IFNa-Sig-F:
5'-GCTACTGCAGCCACCATGGCCTTGACCTTTGCTTTAC-3'   (SEQ ID NO:53)

IFNa-EcoR-R:
5'-CGTTGAATTCTTCCTTACTTCTTAAACTTTCTTGC-3'   (SEQ ID NO:54)
```

Genomic DNA was prepared from 373MG human astrocytoma cell line, according to standard methods (Sambrook et al. 1989, *Molecular Cloning: A Laboratory Manual,* 2d ed., Cold Spring Harbor Laboratory Press). Briefly, approximately 2×10⁵ cells were pelleted by centrifugation, resuspended in 100 µl phosphate buffered saline pH 7.4, then mixed with an equal volume of lysis buffer (100 mM Tris pH 8.0/200 mM NaCl/2% SDS/5 mM EDTA). Proteinase K was added to a final concentration of 100 µg/ml, and the sample was digested at 37° C. for 4 hours with occasional gentle mixing. The sample was then extracted twice with phenol:chloroform, the DNA precipitated by adding sodium acetate pH 7.0 to 100 mM and an equal volume of isopropanol, and pelleted by centrifugation for 10 min at room temperature. The supernatant was removed and the pellet was washed once with cold 70% ethanol and allowed to air dry before resuspending in TE (10 mM Tris pH 8.0/1 mM EDTA).

100 ng of this genomic DNA was then used in a 25 µl PCR reaction with 25 pmol of each primer using Expand High Fidelity System (Boehringer Mannheim, Indianapolis, Ind.) according to manufacturer's standard protocol in a MJ Thermocycler using the following cycles: 94° C. 2 minutes; 30 cycles of (94° C. 30 seconds, 50° C. 30 seconds, 72° C. 45 seconds), and finally 72° C. 10 minutes. The expected sized band (~550 bp) was gel purified with a Gel Extraction kit (Qiagen, Valencia, Calif.), digested with PstI/EcoRI, gel purified again, and cloned into the PstI/EcoRI site of pED-.dC.XFc, which contains an 8 amino acid linker (EFA-GAAAV; SEQ ID NO: 31) followed by the Fc region of human IgG1.

Example 7

Cloning of IFNα Fc ΔLinker Construct

1 µg of purified pED.dC.native human IFNα Fc DNA, from Example 6, was then used as a template in a 25 µl PCR reaction with 25 pmol of each primer IFNa-Sig-F and the following primer:

```
hIFNaNoLinkFc-R:
5'CAGTTCCGGAGCTGGGCACGGCGGGCACGTGTGAGTTTTGTCTTCC   (SEQ ID NO:55)

TTACTTCTTAAACTTTTTGCAAGTTTG- 3'
```

The PCR reaction was carried out using Expand High Fidelity System (Boehringer Mannheim, Indianapolis, Ind.) according to the manufacturer's standard protocol in a Rapid-Cycler thermocycler (Idaho Technology, Salt Lake City, Utah), denaturing at 94° C. for 2 minutes followed by 18 cycles of 95° C. for 15 seconds, 55° C. for 0 seconds, and 72° C. for 1 minute with a slope of 6, followed by 72° C. extension for 10 minutes. A PCR product of the correct size (~525 bp) was gel purified using a Gel Extraction kit (Qiagen; Valencia, Calif.), digested with the PstI and BspEI restriction enzymes, gel purified, and subcloned into the corresponding sites of a modified pED.dC.XFc, where amino acids 231-233 of the Fc region were altered using the degeneracy of the genetic code to incorporate a BspEI site while maintaining the wild type amino acid sequence.

Example 8

Cloning of IFNα Fc GS15 Linker Construct

A new backbone vector was created using the Fc found in the Δlinker construct (containing BspEI and RsrII sites in the 5' end using the degeneracy of the genetic code to maintain the amino acid sequence), using this DNA as a template for a PCR reaction with the following primers:

5' B2xGGGGS:
5' gtcaggatccggcggtggagggagcgacaaaactcacacgtgccc 3'    (SEQ ID NO:56)

3' GGGGS:
5' tgacgcggccgctcatttacccggagacaggg 3'    (SEQ ID NO:57)

A PCR reaction was carried out with 25 pmol of each primer using Pfu Turbo enzyme (Stratagene, La Jolla, Calif.) according to manufacturer's standard protocol in a MJ Thermocycler using the following method: 95° C. 2 minutes; 30 cycles of (95° C. 30 seconds, 54° C. 30 seconds, 72° C. 2 minutes), 72° C. 10 minutes. The expected sized band (~730 bp) was gel purified with a Gel Extraction kit (Qiagen, Valencia Calif.), digested BamHI/NotI; gel purified again, and cloned into the BamHI/NotI digested vector of pcDNA6 ID, a version of pcDNA6 with the IRES sequence and dhfr gene inserted into NotI/XbaI site.

500 ng of purified pED.dC.native human IFNαFc DNA was then used as a template in a 25 µl PCR reaction with the following primers:

5' IFNa for GGGGS:    (SEQ ID NO:81)
5' ccgctagcctgcaggccaccatggccttgac    (SEQ ID NO:58)
c 3'

3' IFNa for GGGGS:    (SEQ ID NO:81)
5' ccggatccgccgccaccttccttactacgtaa    (SEQ ID NO:59)
ac 3'

A PCR reaction was carried out with 25 pmol of each primer using Expand High Fidelity System (Boehringer Mannheim, Indianapolis, Ind.) according to manufacturer's standard protocol in a MJ Thermocycler using the following cycles: 95° C. 2 minutes; 14 cycles of (94° C. 30 seconds, 48° C. 30 seconds, 72° C. 1 minute), 72° C. 10 minutes. The expected sized band (~600 bp) was gel purified with a Gel Extraction kit (Qiagen, Valencia Calif.), digested NheI/BamHI, gel purified again, and cloned into the NheI/BamHI site of the pcDNA6 ID/Fc vector, above, to create an IFNα Fc fusion with a 10 amino acid Gly/Ser linker (2xGGGGS; SEQ ID NO: 86), pcDNA6 ID/IFNα-GS10-Fc.

A PCR reaction was then performed using 500 ng of this pcDNA6 ID/IFNα-GS10-Fc with the following primers A PCR reaction was carried out with 25 pmol of each primer using Expand High Fidelity System (Boehringer Mannheim, Indianapolis, Ind.) according to manufacturer's standard protocol in a MJ Thermocycler using the following cycles: 95° C. 2 minutes; 14 cycles of (94° C. 30 seconds, 48° C. 30 seconds, 72° C. 1 minute), 72° C. 10 minutes. The expected sized band (504 bp) was gel purified with a Gel Extraction kit (Qiagen, Valencia Calif.), digested BamHI/BspEI, the 68 bp band was gel purified, and cloned into the BamHI/BspEI site of the pcDNA6 ID/IFNα-GS10-Fc vector, above, to create an IFNα Fc fusion with a 15 amino acid Gly/Ser linker (3Xggggs; SEQ ID NO: 60), pcDNA6 ID/IFNα-GS15-Fc.

Example 9

Cloning of a Basic Peptide Construct

The hinge region of the human IgG1 Fc fragment from amino acid 221-229 (EU numbering) was replaced with a basic peptide (CCB). Four overlapping oligos were used (IDT, Coralville, Iowa):

5' B3XGGGGS:5'    (SEQ ID NO:60)

gtcaggatccggtggaggcgggtccggcggtggagggagcgacaaa    (SEQ ID NO:61)

actcacacgtgccc 3' fcclv-R:
5' atagaagcctttgaccaggc 3'    (SEQ ID NO:62)

1. CCB-Fc Sense 1:
5' GCC GGC GAA TTC GGT GGT GAG TAC CAG GCC CTG AAG AAG AAG GTG  (SEQ ID NO:63)

GCC CAG CTG AAG GCC AAG AAC CAG GCC CTG AAG AAG AAG 3'

2. CCB-Fc Sense 2:
5' GTG GCC CAG CTG AAG CAC AAG GGC GGC GGC CCC GCC CCA GAG  (SEQ ID NO:64)

CTC CTG GGC GGA CCG A 3'

3. CCB-Fc Anti-Sense 1:
5' CGG TCC GCC CAG GAG CTC TGG GGC GGG GCC GCC GCC CTT GTG CTT  (SEQ ID NO:65)

CAG CTG GGC CAC CTT CTT CTT CAG GGC CTG GTT CTT G 3'

4. CCB-Fc Anti-Sense 2:
5' GCC TTC AGC TGG GCC ACC TTC TTC TTC AGG GCC TGG TAC TCA CCA  (SEQ ID NO:66)

CCG AAT TCG CCG GCA 3'

The oligos were reconstituted to a concentration of 50 μM with dH$_2$0. 5 μl of each oligo were annealed to each other by combining in a thin walled PCR tube with 2.2 μl of restriction buffer #2 (i.e. final concentration of 10 mM Tris HCl pH 7.9, 10 mM MgCl$_2$, 50 mM Na Cl, 1 mM dithiothreitol) (New England Biolabs, Beverly, Mass.) and heated to 95° C. for 30 seconds and then allowed to anneal by cooling slowly for 2 hours to 25° C. 5 pmol of the now annealed oligos were ligated into a pGEM T-Easy vector as directed in the kit manual. (Promega, Madison Wis.). The ligation mixture was added to 50 μl of DH5a competent *E. coli* cells (Invitrogen, Carlsbad, Calif.) on ice for 2 minutes, incubated at 37° C. for 5 minutes, incubated on ice for 2 minutes, and then plated on LB+100 μg/L ampicillin agar plates and placed at 37° C. for 14 hours. Individual bacterial colonies were picked and placed in 5 ml of LB+100 μg/L ampicillin and allowed to grow for 14 hours. The tubes were spun down at 2000×g, 4° C. for 15 minutes and the vector DNA was isolated using Qiagen miniprep kit (Qiagen, Valencia, Calif.) as indicated in the kit manual. 2 μg of DNA was digested with NgoM IV-Rsr II. The fragment was gel purified by the Qiaquick method as instructed in the kit manual (Qiagen, Valencia, Calif.) and ligated to pED.dcEpoFc with NgoM IV/Rsr II. The ligation was transformed into DH5α competent *E. coli* cells and the DNA prepared as described for the pGEM T-Easy vector.

Example 10

Cloning of the Erythropoietin-Acidic Peptide Fc Construct

The hinge region of the human IgG1 Fc fragment in EPO-Fc from amino acid 221-229 (EU numbering) was replaced with an acidic peptide (CCA). Four overlapping oligos were used (IDT, Coralville, Iowa):

1. Epo-CCA-Fc Sense 1:
5' CCG GTG ACA GGG AAT TCG GTG GTG AGT ACC AGG CCC TGG AGA AGG  (SEQ ID NO:67)

AGG TGG CCC AGC TGG AG 3'

2. Epo-CCA-FC Sense 2:
5' GCC GAG AAC CAG GCC CTG GAG AAG GAG GTG GCC CAG CTG GAG  (SEQ ID NO:68)

CAC GAG GGT GGT GGT CCC GCT CCA GAG CTG CTG GGC GGA CA 3'

3. Epo-CCA-Fc Anti-Sense 1:
5' GTC CGC CCA GCA GCT CTG GAG CGG GAC CAC CAC CCT CGT GCT CCA  (SEQ ID NO:69)

GCT GGG CCA C 3'

4. Epo-CCA-Fc Anti-Sense 2:
5' CTC CTT CTC CAG GGC CTG GTT CTC GGC CTC CAG CTG GGC CAC CTC  (SEQ ID NO:70)

CTT CTC CAG GGC CTG GTA CTC ACC ACC GAA TTC CCT GTC ACC GGA 3'

The oligos were reconstituted to a concentration of 50 μM with dH$_2$0. 5 μl of each oligo were annealed to each other by combining in a thin walled PCR tube with 2.2 μl of restriction buffer No. 2 (New England Biolabs, Beverly, Mass.) and heated to 95° C. for 30 seconds and then allowed to cool slowly for 2 hours to 25° C. 5 pmol of the now annealed oligos were ligated into a pGEM T-Easy vector as directed in the kit manual. (Promega, Madison, Wis.). The ligation mixture was added to 50 μl of DH5a competent *E. coli* cells (Invitrogen, Carlsbad, Calif.) on ice for 2 minutes, incubated at 37° C. 5 minutes, incubated on ice for 2 minutes, and then plated on LB+100 μg/L ampicillin agar plates and placed at 37° C. for 14 hours. Individual bacterial colonies were picked and placed in 5 ml of LB+100 μg/L ampicillin and allowed to grow for 14 hours. The tubes were spun down at 2000×g, 4° C. for 15 minutes and the vector DNA was prepared using Qiagen miniprep kit (Qiagen, Valencia, Calif.) as indicated in the kit manual. 2 μg of DNA was digested with Age I-Rsr-II. The fragment was gel purified by the Qiaquick method as instructed in the kit manual (Qiagen, Valencia, Calif.) and ligated into pED.Epo Fc.1 Age I-Rsr II. The ligation was transformed into DH5α competent *E. coli* cells and DNA prepped as described above.

Example 11

Cloning of Cys-Fc Construct

Using PCR and standard molecular biology techniques (Sambrook et al. 1989, *Molecular Cloning: A Laboratory Manual*, 2nd ed., Cold Spring Harbor Laboratory Press), a mammalian expression construct was generated such that the coding sequence for the human IFNα signal peptide was directly abutted against the coding sequence of Fc beginning at the first cysteine residue (Cys 226, EU Numbering). Upon signal peptidase cleavage and secretion from mammalian cells, an Fc protein with an N-terminal cysteine residue was thus generated. Briefly, the primers

```
IFNa-Sig-F  (IFNa-Sig-F:
5'-GCTACTGCAGCCACCATGGCCTTGACCTT        (SEQ ID NO:71)

TGCTTTAC-3')
and

Cys-Fc-R
(5'-CAGTTCCGGAGCTGGGCACGGCGGA           (SEQ ID NO:72)

GAGCCCACAGAGCAGCTTG-3')
``` were used in a PCR reaction to create a fragment linking the IFNα signal sequence with the N terminus of Fc, beginning with Cys 226. 500 ng of pED.dC.native hIFNα Δlinker was added to 25 pmol of each primer in a PCR reaction with Expand High Fidelity System (Boehringer Mannheim, Indianapolis, Ind.) according to manufacturer's standard protocol. The reaction was carried out in a MJ Thermocycler using the following cycles: 94° C. 2 minutes; 30 cycles of (94° C. 30 seconds, 50° C. 30 seconds, 72° C. 45 seconds), and finally 72° C. 10 minutes. The expected sized band (~112 bp) was gel purified with a Gel Extraction kit (Qiagen, Valencia Calif.), digested with the PstI and BspEI restriction enzymes, gel purified, and subcloned into the corresponding sites pED.dC-.native hIFNα Δlinker to generate pED.dC.Cys-Fc (FIG. 5).

Example 12

Protein Expression and Preparation of Fc-MESNA

The coding sequence for Fc (the constant region of human IgG1) was obtained by PCR amplification from an Fc-containing plasmid using standard conditions and reagents, following the manufacturer's recommended procedure to subclone the Fc coding sequence NdeI/SapI. Briefly, the primers 5'-GTGGTCATA TGGGCATTGAAGGCAGAGGCGC-CGCTGCGGTCG-3'(SEQ ID NO:73) and 5'-GGTGGT-TGC TCTTCCGCAAAAACCCGGAGACAGG-GAGAGACTCTTCTGCG-3' (SEQ ID NO:74)-were used to amplify the Fc sequence from 500 ng of the plasmid pED. dC.Epo-Fc using Expand High Fidelity System (Boehringer Mannheim, Basel Switzerland) in a RapidCylcler thermocycler (Idaho Technology Salt Lake City, Utah), denaturing at 95° C. for 2 minutes followed by 18 cycles of 95° C. for 0 sec, 55° C. for 0 sec, and 72° C. for 1 minute with a slope of 4, followed by 72° C. extension for 10 minutes. The PCR product was subcloned into an intermediate cloning vector and sequenced fully, and then subcloned using the NdeI and SapI sites in the pTWIN1 vector following standard procedures. Sambrook, J., Fritsch, E. F. and Maniatis, T. 1989, *Molecular Cloning: A Laboratory Manual*, 2nd ed.; Cold Spring Harbor, N.Y.: Cold Spring Harbor Laboratory Press. This plasmid was then transformed into BL21(DE3) pLysS cells using standard methods. Id. A 1 liter culture of cells was grown to an absorbance reading of 0.8 AU at 37° C., induced with 1 mM isopropyl beta-D-1-thiogalactopyranoside, and grown overnight at 25° C. Cells were pelleted by centrifugation, lysed in 20 mM Tris 8.8/1% NP40/0.1 mM phenylmethanesulfonyl fluoride/1 µg/ml Benzonase (Novagen Madison, Wis.), and bound to chitin beads (New England Biolabs; Beverly, Mass.) overnight at 4° C. Beads were then washed with several column volumes of 20 mM Tris 8.5/500 mM NaCl/1 mM EDTA, and then stored at −80° C. Purified Fc-MESNA was generated by eluting the protein from the beads in 20 mM Tris 8.5/500 mM NaCl/1 mM EDTA/500 mM 2-mercapto ethane sulfonic acid (MESNA), and the eluate was used directly in the coupling reaction, below.

Example 13

Factor VII-Fc Monomer-Dimer Hybrid Expression and Purification

CHO DG-44 cells expressing Factor VII-Fc were established. CHO DG-44 cells were grown at 37° C., 5% $CO_2$, in MEM Alpha plus nucleoside and ribonucleosides and supplemented with 5% heat-inactivated fetal bovine serum until transfection.

DG44 cells were plated in 100 mm tissue culture petri dishes and grown to a confluency of 50%-60%. A total of 10 µg of DNA was used to transfect one 100 mm dish: 7.5 µg of pED.dC.FVII-Fc+1.5 µg pcDNA3/Flag-Fc+1 µg of pcDNA6-PACE. The cells were transfected as described in the Superfect transfection reagent manual (Qiagen, Valencia, Calif.). The media was removed from transfection after 48 hours and replaced with MEM Alpha without nucleosides plus 5% dialyzed fetal bovine serum and 10 µg/ml of Blasticidin (Invitrogen, Carlsbad, Calif.) and 0.2 mg/ml geneticin (Invitrogen, Carlsbad, Calif.). After 10 days, the cells were released from the plate with 0.25% trypsin and transferred into T25 tissue culture flasks, and the selection was continued for 10-14 days until the cells began to grow well as stable cell lines were established. Protein expression was subsequently amplified by the addition 25 nM methotrexate.

Approximately $2 \times 10^7$ cells were used to inoculate 300 ml of growth medium in a 1700 $cm^2$ roller bottle (Corning, Corning, N.Y.) supplemented with 5 µg/ml of vitamin $K_3$ (menadione sodium bisulfite) (Sigma, St Louis, Mo.). The roller bottles were incubated in a 5% $CO_2$ at 37° C. for 72 hours. Then the growth medium was exchanged with 300 ml serum-free production medium (DMEM/F12 with 5 µg/ml bovine insulin and 10 µg/ml Gentamicin) supplemented with 5 µg/L of vitamin $K_3$. The production medium (conditioned medium) was collected every day for 10 days and stored at 4° C. Fresh production medium was added to the roller bottles after each collection and the bottles were returned to the incubator. Pooled media was first clarified using a Sartoclean glass fiber filter (3.0 µm+0.2 µm) (Sartorious Corp. Gottingen, Germany) followed by an Acropack 500 filter (0.8 µm+0.2 µm) (Pall Corp., East Hills, N.Y.). The clarified media was then concentrated approximately 20-fold using Pellicon Biomax tangential flow filtration cassettes (10 kDa MWCO) (Millipore Corp., Billerica, Mass.).

Fc chimeras were then captured from the concentrated media by passage over a Protein A Sepharose 4 Fast Flow Column (AP Biotech, Piscataway, N.J.). A 5×5 cm (100 ml)

column was loaded with ≦5 mg Fc protein per ml column volume at a linear flow rate of 100 cm/hour to achieve a residence time of ≧3 minutes. The column was then washed with >5 column volumes of 1×DPBS to remove non-specifically bound proteins. The bound proteins were eluted with 100 mM Glycine pH 3.0. Elution fractions containing the protein peak were then neutralized by adding 1 part 1 M Tris-HCL, pH 8 to 10 parts elute fraction.

To remove FLAG-Fc homodimers (that is, chimeric Fc dimers with FLAG peptide expressed as fusions with both Fc molecules) from the preparation, the Protein A Sepharose 4 Fast Flow pool was passed over a Unosphere S cation-exchange column (BioRad Corp., Richmond, Calif.). Under the operating conditions for the column, the FLAG-Fc monomer-dimer hybrid is uncharged (FLAG-Fc theoretical pI=6.19) and flows through the column while the hFVII-Fc constructs are positively charged, and thus bind to the column and elute at higher ionic strength. The Protein A Sepharose 4 Fast Flow pool was first dialyzed into 20 mM MES, 20 mM NaCl, pH 6.1. The dialyzed material was then loaded onto a 1.1×11 cm (9.9 ml) column at 150 cm/hour. During the wash and elution, the flow rate was increased to 500 cm/hour. The column was washed sequentially with 8 column volumes of 20 mM MES, 20 mM NaCl, pH 6.1 and 8 column volumes of 20 mM MES, 40 mM NaCl, pH 6.1. The bound protein was eluted with 20 mM MES, 750 mM NaCl, pH 6.1. Elution fractions containing the protein peak were pooled and sterile filtered through a 0.2 μm filter disc prior to storage at −80° C.

An anti-FLAG MAB affinity column was used to separate chimeric Fc dimers with hFVII fused to both Fc molecules from those with one FLAG peptide and one hFVII fusion. The Unosphere S Eluate pool was diluted 1:1 with 20 mM Tris, 50 mM NaCl, 5 mM $CaCl_2$, pH 8 and loaded onto a 1.6×5 cm M2 anti-FLAG sepharose column (Sigma Corp., St. Louis, Mo.) at a linear flow rate of 60 cm/hour. Loading was targeted to <2.5 mg monomer-dimer hybrid/ml column volume. After loading the column was washed with 5 column volumes 20 mM Tris, 50 mM NaCl, 5 mM $CaCl_2$, pH 8.0, monomer-dimer hybrids were then eluted with 100 mM Glycine, pH 3.0. Elution fractions containing the protein peak were then neutralized by adding 1 part 1 M Tris-HCl, pH 8 to 10 parts eluate fraction. Pools were stored at −80° C.

Example 14

Factor IX-Fc Homodimer and Monomer-Dimer Hybrid Expression and Purification

CHO DG-44 cells expressing Factor IX-Fc were established. DG44 cells were plated in 100 mm tissue culture petri dishes and grown to a confluency of 50%-60%. A total of 10 μg of DNA was used to transfect one 100 mm dish: for the homodimer transfection, 8 μg of pED.dC.Factor IX-Fc+2 μg of pcDNA6-PACE was used; for the monomer-dimer hybrid transfection, 8 μg of pED.dC.Factor IX-Fc+1 μg of pcDNA3-FlagFc+1 μg pcDNA6-PACE was used. The cells were transfected as described in the Superfect transfection reagent manual (Qiagen, Valencia, Calif.). The media was removed from transfection after 48 hours and replaced with MEM Alpha without nucleosides plus 5% dialyzed fetal bovine serum and 10 μg/ml of Blasticidin (Invitrogen, Carlsbad, Calif.) for both transfections, while the monomer-dimer hybrid transfection was also supplemented with 0.2 mg/ml geneticin (Invitrogen, Carlsbad, Calif.). After 3 days, the cells were released from the plate with 0.25% trypsin and transferred into T25 tissue culture flasks, and the selection was continued for 10-14 days until the cells began to grow well as stable cell lines were established. Protein expression was subsequently amplified by the addition 10 nM or 100 nM methotrexate for the homodimer or monomer-dimer hybrid, respectively.

For both cell lines, approximately 2×10$^7$ cells were used to inoculate 300 ml of growth medium in a 1700 cm$^2$ roller bottle (Corning, Corning, N.Y.), supplemented with 5 μg/L of vitamin $K_3$ (menadione sodium bisulfite) (Sigma, St. Louis, Mo.). The roller bottles were incubated in a 5% $CO_2$ at 37° C. for approximately 72 hours. The growth medium was exchanged with 300 ml serum-free production medium (DMEM/F12 with 5 μg/ml bovine insulin and 10 μg/ml Gentamicin), supplemented with 5 μg/L of vitamin $K_3$. The production medium (conditioned medium) was collected everyday for 10 days and stored at 4° C. Fresh production medium was added to the roller bottles after each collection and the bottles were returned to the incubator. Prior to chromatography, the medium was clarified using a Supor Cap-100 (0.8/0.2 μm) filter (Pall Gelman Sciences, Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 137 mM NaCl), eluted with 0.1 M glycine, pH 2.7, and then neutralized with $\frac{1}{10}$ volume of 1 M Tris-HCl, pH 9.0. The protein was then dialyzed into PBS.

The monomer-dimer hybrid transfection protein sample was subject to further purification, as it contained a mixture of FIX-Fc:FIX-Fc homodimer, FIX-Fc:Flag-Fc monomer-dimer hybrid, and Flag-Fc:Flag-Fc homodimer. Material was concentrated and applied to a 2.6 cm×60 cm (318 ml) Superdex 200 Prep Grade column at a flow rate of 4 ml/minute (36 cm/hour) and then eluted with 3 column volumes of 1×PBS. Fractions corresponding to two peaks on the UV detector were collected and analyzed by SDS-PAGE. Fractions from the first peak contained either FIX-Fc:FIX-Fc homodimer or FIX-Fc:FlagFc monomer-dimer hybrid, while the second peak contained FlagFc:FlagFc homodimer. All fractions containing the monomer-dimer hybrid but no FlagFc homodimer were pooled and applied directly to a 1.6×5 cm M2 anti-FLAG sepharose column (Sigma Corp., St. Louis, Mo.) at a linear flow rate of 60 cm/hour. After loading, the column was washed with 5 column volumes PBS. Monomer-dimer hybrids were then eluted with 100 mM Glycine, pH 3.0. Elution fractions containing the protein peak were then neutralized by adding $\frac{1}{10}$ volume of 1 M Tris-HCl, and analyzed by reducing and nonreducing SDS-PAGE. Fractions were dialyzed into PBS, concentrated to 1-5 mg/ml, and stored at −80° C.

Example 15

IFNα Homodimer and Monomer-Dimer Hybrid Expression and Purification

CHO DG-44 cells expressing hIFNα were established. DG44 cells were plated in 100 mm tissue culture petri dishes and grown to a confluency of 50%-60%. A total of 10 μg of DNA was used to transfect one 100 mm dish: for the homodimer transfection, 10 μg of the hIFNαFc constructs; for the monomer-dimer hybrid transfection, 8 μg of the hIFNαFc constructs+2 μg of pcDNA3-FlagFc. The cells were transfected as described in the Superfect transfection reagent manual (Qiagen, Valencia, Calif.). The media was removed from transfection after 48 hours and replaced with MEM Alpha without nucleosides plus 5% dialyzed fetal bovine serum, while the monomer-dimer hybrid transfection was also supplemented with 0.2 mg/ml geneticin (Invitrogen, Carlsbad, Calif.). After 3 days, the cells were released from the plate with 0.25% trypsin and transferred into T25 tissue culture flasks, and the selection was continued for 10-14 days until the cells began to grow well and stable cell lines were established. Protein expression was subsequently amplified by the addition methotrexate: ranging from 10 to 50 nM.

For all cell lines, approximately $2 \times 10^7$ cells were used to inoculate 300 ml of growth medium in a 1700 cm$^2$ roller bottle (Corning, Corning, N.Y.). The roller bottles were incubated in a 5% $CO_2$ at 37° C. for approximately 72 hours. Then the growth medium was exchanged with 300 ml serum-free production medium (DMEM/F12 with 5 µg/ml bovine insulin and 10 µg/ml Gentamicin). The production medium (conditioned medium) was collected every day for 10 days and stored at 4° C. Fresh production medium was added to the roller bottles after each collection and the bottles were returned to the incubator. Prior to chromatography, the medium was clarified using a Supor Cap-100 (0.8/0.2 µm) filter from Pall Gelman Sciences (Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 1.37 mM NaCl), eluted with 0.1 M glycine, pH 2.7, and then neutralized with 1/10 volume of 1 M Tris-HCl, pH 9.0. The protein was then dialyzed into PBS.

The monomer-dimer hybrid transfection protein samples were then subject to further purification, as it contained a mixture of IFNαFc:IFNαFc homodimer, IFNαFc:FlagFc monomer-dimer hybrid, and FlagFc:FlagFc homodimer (or Δlinker or GS15 linker). Material was concentrated and applied to a 2.6 cm×60 cm (318 ml) Superdex 200 Prep Grade column at a flow rate of 4 ml/min (36 cm/hr) and then eluted with 3 column volumes of 1×PBS. Fractions corresponding to two peaks on the UV detector were collected and analyzed by SDS-PAGE. Fractions from the first peak contained either IFNαFc:IFNαFc homodimer or IFNαFc:FlagFc monomer-dimer hybrid, while the second peak contained FlagFc:FlagFc homodimer. All fractions containing the monomer-dimer hybrid, but no FlagFc homodimer, were pooled and applied directly to a 1.6×5 cm M2 anti-FLAG sepharose column (Sigma Corp., St. Louis, Mo.) at a linear flow rate of 60 cm/hour. After loading the column was washed with 5 column volumes PBS monomer-dimer hybrids were then eluted with 100 mM Glycine, pH 3.0. Elution fractions containing the protein peak were then neutralized by adding 1/10 volume of 1 M Tris-HCl, and analyzed by reducing and non-reducing SDS-PAGE. Fractions were dialyzed into PBS, concentrated to 1-5 mg/ml, and stored at −80° C.

Example 16

Coiled Coil Protein Expression and Purification

The plasmids, pED.dC Epo-CCA-Fc and pED.dC CCB-Fc will be transfected either alone or together at a 1:1 ratio into CHO DG44 cells. The cells will be transfected as described in the Superfect transfection reagent manual (Qiagen, Valencia, Calif.). The media will be removed after 48 hours and replaced with MEM Alpha w/o nucleosides plus 5% dialyzed fetal bovine serum. Purification will be done by affinity chromatography over a protein A column according to methods known in the art. Alternatively, purification can be achieved using size exclusion chromatography.

Example 17

Cys-Fc Expression and Purification

CHO DG-44 cells expressing Cys-Fc were established. The pED.dC.Cys-Fc expression plasmid, which contains the mouse dihydrofolate reductase (dhfr) gene, was transfected into CHO DG44 (dhfr deficient) cells using Superfect reagent (Qiagen; Valencia, Calif.) according to manufacturer's protocol, followed by selection for stable transfectants in αMEM (without nucleosides) tissue culture media supplemented with 5% dialyzed FBS and penicillin/streptomycin antibiotics (Invitrogen; Carlsbad, Calif.) for 10 days. The resulting pool of stably transfected cells were then amplified with 50 nM methotrexate to increase expression. Approximately $2 \times 10^7$ cells were used to inoculate 300 ml of growth medium in a 1700 cm$^2$ roller bottle (Corning, Corning, N.Y.). The roller bottles were incubated in a 5% $CO_2$ at 37° C. for approximately 72 hours. The growth medium was exchanged with 300 ml serum-free production medium (DMEM/F12 with 5 µg/ml bovine insulin and 10 µg/ml Gentamicin). The production medium (conditioned medium) was collected every day for 10 days and stored at 4° C. Fresh production medium was added to the roller bottles after each collection and the bottles were returned to the incubator. Prior to chromatography, the medium was clarified using a Supor Cap-100 (0.8/0.2 µm) filter from Pall Gelman Sciences (Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 137 mM NaCl), eluted with 0.1 M glycine, pH 2.7, and then neutralized with 1/10 volume of 1 M Tris-HCl, pH 9.0. Protein was dialyzed into PBS and used directly in conjugation reactions.

Example 18

Coupling of T20-thioesters to Cys-Fc

Cys-Fc (4 mg, 3.2 mg/ml final concentration) and either T20-thioester or T20-PEG-thioester (2 mg, approximately 5 molar equivalents) were incubated for 16 hours at room temperature in 0.1 M Tris 8/10 mM MESNA. Analysis by SDS-PAGE (Tris-Gly gel) using reducing sample buffer indicated the presence of a new band approximately 5 kDa larger than the Fc control (>40-50% conversion to the conjugate). Previous N-terminal sequencing of Cys-Fc and unreacted Cys-Fc indicated that the signal peptide is incorrectly processed in a fraction of the molecules, leaving a mixture of (Cys)-Fc, which will react through native ligation with peptide-thioesters, and (Val)-(Gly)-(Cys)-Fc, which will not. As the reaction conditions are insufficient to disrupt the dimerization of the Cys-Fc molecules, this reaction generated a mixture of T20-Cys-Fc:T20-Cys-Fc homodimers, T20-Cys-Fc: Fc monomer-dimer hybrids, and Cys-Fc:Cys-Fc Fc-dimers. This protein was purified using size exclusion chromatography as indicated above to separate the three species. The result was confirmed by SDS-PAGE analysis under nonreducing conditions.

Example 19

Antiviral Assay for IFNα Activity

Figure 6:
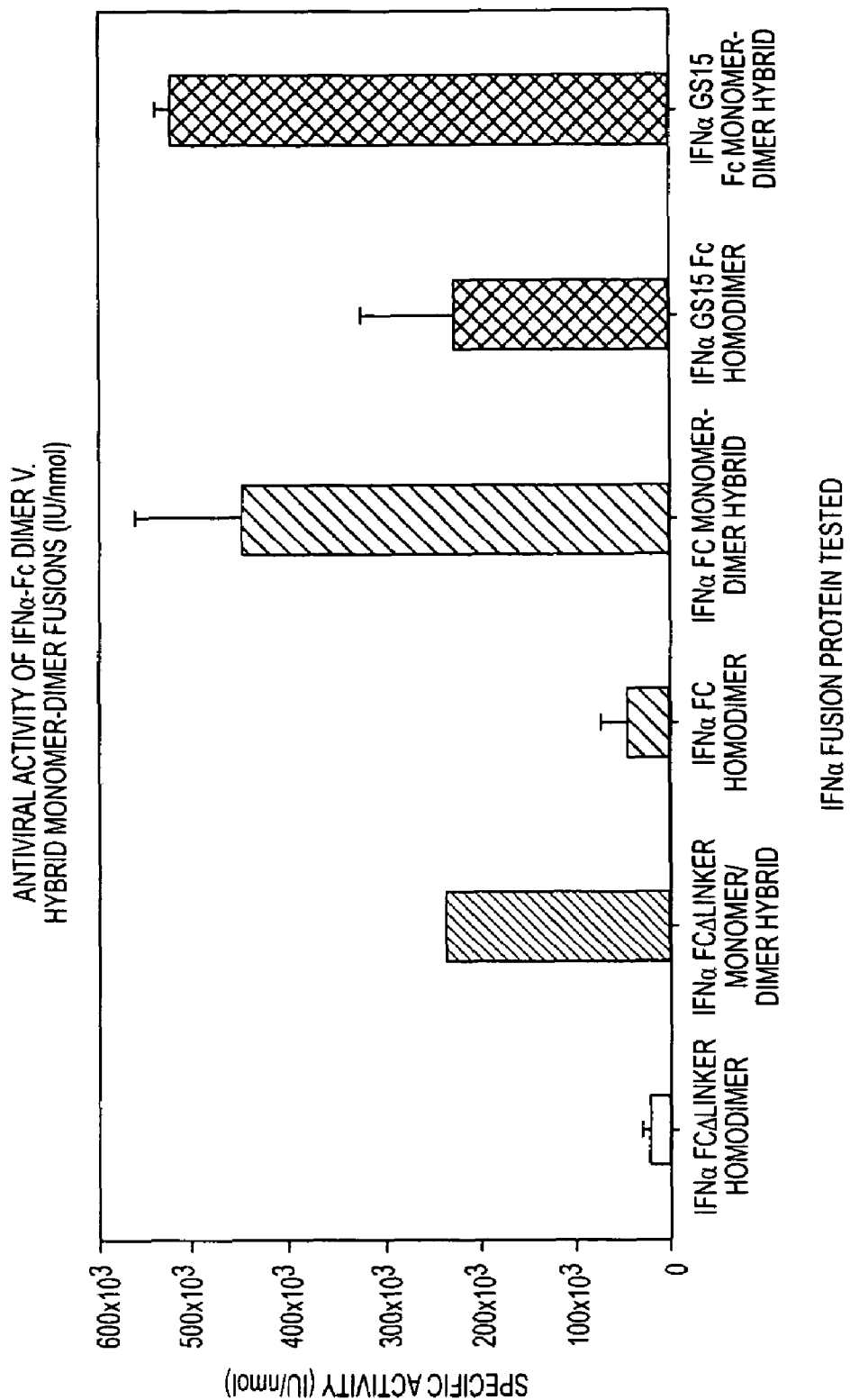
FIG. 6 compares antiviral activity of IFNα homo-dimer (i.e. comprised of 2 IFNα molecules) with an IFNα monomer-dimer hybrid (i.e. comprised of 1 IFNα molecule).

Antiviral activity (IU/ml) of IFNα fusion proteins was determined using a CPE (cytopathic effect) assay. A549 cells were plated in a 96 well tissue culture plate in growth media (RPMI 1640 supplemented with 10% fetal bovine serum (FBS) and 2 mM L-glutamine) for 2 hours at 37° C., 5% $CO_2$. IFNα standards and IFNα fusion proteins were diluted in growth media and added to cells in triplicate at 20 hours at 37° C., 5% $CO_2$. Following incubation, all media was removed from wells, encephalomyocarditis virus (EMC) virus was diluted in growth media and added (3000 pfu/well) to each well with the exception of control wells. Plates were incubated at 37° C., 5% $CO_2$ for 28 hours. Living cells were fixed with 10% cold trichloroacetic acid (TCA) and then stained with Sulforhodamine B (SRB) according to published protocols (Rubinstein et al. 1990, *J. Natl. Cancer Inst.* 82, 1113). The SRB dye was solubilized with 10 mM Tris pH 10.5 and read on a spectrophotometer at 490 nm. Samples were analyzed by comparing activities to a known standard curve World Health Organization IFNα 2b International Standard ranging from 5 to 0.011 IU/ml. The results are presented below in Table 3 and FIG. 6 and demonstrate increased antiviral activity of monomer-dimer hybrids.

TABLE 3

INTERFERON ANTIVIRAL ASSAY
HOMODIMER V. MONOMER-DIMER HYBRID

| Protein | Antiviral Activity (IU/nmol) | Std dev |
|---|---|---|
| IFNαFc 8aa linker homodimer | $0.45 \times 10^5$ | $0.29 \times 10^5$ |
| IFNαFc 8aa linker: FlagFc monomer-dimer hybrid | $4.5 \times 10^5$ | $1.2 \times 10^5$ |
| IFNαFc Δ linker homodimer | $0.22 \times 10^5$ | $0.07 \times 10^5$ |
| IFNαFc Δ delta linker: FlagFc monomer-dimer hybrid | $2.4 \times 10^5$ | $0.0005 \times 10^5$ |
| IFNαFc GS15 linker homodimer | $2.3 \times 10^5$ | $1.0 \times 10^5$ |
| IFNαFc GS15 linker monomer-dimer hybrid | $5.3 \times 10^5$ | $0.15 \times 10^5$ |

Example 20

FVIIa Clotting Activity Analysis

Figure 7:
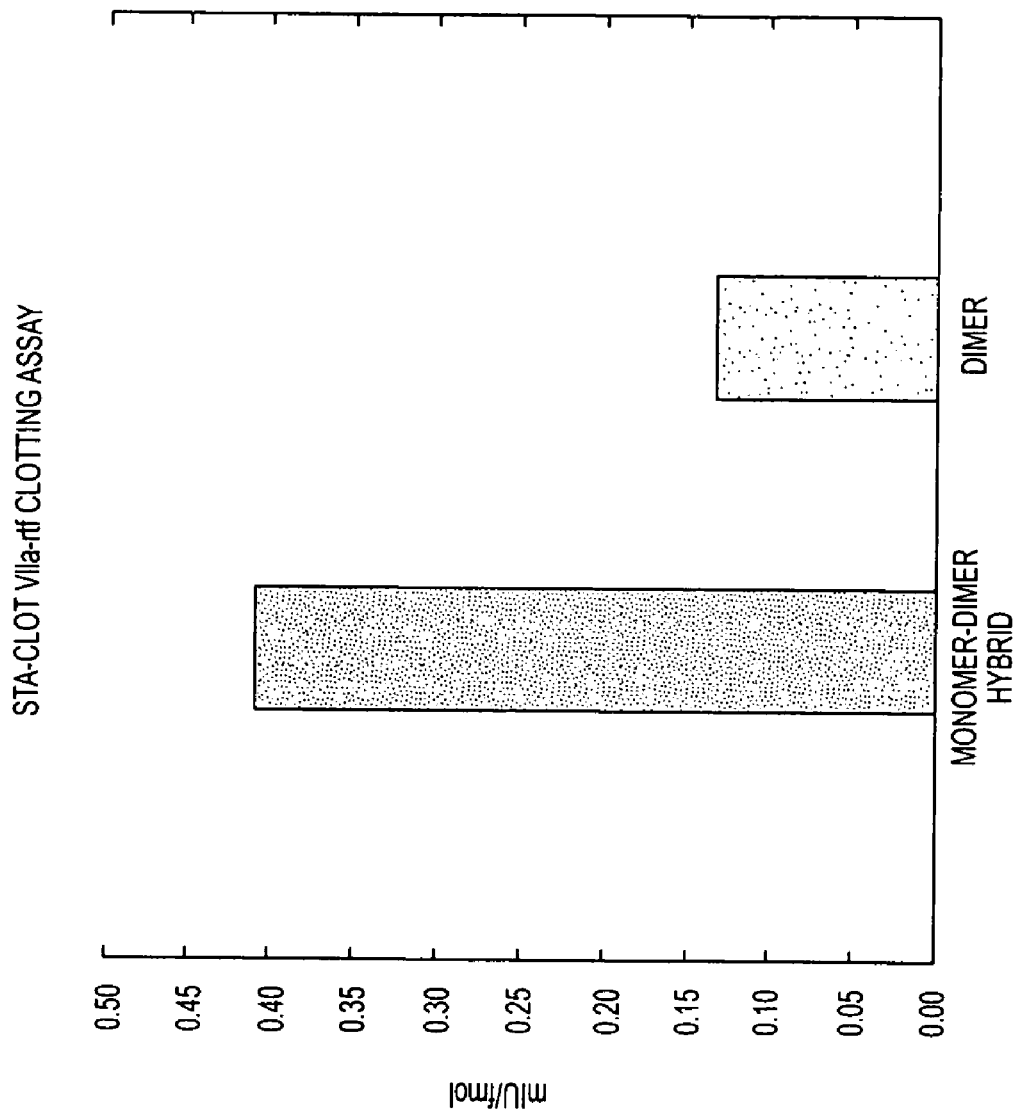
FIG. 7 is a comparison of clotting activity of a chimeric monomer-dimer hybrid Factor VIIa-Fc (one Factor VII molecule) and a chimeric homodimer Factor VIIa-Fc (two Factor VII molecules).

The StaClot FVIIa-rTF assay kit was purchased from Diagnostica Stago (Parsippany, N.J.) and modified as described in Johannessen et al. 2000, *Blood Coagulation and Fibrinolysis* 11:S159. A standard curve was preformed with the FVIIa World Health Organization standard 89/688. The assay was used to compare clotting activity of monomer-dimer hybrids compared to homodimers. The results showed the monomer-dimer hybrid had four times the clotting activity compared to the homodimer (FIG. 7).

Example 21

Figure 8:
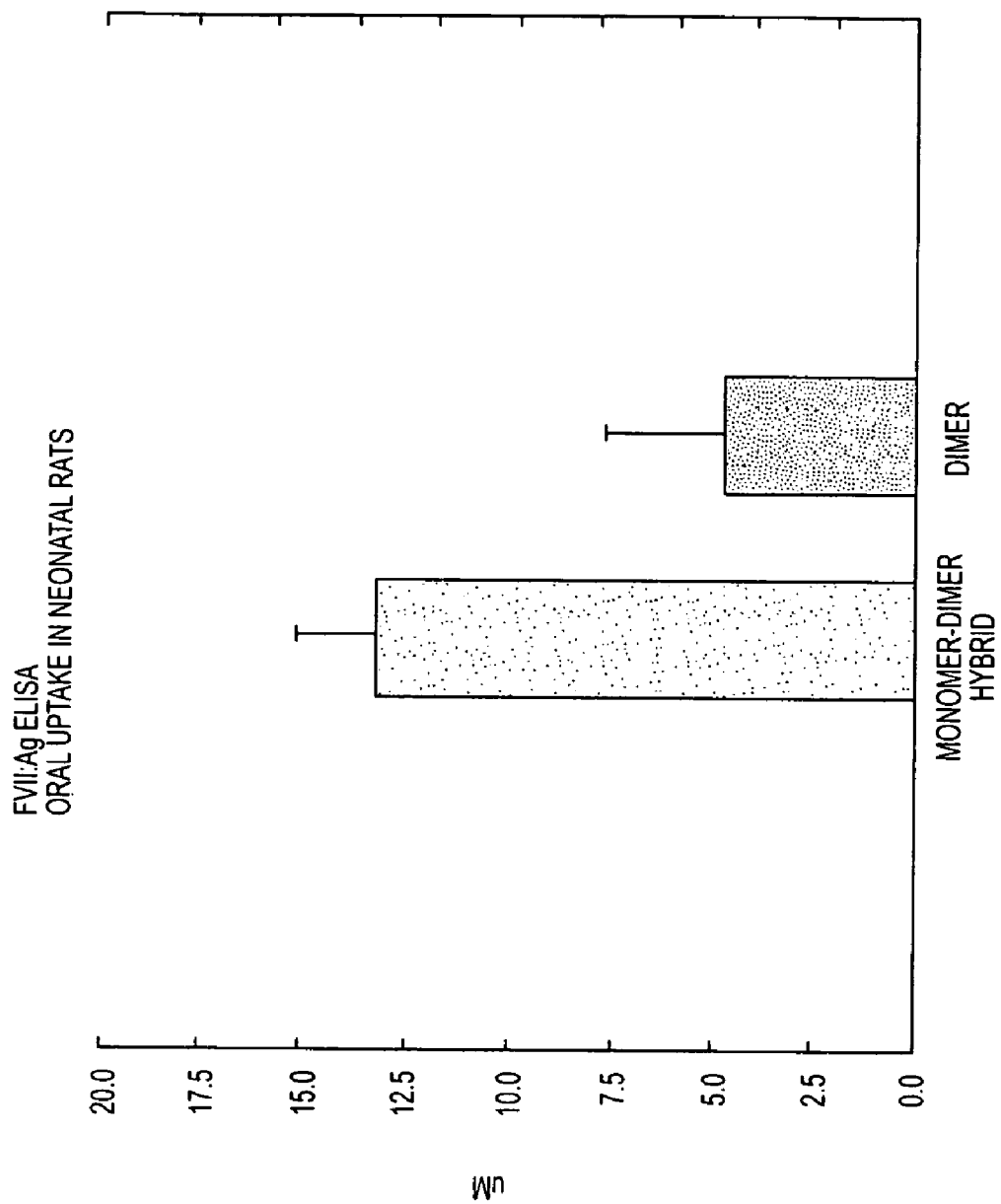
FIG. 8 compares oral dosing in neonatal rats of a chimeric monomer-dimer hybrid Factor VIIa-Fc (one Factor VII molecule) and a chimeric homodimer Factor VIIa-Fc (two Factor VII molecules).

FVIIa-Fc Oral Dosing in Day 10 Rats 25 gram day 9 newborn Sprague Dawley rats were purchased from Charles River (Wilmington, Mass.) and allowed to acclimate for 24 hours. The rats were dosed orally with FVIIaFc homodimer, monomer-dimer hybrid or a 50:50 mix of the two. A volume of 200 μl of a FVIIaFc solution for a dose of 1 mg/kg was administered. The solution was composed of a Tris-HCl buffer pH 7.4 with 5 mg/ml soybean trypsin inhibitor. The rats were euthanized with $CO_2$ at several time points, and 200 μl of blood was drawn by cardiac puncture. Plasma was obtained by the addition of a 3.8% sodium citrate solution and centrifugation at room temperature at a speed of 1268×g. The plasma samples were either assayed fresh or frozen at 20° C. Orally dosed monomer-dimer hybrid resulted in significantly higher maximum ($C_{max}$) serum concentrations compared to homodimeric Factor VII (FIG. 8).

Example 22

Factor IX-Fc Oral Dosing of Neonatal Rats

Ten-day old neonatal Sprague-Dawley rats were dosed p.o. with 200 μl of FIX-Fc homodimer or FIX-Fc: FlagFc monomer-dimer hybrid at approximately equimolar doses of 10 nmol/kg in 0.1 M sodium phosphate buffer, pH 6.5 containing 5 mg/ml soybean trypsin inhibitor and 0.9% NaCl. At 1, 2, 4, 8, 24, 48, and 72 hours post injection, animals were euthanized with $CO_2$, blood was drawn via cardiac puncture and plasma was obtained by the addition of a 3.8% sodium citrate solution and centrifugation at room temperature at a speed of 1268×g. Samples were then sedimented by centrifugation, serum collected and frozen at −20° C. until analysis of the fusion proteins by ELISA.

Example 23

Factor IX-Fc ELISA

Figure 9:
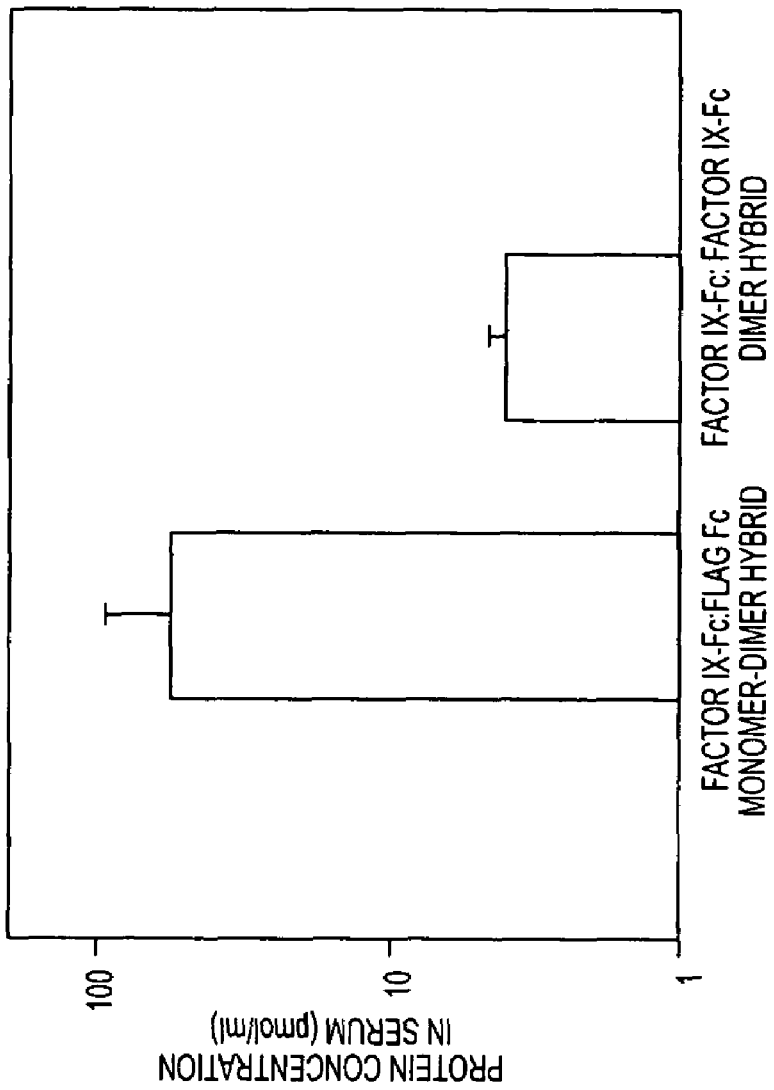
FIG. 9 compares oral dosing in neonatal rats of a chimeric monomer-dimer hybrid Factor IX-Fc (one Factor IX molecule) with a chimeric homodimer.
Figure 10:
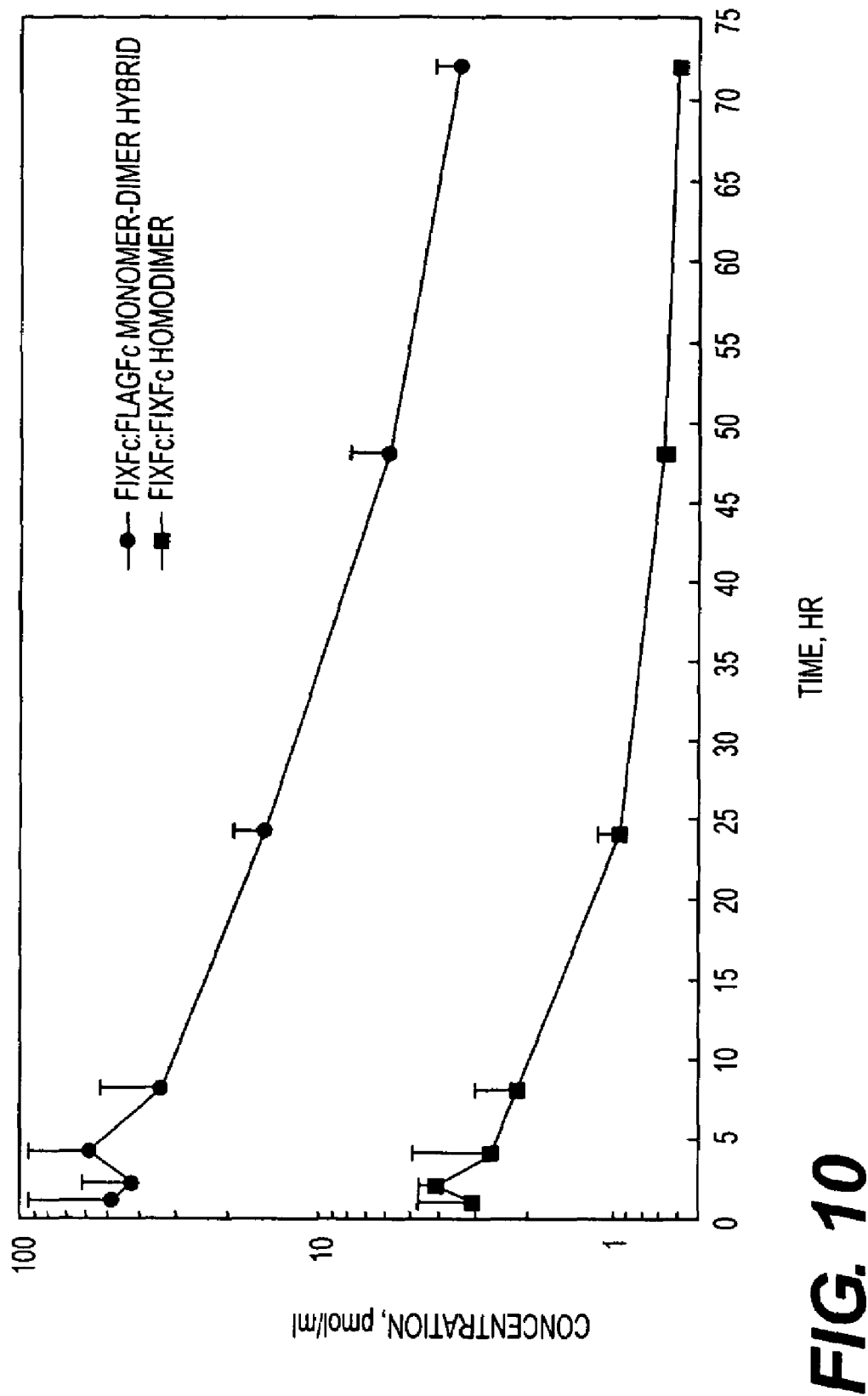
FIG. 10 is a time course study comparing a chimeric monomer-dimer hybrid Factor IX-Fc (one Factor IX molecule) administered orally to neonatal rats with an orally administered chimeric homodimer.

A 96-well Immulon 4HBX ELISA plate (Thermo LabSystems, Vantaa, Finland) was coated with 100 μl/well of goat anti-Factor IX IgG (Affinity Biologicals, Ancaster, Canada) diluted 1:100 in 50 mM carbonate buffer, pH 9.6. The plates were incubated at ambient temperature for 2 hours or overnight at 4° C. sealed with plastic film. The wells were washed 4 times with PBST, 300 μl/well using the TECAN plate washer. The wells were blocked with PBST+6% BSA, 200 μl/well, and incubated 90 minutes at ambient temperature. The wells were washed 4 times with PBST, 300 μl/well using the TECAN plate washer. Standards and blood samples from rats described in Example 18 were added to the wells, (100 μl/well), and incubated 90 minutes at ambient temperature. Samples and standards were diluted in HBET buffer (HBET: 5.95 g HEPES, 1.46 g NaCl, 0.93 g $Na_2$EDTA, 2.5 g Bovine Serum Albumin, 0.25 ml Tween-20, bring up to 250 ml with $dH_2O$, adjust pH to 7.2). Standard curve range was from 200 ng/ml to 0.78 ng/ml with 2 fold dilutions in between. Wells were washed 4 times with PBST, 300 μl/well using the TECAN plate washer. 100 μl/well of conjugated goat anti-human IgG-Fc-HARP antibody (Pierce, Rockford, Ill.) diluted in HBET 1:25,000 was added to each well. The plates were incubated 90 minutes at ambient temperature. The wells were washed 4 times with PBST, 300 μl/well using the TECAN plate washer. The plates were developed with 100 μl/well of tetramethylbenzidine peroxidase substrate (TMB) (Pierce, Rockford, Ill.) was added according to the manufacturer's instructions. The plates were incubated 5 minutes at ambient temperature in the dark or until color developed. The reaction was stopped with 100 μl/well of 2 M sulfuric acid. Absorbance was read at 450 nm on SpectraMax plusplate reader (Molecular Devices, Sunnyvale, Calif.). Analysis of blood drawn at 4 hours indicated more than a 10 fold difference in serum concentration between Factor IX-Fc monomer-dimer hybrids compared to Factor IX Fc homodimers (FIG. 9). The results indicated Factor IX-Fc monomer-dimer hybrid levels were consistently higher than Factor IX-Fc homodimers (FIG. 10).

Example 24

Cloning of Epo-Fc

The mature Epo coding region was obtained by PCR amplification from a plasmid encoding the mature erythropoietin coding sequence, originally obtained by RT-PCR from Hep G2 mRNA, and primers hepoxba-F and hepoeco-R, indicated below. Primer hepoxba-F contains an XbaI site, while primer hepoeco-R contains an EcoRI site. PCR was carried out in the Idaho Technology RapidCycler using Vent polymerase, denaturing at 95° C. for 15 seconds, followed by 28 cycles with a slope of 6.0 of 95° C. for 0 seconds, 55° C. for 0 seconds, and 72° C. for 1 minute 20 seconds, followed by 3 minute extension at 72° C. An approximately 514 bp product was gel purified, digested with XbaI and EcoRI, gel purified again and directionally subcloned into an XbaI/EcoRI-digested, gel purified pED.dC.XFc vector, mentioned above. This construct was named pED.dC.EpoFc.

The Epo sequence, containing both the endogenous signal peptide and the mature sequence, was obtained by PCR amplification using an adult kidney QUICK-clone cDNA preparation as the template and primers Epo+Pep-Sbf-F and Epo+Pep-Sbf-R, described below. The primer Epo+Pep-Sbf-F contains an SbfI site upstream of the start codon, while the primer Epo+Pep-Sbf-R anneals downstream of the endogenous SbfI site in the Epo sequence. The PCR reaction was carried out in the PTC-200 MJ Thermocycler using Expand polymerase, denaturing at 94° C. for 2 minutes, followed by 32 cycles of 94° C. for 30 seconds, 57° C. for 30 seconds, and 72° C. for 45 seconds, followed by a 10 minute extension at 72° C. An approximately 603 bp product was gel isolated and subcloned into the pGEM-T Easy vector. The correct coding sequence was excised by SbfI digestion, gel purified, and cloned into the PstI-digested, shrimp alkaline phosphatase (SAP)-treated, gel purified pED.dC.EpoFc plasmid. The plasmid with the insert in the correct orientation was initially determined by KpnI digestion. A XmnI and PvuII digestion of this construct was compared with pED.dC.EpoFc and confirmed to be in the correct orientation. The sequence was determined and the construct was named pED.dC.natEpoFc. PCR Primers:

```
hepoxba-F (EPO-F):
5'-AATCTAGAGCCCCACCACGCCTCATCTGTGA        (SEQ ID NO:75)
C-3' hepoeco-R (EPO-R)
5'-TTGAATTCTCTGTCCCCTGTCCTGCAGGCC-3'      (SEQ ID NO:76)

Epo + Pep-Sbf-F:
5'-GTACCTGCAGGCGGAGATGGGGGTGCA-3'         (SEQ ID NO:77)

Epo + Pep-Sbf-R:
5'-CCTGGTCATCTGTCCCCTGTCC-3'              (SEQ ID NO:78)
```

Example 25

Cloning of Epo-Fc

An alternative method of cloning EPO-Fc is described herein. Primers were first designed to amplify the full length Epo coding sequence, including the native signal sequence, as follows:

```
Epo-F:
5'-GTCCAACCTG CAGGAAGCTTG CCGCCACCAT GGGAGTGCAC   (SEQ ID NO:79)
GAATGTCCTG CCTGG- 3'

Epo-R:
5'-GCCGAATTCA GTTTTGTCGA CCGCAGCGG CGCCGGCGAA    (SEQ ID NO:80)
CTCTCTGTCC CCTGTTCTGC AGGCCTCC- 3'
```

The forward primer incorporates an SbfI and HindIII site upstream of a Kozak sequence, while the reverse primer removes the internal SbfI site, and adds an 8 amino acid linker to the 3' end of the coding sequence (EFAGAAAV) (SEQ ID NO: 31) as well as SalI and EcoRI restriction sites. The Epo coding sequence was then amplified from a kidney cDNA library (BD Biosciences Clontech, Palo Alto, Calif.) using 25 pmol of these primers in a 25 μl PCR reaction using Expand High Fidelity System (Boehringer Mannheim, Indianapolis, Ind.) according to manufacturer's standard protocol in a MJ Thermocycler using the following cycles: 94° C. 2 minutes; 30 cycles of (94° C. 30 seconds, 58° C. 30 seconds, 72° C. 45 seconds), followed by 72° C. for 10 minutes. The expected sized band (641 bp) was gel purified with a Gel Extraction kit (Qiagen, Valencia, Calif.) and ligated into the intermediate cloning vector pGEM T-Easy (Promega, Madison, Wis.). DNA was transformed into DH5α cells (Invitrogen, Carlsbad, Calif.) and miniprep cultures grown and purified with a Plasmid Miniprep Kit (Qiagen, Valencia, Calif.) both according to manufacturer's standard protocols. Once the sequence was confirmed, this insert was digested out with SbfI/EcoRI restriction enzymes, gel purified, and cloned into the PstI/EcoRI sites of the mammalian expression vector pED.dC in a similar manner.

Primers were designed to amplify the coding sequence for the constant region of human IgG1 (the Fc region, EU numbering 221-447) as follows:

```
Fc-F:
5'-GCTGCGGTCG ACAAAACTCA CACATGCCCA CCGTGCCCAG      (SEQ ID NO:82)

CTCCGGAACT CCTGGGCGGA CCGTCAGTC- 3'

Fc-R
5'-ATTGGAATTC TCATTTACCC GGAGACAGGG AGAGGC- 3'      (SEQ ID NO:83)
```

The forward primer incorporates a SalI site at the linker-Fc junction, as well as introducing BspEI and RsrII sites into the Fc region without affecting the coding sequence, while the reverse primer adds an EcoRI site after the stop codon. The Fc coding sequence was then amplified from a leukocyte cDNA library (BD Biosciences Clontech, Palo Alto, Calif.) using 25 pmol of these primers in a 25 µl PCR reaction using Expand High Fidelity System (Boehringer Mannheim, Indianapolis, Ind.) according to manufacturer's standard protocol in a MJ Thermocycler using the following cycles: 94° C. 2 minutes; 30 cycles of (94° C. 30 seconds, 58° C. 30 seconds, 72° C. 45 seconds), followed by 72° C. for 10 minutes. The expected sized band (696 bp) was gel purified with a Gel Extraction kit (Qiagen, Valencia, Calif.) and ligated into the intermediate cloning vector pGEM T-Easy (Promega, Madison, Wis.). DNA was transformed into DH5α cells (Invitrogen, Carlsbad, Calif.) and miniprep cultures grown and purified with a Plasmid Miniprep Kit (Qiagen, Valencia, Calif.), both according to manufacturer's standard protocols. Once the sequence was confirmed, this insert was digested out with Sal/EcoRI restriction enzymes, gel purified, and cloned into the SalI/EcoRI sites of the plasmid pED.dC.Epo (above) in a similar manner, to generate the mammalian expression plasmid pED.dC.EpoFc. In another experiment this plasmid was also digested with RsrII/XmaI, and the corresponding fragment from pSYN-Fc-002, which contains the Asn 297 Ala mutation (EU numbering) was cloned in to create pED.dC.EPO-Fc N297A (pSYN-EPO-004). Expression in mammalian cells was as described in Example 26. The amino acid sequence of EpoFc with an eight amino acid linker is provided in FIG. 2j. During the process of this alternative cloning method, although the exact EpoFc amino acid sequence was preserved (FIG. 2J), a number of non-coding changes were made at the nucleotide level (FIG. 3J). These are G6A (G at nucleotide 6 changed to A) (eliminate possible secondary structure in primer), G567A (removes endogenous SbfI site from Epo), A582G (removes EcoRI site from linker), A636T and T639G (adds unique BspEI site to Fc), and G651C (adds unique RsrII site to Fc). The nucleotide sequence in FIG. 3J is from the construct made in Example 25, which incorporates these differences from the sequence of the construct from Example 24.

Example 26

EPO-Fc Homodimer And Monomer-dimer Hybrid Expression And Purification

DG44 cells were plated in 100 mm tissue culture petri dishes and grown to a confluency of 50%-60%. A total of 10 µg of DNA was used to transfect one 100 mm dish: for the homodimer transfection, 10 µg of pED.dC.EPO-Fc; for the monomer-dimer hybrid transfection, 8 µg of pED.dC.EPO-Fc+2 µg of pcDNA3-FlagFc. The constructs used were cloned as described in Example 24. The cloning method described in Example 25 could also be used to obtain constructs for use in this example. The cells were transfected as described in the Superfect transfection reagent manual (Qiagen, Valencia, Calif.). Alternatively, pED.dC.EPO-Fc was cotransfected with pSYN-Fc-016 to make an untagged monomer. The media was removed from transfection after 48 hours and replaced with MEM Alpha without nucleosides plus 5% dialyzed fetal bovine serum for both transfections, while the monomer-dimer hybrid transfection was also supplemented with 0.2 mg/ml geneticin (Invitrogen, Carlsbad, Calif.). After 3 days, the cells were released from the plate with 0.25% trypsin and transferred into T25 tissue culture flasks, and the selection was continued for 10-14 days until the cells began to grow well as stable cell lines were established. Protein expression was subsequently amplified by the addition methotrexate.

For both cell lines, approximately $2 \times 10^7$ cells were used to inoculate 300 ml of growth medium in a 1700 $cm^2$ roller bottle (Corning, Corning, N.Y.). The roller bottles were incubated in a 5% $CO_2$ at 37° C. for approximately 72 hours. The growth medium was exchanged with 300 ml serum-free production medium (DMEM/F12 with 5 µg/ml bovine insulin and 10 µg/ml Gentamicin). The production medium (conditioned medium) was collected every day for 10 days and stored at 4° C. Fresh production medium was added to the roller bottles after each collection and the bottles were returned to the incubator. Prior to chromatography, the medium was clarified using a Supor Cap-100 (0.8/0.2 µm) filter from Pall Gelman Sciences (Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 137 mM NaCl), eluted with 0.1 M glycine, pH 2.7, and then neutralized with 1/10 volume of 1 M Tris-HCl, pH 9.0. Protein was then dialyzed into PBS.

The monomer-dimer hybrid transfection protein sample was subject to further purification, as it contained a mixture of EPO-Fc:EPO-Fc homodimer, EPO-Fc:Flag-Fc monomer-dimer hybrid, and Flag-Fc:Flag-Fc homodimer. Material was concentrated and applied to a 2.6 cm×60 cm (318 ml) Superdex 200 Prep Grade column at a flow rate of 4 ml/min (36 cm/hour) and then eluted with 3 column volumes of 1×PBS. Fractions corresponding to two peaks on the UV detector were collected and analyzed by SDS-PAGE. Fractions from the first peak contained either EPO-Fc:EPO-Fc homodimer or EPO-Fc:FlagFc monomer-dimer hybrid, while the second peak contained FlagFc:FlagFc homodimer. All fractions containing the monomer-dimer hybrid but no FlagFc homodimer were pooled and applied directly to a 1.6×5 cm M2 anti-FLAG sepharose column (Sigma Corp.) at a linear flow rate of 60 cm/hour. After loading the column was washed with 5 column volumes PBS. Monomer-dimer hybrids were then eluted with 100 mM Glycine, pH 3.0. Elution fractions containing the protein peak were then neutralized by adding 1/10 volume of 1 M Tris-HCl, and analyzed by reducing and non-reducing SDS-PAGE. Fractions were dialyzed into PBS, concentrated to 1-5 mg/ml, and stored at −80° C.

Alternatively, fractions from first peak of the Superdex 200 were analyzed by SDS-PAGE, and only fractions containing a majority of EpoFc monomer-dimer hybrid, with a minority of EpoFc homodimer, were pooled. This pool, enriched for the monomer-dimer hybrid, was then reapplied to a Superdex 200 column, and fractions containing only EpoFc monomer-dimer hybrid were then pooled, dialyzed and stored as purified protein. Note that this alternate purification method could be used to purify non-tagged monomer-dimer hybrids as well.

Example 27

Administration of EpoFc Dimer and Monomer-Dimer Hybrid With an Eight Amino Acid Linker to Cynomolgus Monkeys For pulmonary administration, aerosols of either EpoFc dimer or EpoFc monomer-dimer hybrid proteins (both with the 8 amino acid linker) in PBS, pH 7.4 were created with the Aeroneb Pro™ (AeroGen, Mountain View, Calif.) nebulizer, in-line with a Bird Mark 7A respirator, and administered to anesthetized naïve cynomolgus monkeys through endotracheal tubes (approximating normal tidal breathing). Both proteins were also administered to naïve cynomolgus monkeys by intravenous injection. Samples were taken at various time points, and the amount of Epo-containing protein in the resulting plasma was quantitated using the Quantikine IVD Human Epo Immunoassay (R&D Systems, Minneapolis, Minn.). Pharmacokinetic parameters were calculated using the software WinNonLin. Table 4 presents the bioavailability results of cynomolgus monkeys treated with EpoFc monomer-dimer hybrid or EpoFc dimer.

TABLE 4

ADMINISTRATION OF EPOFC MONOMER-DIMER HYBRID AND EPOFC DIMER TO MONKEYS

| Protein | Monkey # | Route | Approx. Deposited Dose[1] (μg/kg) | $C_{max}$ (ng/ml) | $C_{max}$ (fmol/ml) | $t_{1/2}$ (hr) | $t_{1/2}$ avg (hr) |
|---|---|---|---|---|---|---|---|
| EpoFc mono-mer-dimer hybrid | CO6181 | pulm | 20 | 72.3 | 1014 | 23.6 | 25.2 |
| | CO6214 | pulm | 20 | 50.1 | 703 | 23.5 | |
| | CO7300 | pulm | 20 | 120 | 1684 | 36.2 | |
| | CO7332 | pulm | 20 | 100 | 1403 | 17.5 | |
| | CO7285 | IV | 25 | 749 | 10508 | 21.3 | 22.6 |
| | CO7288 | IV | 25 | 566 | 7941 | 23 | |
| | CO7343 | IV | 25 | 551 | 1014 | 23.5 | |
| EpoFc dimer | DD026 | pulm | 15 | 10.7 | 120 | 11.5 | 22.1 |
| | DD062 | pulm | 15 | 21.8 | 244 | 27.3 | |
| | DD046 | pulm | 15 | 6.4 | 72 | 21.8 | |
| | DD015 | pulm | 15 | 12.8 | 143 | 20.9 | |
| | DD038 | pulm | 35 | 27 | 302 | 29 | |
| | F4921 | IV | 150 | 3701 | 41454 | 15.1 | 14.6 |
| | 96Z002 | IV | 150 | 3680 | 41219 | 15.3 | |
| | 1261CQ | IV | 150 | 2726 | 30533 | 23.6 | |
| | 127-107 | IV | 150 | 4230 | 47379 | 15.0 | |
| | 118-22 | IV | 150 | 4500 | 50403 | 8.7 | |
| | 126-60 | IV | 150 | 3531 | 39550 | 9.8 | |

[1]Based on 15% deposition fraction of nebulized dose as determined by gamma scintigraphy The percent bioavailability (F) was calculated for the pulmonary doses using the following equation:

$$F = (AUC\ \text{pulmonary}/\text{Dose pulmonary})/(AUC\ IV/\text{Dose}\ IV)*100$$

TABLE 5

CALCULATION OF PERCENT BIOAVAILABILITY FOR EPOFC MONOMER-DIMER HYBRID V. DIMER AFTER PULMONARY ADMINISTRATION TO NAÏVE CYNOMOLGUS MONKEYS

| Protein | Monkey # | Approx. Dose[1] (deposited) | AUC ng·hr/mL | Bioavailability[2] (F) | Average Bioavailability |
|---|---|---|---|---|---|
| EpoFc monomer-dimer hybrid | CO6181 | 20 μg/kg | 3810 | 25.2% | 34.9% |
| | CO6214 | 20 μg/kg | 3072 | 20.3% | |
| | CO7300 | 20 μg/kg | 9525 | 63.0% | |
| | CO7332 | 20 μg/kg | 4708 | 31.1% | |
| EpoFc dimer | DD026 | 15 μg/kg | 361 | 5.1% | 10.0% |
| | DD062 | 15 μg/kg | 1392 | 19.6% | |
| | DD046 | 15 μg/kg | 267 | 3.8% | |
| | DD015 | 15 μg/kg | 647 | 9.1% | |
| | DD038 | 35 μg/kg | 2062 | 12.4% | |

Figure 11:
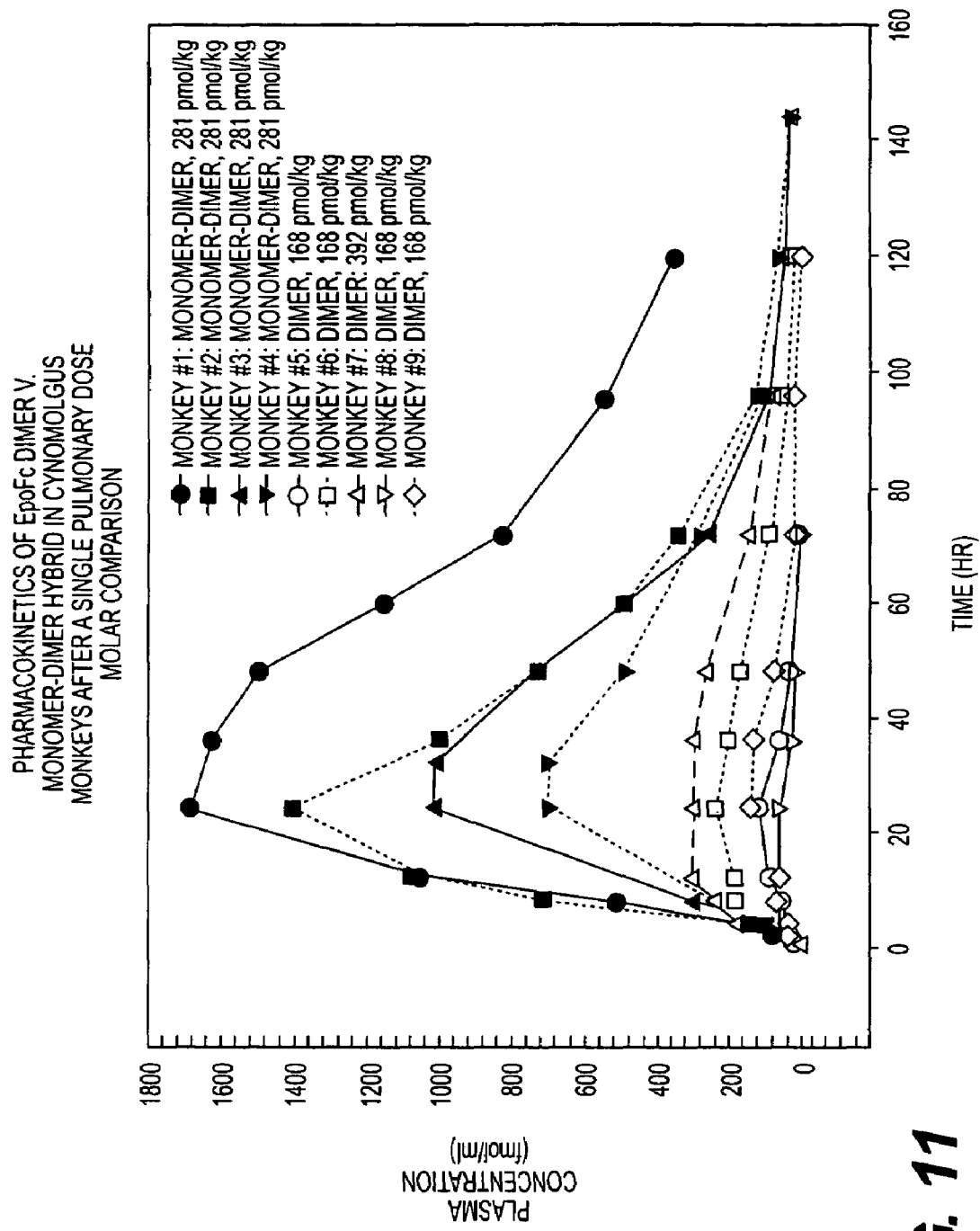
FIG. 11 demonstrates pharmokinetics of Epo-Fc dimer compared to Epo-Fc monomer-dimer hybrid in cynomolgus monkeys after a single pulmonary dose.

[1]Based on 15% deposition fraction of nebulized dose as determined by gamma scintigraphy
[2]Mean AUC for IV EpoFc monomer-dimer hybrid = 18,913 ng·hr/mL (n = 3 monkeys), dosed at 25 μg/kg. Mean AUC for IV EpoFc dimer = 70,967 ng·hr/mL (n = 6 monkeys), dosed at 150 μg/kg The pharmacokinetics of EpoFc with an 8 amino acid linker administered to cynomolgus monkeys is presented in FIG. 11. The figure compares the EpoFc dimer with the EpoFc monomer-dimer hybrid in monkeys after administration of a single pulmonary dose. Based on a molar comparison significantly higher serum levels were obtained in monkeys treated with the monomer-dimer hybrid compared to the dimer.

Example 28

Subcutaneous Administration of EPOFc Monomer-Dimer Hybrid

To compare serum concentrations of known erythropoietin agents with EPOFc monomer-dimer hybrids, both EPOFc monomer-dimer hybrid and Aranesp® (darbepoetin alfa), which is not a chimeric fusion protein, were administered subcutaneously to different monkeys and the serum concentration of both was measured over time.

Cynomolgus monkeys (n=3 per group) were injected subcutaneously with 0.025 mg/kg EpoFc monomer-dimer hybrid. Blood samples were collected predose and at times up to 144 hours post dose. Serum was prepared from the blood and stored frozen until analysis by ELISA (Human Epo Quantikine Immunoassay) (R & D Systems, Minneapolis, Minn.). Pharmacokinetic parameters were determined using WinNonLinâ® software (Pharsight, Mountainview, Calif.).

Figure 12:
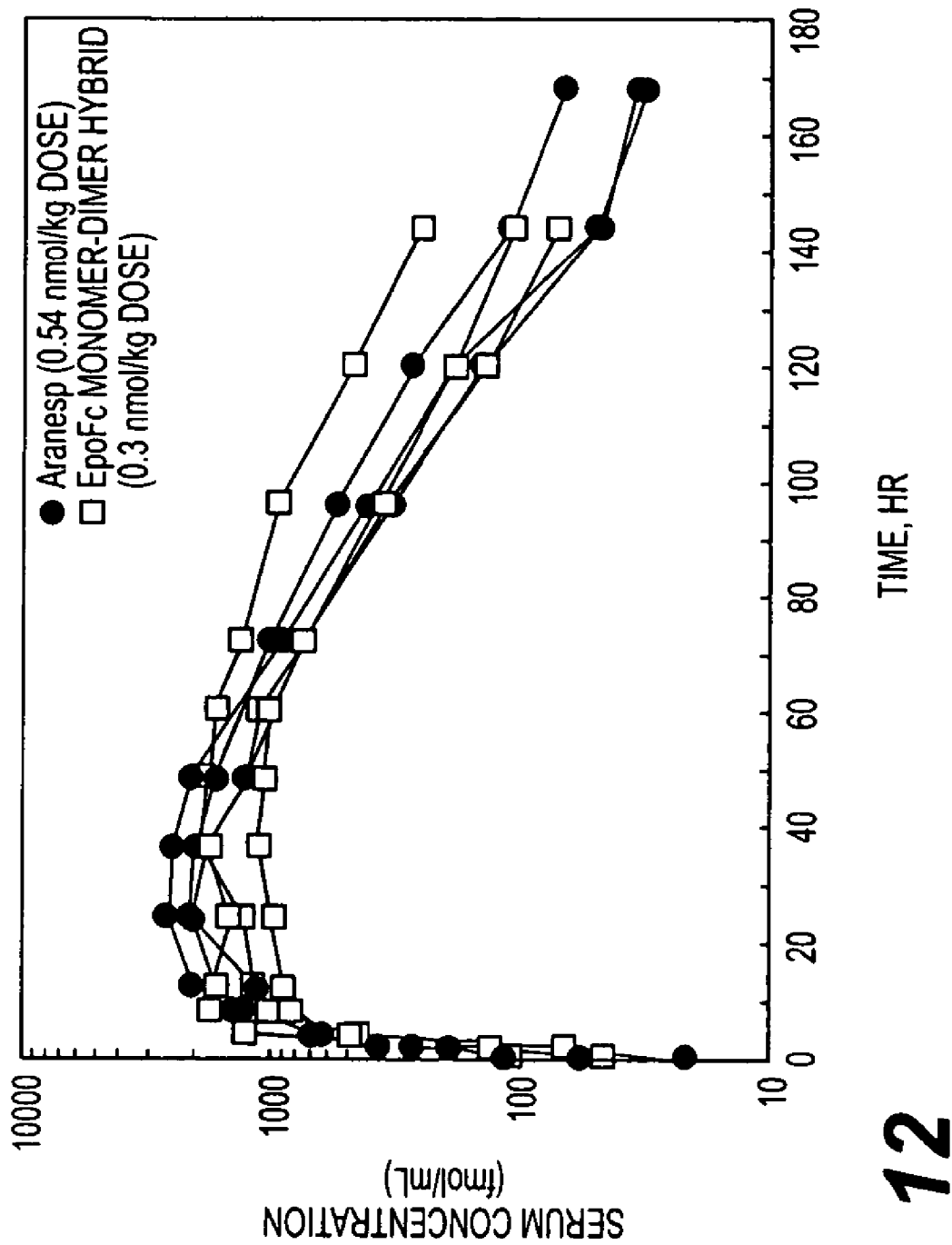
FIG. 12 compares serum concentration in monkeys of subcutaneously administered Epo-Fc monomer-dimer hybrid with subcutaneously administered Aranesp® (darbepoetin alfa).

The results indicated the serum concentrations of both EPOFc monomer-dimer hybrid and Aranesp® (darbepoetin alfa) were equivalent over time, even though the administered molar dose of Aranesp® (darbepoetin alfa) was slightly larger (Table 6) (FIG. 12).

TABLE 6

| | Route | Dose (μg/kg) | Dose (nmol/kg) | Cmax (ng/mL) | AUC (ng · hr · mL$^{-1}$) | T$_{1/2}$ (hr) | % Bioavailability (F) |
|---|---|---|---|---|---|---|---|
| EpoFc Monomer-dimer hybrid | Subcutaneous | 25 | 0.3 | 133 ± 34 | 10,745 ± 3,144 | 26 ± 5 | 57 ± 17 |
| Aranesp ® | Subcutaneous | 20 | 0.54 | 83 ± 11 | 5390 ± 747 | 22 ± 2 | 53 ± 8 |

Example 29

Intravenous Administration of EPOFc Monomer-dimer Hybrid

To compare serum concentrations of known erythropoietin agents with EPOFc monomer-dimer hybrids, EPOFc monomer-dimer hybrid, Aranesp® (darbepoetin alfa), and Epogen® (epoetin alfa), neither of which is a chimeric fusion protein, were administered intravenously to different monkeys and the serum concentration of both was measured over time.

Cynomolgus monkeys (n=3 per group) were injected intravenously with 0.025 mg/kg EpoFc monomer-dimer hybrid. Blood samples were collected predose and at times up to 144 hours post dose. Serum was prepared from the blood and stored frozen until analysis by ELISA (Human Epo Quantikine Immunoassay) (R & D Systems, Minneapolis, Minn.). Pharmacokinetic parameters were determined using WinNonLinâ software (Pharsight, Mountainview, Calif.).

Figure 13:
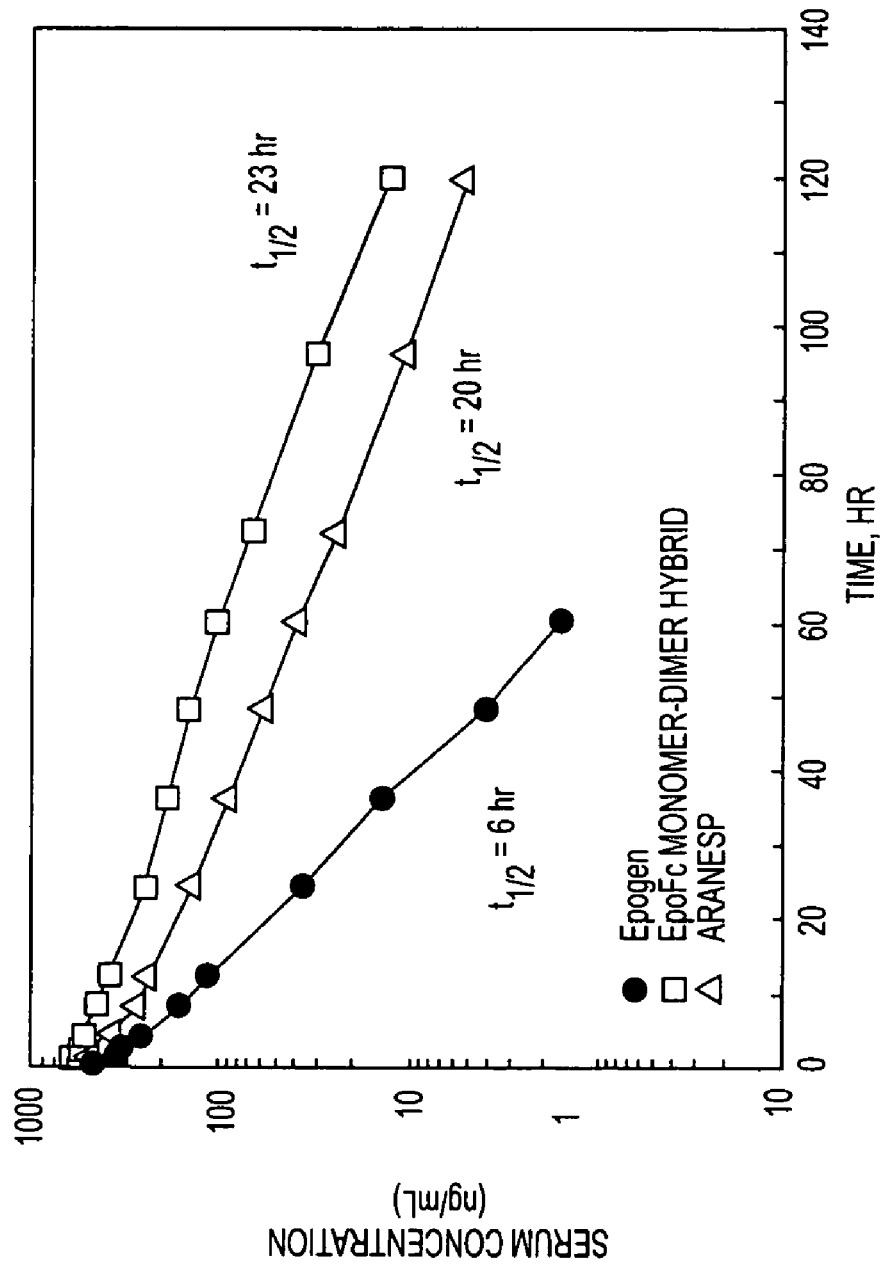
FIG. 13 compares serum concentration in monkeys of intravenously administered Epo-Fc monomer-dimer hybrid with intravenously administered Aranesp® (darbepoetin alfa) and Epogen® (epoetin alfa).

The results indicated the serum concentration versus time (AUC) of EPOFc monomer-dimer hybrid was greater than the concentrations of either Epogen® (epoetin alfa) or Aranesp® (darbepoetin alfa), even though the monkeys received larger molar doses of both Epogen® (epoetin alfa) and Aranesp® (darbepoetin alfa) (Table 7) (FIG. 13).

Example 30

Alternative Purification of EpoFc Monomer-dimer Hybrid

Figure 14:
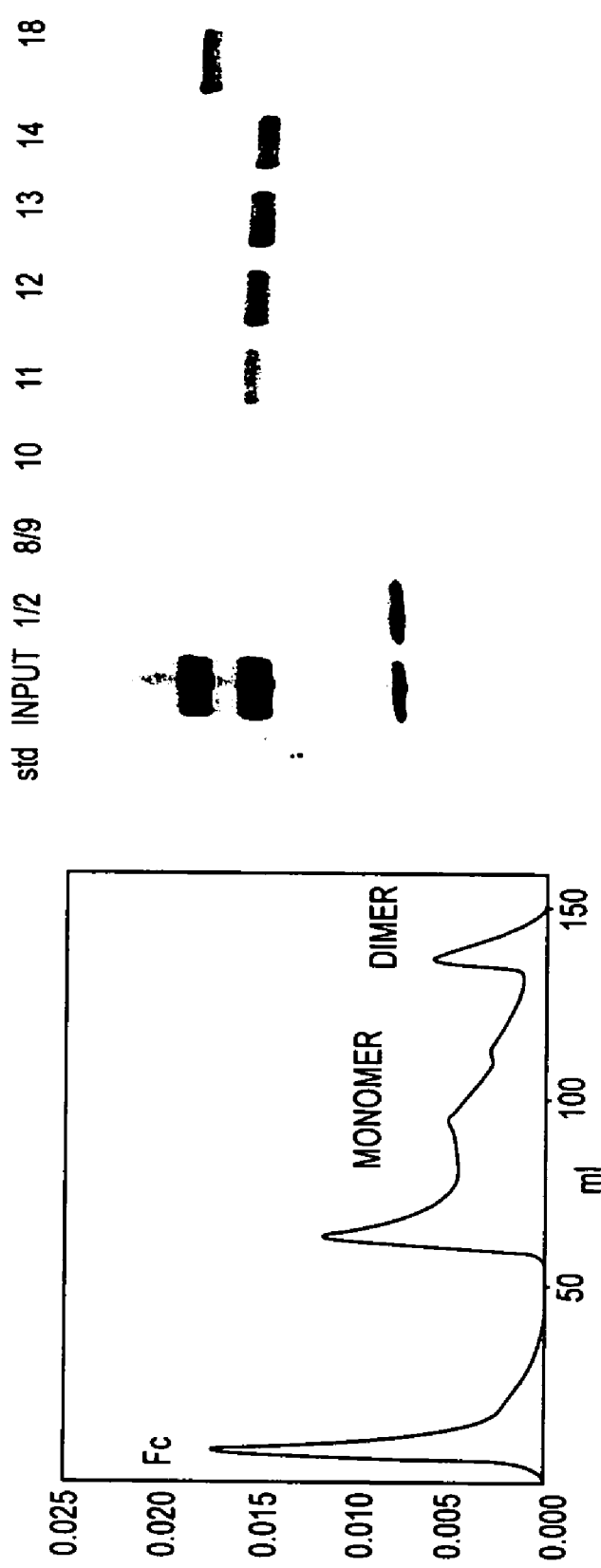
FIG. 14 shows a trace from a Mimetic Red 2™ column (ProMetic LifeSciences, Inc., Wayne, N.J.) and an SDS-PAGE of fractions from the column containing EpoFc monomer-dimer hybrid, EpoFc dimer, and Fc. EpoFc monomer-dimer hybrid is found in fractions 11, 12, 13, and 14. EpoFc dimer is found in fraction 18. Fc is found in fractions ½.

Yet another alternative for purifying EPO-Fc is described herein. A mixture containing Fc, EpoFc monomer-dimer hybrid, and EpoFc dimer was applied to a Protein A Sepharose column (Amersham, Uppsala, Sweden). The mixture was eluted according to the manufacturer's instructions. The Protein A Sepharose eluate, containing the mixture was buffer exchanged into 50 mM Tris-Cl (pH 8.0). The protein mixture was loaded onto an 8 mL Mimetic Red 2 XL column (ProMetic Life Sciences, Inc., Wayne, N.J.) that had been equilibrated in 50 mM Tris-Cl (pH 8.0). The column was then washed with 50 mM Tris-Cl (pH 8.0); 50 mM NaCl. This step removed the majority of the Fc. EpoFc monomer-dimer hybrid was specifically eluted from the column with 50 mM Tris-Cl (pH 8.0); 400 mM NaCl. EpoFc dimer can be eluted and the column regenerated with 5 column volumes of 1 M NaOH. Eluted fractions from the column were analyzed by SDS-PAGE (FIG. 14).

Example 31

Cloning of Igκ Signal Sequence-Fc Construct for Making Untagged Fc Alone

The coding sequence for the constant region of IgG1 (EU # 221-447; the Fc region) was obtained by PCR amplification from a leukocyte cDNA library (Clontech, Calif.) using the following primers:

TABLE 7

| | Route | Dose (μg/kg) | Dose (nmol/kg) | Cmax (ng/mL) | AUC (ng · hr · mL$^{-1}$) | T$_{1/2}$ (hr) |
|---|---|---|---|---|---|---|
| EpoFc Monomer-dimer hybrid | Intravenous | 25 | 0.3 | 622 ± 110 | 18,913 ± 3,022 | 23 ± 1 |
| Aranesp ® | Intravenous | 20 | 0.54 | 521 ± 8 | 10,219 ± 298 | 20 ± 1 |
| Epogen | Intravenous | 20 | 0.66 | 514 ± 172 | 3936 ± 636 | 6.3 ± 0.6 |

```
rcFc-F
5'- GCTGCGGTCGACAAAACTCACACATGCCCACCGTGCCCAGCTCC    (SEQ ID NO:82)

GGAACTCCTGGGCGGACCGTCAGTC -3' rcFc-R
5'- ATTGGAATTCTCATTTACCCGGAGACAGGGAGAGGC -3'        (SEQ ID NO:83)
```

The forward primer adds three amino acids (AAV) and a SalI cloning site before the beginning of the Fc region, and also incorporates a BspEI restriction site at amino acids 231-233 and an RsrII restriction site at amino acids 236-238 using the degeneracy of the genetic code to preserve the correct amino acid sequence (EU numbering). The reverse primer adds an EcoRI cloning site after the stop codon of the Fc. A 25 µl PCR reaction was carried out with 25 pmol of each primer using Expand High Fidelity System (Boehringer Mannheim, Indianapolis, Ind.) according to the manufacturer's standard protocol in a MJ Thermocycler using the following cycles: 94° C. 2 minutes; 30 cycles of (94° C. 30 seconds, 58° C. 30 seconds, 72° C. 45 seconds), 72° C. 10 minutes. The expected sized band (~696 bp) was gel purified with a Gel Extraction kit (Qiagen, Valencia Calif.), and cloned into pGEM T-Easy (Promega, Madison, Wis.) to produce an intermediate plasmid pSYN-Fc-001 (pGEM T-Easy/Fc).

The mouse Igκ signal sequence was added to the Fc CDS using the following primers:

```
rc-lgk sig seq-F:
5'-TTTAAGCTTGCCGCCACCATGGAGACAGACACACTCCTGCTATGGG  (SEQ ID NO:100)

TACTGCTGCTCTGGGTTCCAGGTTCCACTGGTGACAAAACTCACACATG

CCCACCG -3'

Fc-noXma-GS-R:
5'- GGTCAGCTCATCGCGGGATGGG -3'                     (SEQ ID NO:101)

Fc-noXma-GS-F:
5'- CCCATCCCGCGATGAGCTGACC -3'                     (SEQ ID NO:102)
```

The rc-Igκ signal sequence-F primer adds a HindIII restriction site to the 5' end of the molecule, followed by a Kozak sequence (GCCGCCACC) (SEQ ID NO: 103) followed by the signal sequence from the mouse Igκ light chain, directly abutted to the beginning of the Fc sequence (EU# 221). The Fc-noXma-GS-F and —R primers remove the internal XmaI site from the Fc coding sequence, using the degeneracy of the genetic code to preserve the correct amino acid sequence. Two 25 µl PCR reactions were carried out with 25 pmol of either rc-Igκ signal sequence-F and Fc-noXma-GS-R or Fc-noXma-GS-F and rcFc-R using Expand High Fidelity System (Boehringer Mannheim, Indianapolis, Ind.) according to the manufacturer's standard protocol in a MJ Thermocycler. The first reaction was carried out with 500 ng of leukocyte cDNA library (BD Biosciences Clontech, Palo Alto, Calif.) as a template using the following cycles: 94° C. 2 minutes; 30 cycles of (94° C. 30 seconds, 55° C. 30 seconds, 72° C. 45 seconds), 72° C. 10 minutes. The second reaction was carried out with 500 ng of pSYN-Fc-001 as a template (above) using the following cycles: 94° C. 2 minutes; 16 cycles of (94° C. 30 seconds, 58° C. 30 seconds, 72° C. 45 seconds), 72° C. 10 minutes. The expected sized bands (~495 and 299 bp, respectively) were gel purified with a Gel Extraction kit (Qiagen, Valencia Calif.), then combined in a PCR reaction with 25 pmol of rc-Igκ signal sequence-F and rcFc-R primers and run as before, annealing at 58° C. and continuing for 16 cycles. The expected sized band (~772 bp) was gel purified with a Gel Extraction kit (Qiagen, Valencia Calif.) and cloned into pGEM T-Easy (Promega, Madison, Wis.) to produce an intermediate plasmid pSYN-Fc-007 (pGEM T-Easy/Igκ sig seq-Fc). The entire Igκ signal sequence-Fc cassette was then subcloned using the HindIII and EcoRI sites into either the pEE6.4 (Lonza, Slough, UK) or pcDNA3.1 (Invitrogen, Carlsbad, Calif.) mammalian expression vector, depending on the system to be used, to generate pSYN-Fc-009 (pEE6.4/Igκ sig seq-Fc) and pSYN-Fc-015 (pcDNA3/Igκ sig seq-Fc).

Example 32

Cloning of Igκ Signal Sequence-Fc N297A Construct for Making untagged Fc N297A alone In order to mutate Asn 297 (EU numbering) of the Fc to an Ala residue, the following primers were used:

```
N297A-F
5'- GAGCAGTACGCTAGCACGTACCG -3'    (SEQ ID NO:104)

N297A-R
5'- GGTACGTGCTAGCGTACTGCTCC -3'    (SEQ ID NO:105)
```

Two PCR reactions were carried out with 25 pmol of either rc-Igκ signal sequence-F and N297A-R or N297A-F and rcFc-R using Expand High Fidelity System (Boehringer Mannheim, Indianapolis, Ind.) according to the manufacturer's standard protocol in a MJ Thermocycler. Both reactions were carried out using 500 ng of pSYN-Fc-007 as a template using the following cycles: 94° C. 2 minutes; 16 cycles of (94° C. 30 seconds, 48° C. 30 seconds, 72° C. 45 seconds), 72° C. 10 minutes. The expected sized bands (~319 and 475 bp, respectively) were gel purified with a Gel Extraction kit (Qiagen, Valencia Calif.), then combined in a PCR reaction with 25 pmol of rc-Igκ signal sequence-F and rcFc-R primers and run as before, annealing at 58° C. and continuing for 16 cycles. The expected sized band (~772 bp) was gel purified with a Gel Extraction kit (Qiagen, Valencia Calif.) and cloned into pGEM T-Easy (Promega, Madison, Wis.) to produce an intermediate plasmid pSYN-Fc-008 (pGEM T-Easy/Igκ sig seq-Fc N297A). The entire Igκ signal sequence-Fc alone cassette was then subcloned using the HindIII and EcoRI sites into either the pEE6.4 (Lonza, Slough, UK) or pcDNA3.1 (Invitrogen, Carlsbad, Calif.) mammalian expression vector, depending on the system to be used, to generate pSYN-Fc-010 (pEE6.4/Igκ sig seq-Fc N297A) and pSYN-Fc-016 (pcDNA3/Igκ sig seq-Fc N297A).

These same N297A primers were also used with rcFc-F and rcFc-R primers and pSYN-Fc-001 as a template in a PCR reaction followed by subcloning as indicated above to generate pSYN-Fc-002 (pGEM T Easy/Fc N297A).

Example 33

Cloning of EpoFc and Fc into Single Plasmid for Double Gene Vectors for Making EpoFc Wildtype or N297A Monomer-Dimer Hybrids, and Expression An alternative to transfecting the EpoFc and Fc constructs on separate plasmids is to clone them into a single plasmid, also called a double gene vector, such as used in the Lonza Biologics (Slough, UK) system. The RsrII/EcoRI fragment from pSYN-Fc-002 was subcloned into the corresponding sites in pEE12.4 (Lonza Biologics, Slough, UK) according to standard procedures to generate pSYN-Fc-006 (pEE12.4/Fc N297A fragment). The pSYN-EPO-004 plasmid was used as a template for a PCR reaction using Epo-F primer from Example 25 and the following primer:

```
EpoRsr-R:
5'- CTGACGGTCCGCCCAGGAGTTCCGGAGCTGGGCACGGTGGG  (SEQ ID NO:106)
CATG TGTGAGTTTTGTCGACCGCAGCGG -3'
```

A PCR reaction was carried out using Expand High Fidelity System (Boehringer Mannheim, Indianapolis, Ind.) according to the manufacturer's standard protocol in a MJ Thermocycler as indicated above, for 16 cycles with 55° C. annealing temperature. The expected sized band (~689 bp) was gel purified with a Gel Extraction kit (Qiagen, Valencia Calif.) and cloned into pSYN-Fc-006 using the HindIII/RsrII restriction sites, to generate pSYN-EPO-005 (pEE12.4/ EpoFc N297A). The double gene vector for the EpoFc N297A monomer-dimer hybrid was then constructed by cloning the NotI/BamHI fragment from pSYN-Fc-010 into the corresponding sites in pSYN-EPO-005 to generate pSYN-EPO-008 (pEE12.4-6.4/EpoFc N297A/Fc N297A).

The wild type construct was also made by subcloning the wild type Fc sequence from pSYN-Fc-001 into pSYN-EPO-005 using the RsrII and EcoRI sites, to generate pSYN-EPO-006 (pEE12.4/EpoFc). The double gene vector for the EpoFc monomer-dimer hybrid was then constructed by cloning the NotI/BamHI fragment from pSYN-Fc-009 into the corresponding sites in pSYN-EPO-006 to generate pSYN-EPO-007 (pEE12.4-6.4/EpoFc/Fc).

Each plasmid was transfected into CHOK1SV cells and positive clones identified and adpated to serum-free suspension, as indicated in the Lonza Biologics Manual for Standard Operating procedures (Lonza Biologics, Slough, UK), and purified as indicated for the other monomer-dimer constructs.

Example 34

Cloning of Human IFNβFc. IFNβ-Fc N297A with Eight Amino Acid Linkers and Igκ-Fc-6His Constructs (6×His Tag Disclosed as SEQ ID NO: 107)

10 ng of a human genomic DNA library from Clontech (BD Biosciences Clontech, Palo Alto, Calif.) was used as a template to isolate human IFNβ with its native signal sequence using the following primers:

```
IFNβ-F H3/SbfI:
5'- CTAGCCTGCAGGAAGCTTGCCGCCACCATGAC (SEQ ID NO:92)
CAACAAGTGTCTCCTC -3'

IFNβ-R (EFAG) Sal:
5'TTTGTCGACCGCAGCGGCGCCGGCGAACTCGTTT (SEQ ID NO:93)
CGGAGGTAACCTGTAAG -3'
```

The reverse primer was also used to create an eight amino acid linker sequence (EFAGAAAV) (SEQ ID NO: 31) on the 3' end of the human IFNβ sequence. The PCR reaction was carried out using the Expand High Fidelity System (Boehringer Mannheim, Indianapolis, Ind.) according to the manufacturer's standard protocol in a Rapid Cycler thermocycler (Idaho Technology, Salt Lake City, Utah). A PCR product of the correct size (~607 bp) was gel purified using a Gel Extraction kit (Qiagen; Valencia, Calif.), cloned into TA cloning vector (Promega, Madison, Wis.) and sequenced. This construct was named pSYN-IFNβ-002. pSYN-IFNβ-002 was digested with SbfI and SalI and cloned into pSP72 (Promega) at PstI and SalI sites to give pSYN-IFNβ-005.

Purified pSYN-Fc-001 (0.6 μg) was digested with SalI and EcoRI and cloned into the corresponding sites of pSYN-IFNβ-005 to create the plasmid pSYN-IFNβ-006 which contains human IFNβ linked to human Fc through an eight amino acid linker sequence. pSYN-IFNβ-006 was then digested with SbfI and EcoRI and the full-length IFNβ-Fc sequence cloned into the PstI and EcoRI sites of pEDdC.sig to create plasmid pSYN-IFNβ-008.

pSYN-Fc-002 containing the human Fc DNA with a single amino acid change from asparagine to alanine at position 297 (N297A; EU numbering) was digested with BspEI and XmaI to isolate a DNA fragment of ~365 bp containing the N297A mutation. This DNA fragment was cloned into the corresponding sites in pSYN-IFNβ-008 to create plasmid pSYN-IFNβ-009 that contains the IFNβ-Fc sequence with an eight amino acid linker and an N297A mutation in Fc in the expression vector, pED.dC.

Cloning of Igκ signal sequence-Fc N297A-6H is (SEQ ID NO: 107). The following primers were used to add a 6×His tag (SEQ ID NO: 107) to the C terminus of the Fc N297A coding sequence:

```
Fc GS-F:
5'- GGCAAGCTTGCCGCCACCATGGAGACAGACACACTCC -3'                              (SEQ ID NO:94)

Fc.6His-R:
5'- TCAGTGGTGATGGTGATGATGTTTACCCGGAGACAGGGAG -3'                          (SEQ ID NO:95)

Fc.6His-F (6xHis tag disclosed as SEQ ID NO:107):
5'- GGTAAACATCATCACCATCACCACTGAGAATTCC AATATCACTAGTGAATTCG -3'            (SEQ ID NO:96)

Sp6+T-R:
5'- GCTATTTAGGTGACACTATAGAATACTCAAGC -3'                                  (SEQ ID NO:97)
```

Two PCR reactions were carried out with 50 pmol of either Fc GS-F and Fc.6His-R (6×His tag disclosed as SEQ ID NO: 107) or Fc.6His-F (6×His tag disclosed as SEQ ID NO: 107) and Sp6+T-R using the Expand High Fidelity System (Boehringer Mannheim, Indianapolis, Ind.) according to the manufacturer's standard protocol in a MJ Thermocycler. Both reactions were carried out using 500 ng of pSYN-Fc-008 as a template in a 50 µl reaction, using standard cycling conditions. The expected sized bands (~780 and 138 bp, respectively) were gel purified with a Gel Extraction kit (Qiagen, Valencia Calif.), then combined in a 50 µl PCR reaction with 50 pmol of Fc GS-F and Sp6+T-R primers and run as before, using standard cycling conditions. The expected sized band (~891 bp) was gel purified with a Gel Extraction kit (Qiagen, Valencia Calif.) and cloned into pcDNA6 V5-His B using the HindIII and EcoRI sites to generate pSYN-Fc-014 (pcDNA6/Igκ sig seq-Fc N297A-6 His).

Example 35

Expression and Purification of IFNβFc. IFNβ-Fc N297A Homodimer and IFNβ-Fc N297A Monomer-Dimer Hybrid CHO DG44 cells were plated in 100 mm tissue culture dishes and grown to a confluency of 50%-60%. A total of 10 µg of DNA was used to transfect a single 100 mm dish. For the homodimer transfection, 10 µg of the pSYN-FNβ-008 or pSYN-IFNβ-009 construct was used; for the monomer-dimer hybrid transfection, 8 µg of the pSYN-IFNβ-009+2 µg of pSYN-Fc-014 construct was used. The cells were transfected using Superfect transfection reagents (Qiagen, Valencia, Calif.) according to the manufacturer's instructions. 48 to 72 hours post-transfection, growth medium was removed and cells were released from the plates with 0.25% trypsin and transferred to T75 tissue culture flasks in selection medium (MEM Alpha without nucleosides plus 5% dialyzed fetal bovine serum). The selection medium for the monomer-dimer hybrid transfection was supplemented with 5 µg/ml Blasticidin (Invitrogen, Carlsbad, Calif.). Selection was continued for 10-14 days until the cells began to grow well and stable cell lines were established. Protein expression was subsequently amplified by the addition methotrexate: ranging from 10 to 50 nM.

For all cell lines, approximately 2×10⁷ cells were used to inoculate 300 ml of growth medium in a 1700 cm² roller bottle (Corning, Corning, N.Y.). The roller bottles were incubated in a 5% CO₂ incubator at 37° C. for approximately 72 hours. The growth medium was then exchanged with 300 ml serum-free production medium (DMEM/F12 with 5 µg/ml human insulin). The production medium (conditioned medium) was collected every day for 10 days and stored at 4° C. Fresh production medium was added to the roller bottles after each collection and the bottles were returned to the incubator. Prior to chromatography, the medium was clarified using a Supor Cap-100 (0.8/0.2 µm) filter from Pall Gelman Sciences (Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 137 mM NaCl), eluted with 0.1 M glycine, pH 2.7, and then neutralized with 1/10 volume of 1 M Tris-HCl pH 8.0, 5 M NaCl. The homodimer proteins were further purified over a Superdex 200 Prep Grade sizing column run and eluted in 50 mM sodium phosphate pH 7.5, 500 mM NaCl, 10% glycerol.

The monomer-dimer hybrid protein was subject to further purification since it contained a mixture of IFNβFc N297A: IFNβPFc N297A homodimer, IFNβFc N297A: Fc N297A His monomer-dimer hybrid, and Fc N297A His: Fc N297A His homodimer. Material was applied to a Nickel chelating column in 50 mM sodium phosphate pH 7.5, 500 mM NaCl. After loading, the column was washed with 50 mM imidazole in 50 mM sodium phosphate pH 7.5, 500 mM NaCl and protein was eluted with a gradient of 50-500 mM imidazole in 50 mM sodium phosphate pH 7.5, 500 mM NaCl. Fractions corresponding to elution peaks on a UV detector were collected and analyzed by SDS-PAGE. Fractions from the first peak contained IFNβPFc N297A: Fc N297A His monomer-dimer hybrid, while the second peak contained Fc N297A His: Fc N297A His homodimer. All fractions containing the monomer-dimer hybrid, but no Fc homodimer, were pooled and applied directly to a Superdex 200 Prep Grade sizing column, run and eluted in 50 mM sodium phosphate pH 7.5, 500 mM NaCl, 10% glycerol. Fractions containing IFNβ-Fc N297A:Fc N297A His monomer-dimer hybrids were pooled and stored at −80° C.

Example 36

Antiviral Assay for IFNβ Activity

Antiviral activity (IU/ml) of IFNβ fusion proteins was determined using a CPE (cytopathic effect) assay. A549 cells were plated in a 96 well tissue culture plate in growth media (RPMI 1640 supplemented with 10% fetal bovine serum (FBS) and 2 mM L-glutamine) for 2 hours at 37° C., 5% CO₂. IFNβ standards and IFNβ fusion proteins were diluted in growth media and added to cells in triplicate for 20 hours at 37° C., 5% CO₂. Following incubation, all media was removed from wells, encephalomyocarditis virus (EMCV) was diluted in growth media and added (3000 pfu/well) to each well with the exception of control wells. Plates were incubated at 37° C., 5% CO₂ for 28 hours. Living cells were fixed with 10% cold trichloroacetic acid (TCA) and then stained with Sulforhodamine B (SRB) according to published protocols (Rubinstein et al. 1990, *J. Natl. Cancer Inst.* 82, 1113). The SRB dye was solubilized with 10 mM Tris pH 10.5 and read on a spectrophotometer at 490 nm. Samples were analyzed by comparing activities to a known standard curve ranging from 10 to 0.199 IU/ml. The results are presented below in Table 8 and demonstrate increased antiviral activity of monomer-dimer hybrids.

TABLE 8

INTERFERON BETA ANTIVIRAL ASSAY
HOMODIMER V. MONOMER-DIMER HYBRID

| Protein | Antiviral Activity (IU/nmol) | Std dev |
|---|---|---|
| IFNβ-Fc 8aa linker homodimer | $4.5 \times 10^5$ | $0.72 \times 10^5$ |
| IFNβFc N297A 8aa linker homodimer | $3.21 \times 10^5$ | $0.48 \times 10^5$ |
| IFNβFc N297A 8aa linker: Fc His monomer-dimer hybrid | $12.2 \times 10^5$ | $2 \times 10^5$ |

Example 37

Administration of IFNβFc Homodimer and Monomer-Dimer Hybrid With an Eight Amino Acid Linker to Cynomolgus Monkeys For pulmonary administration, aerosols of either IFNβFc homodimer or IFNβFc N297A monomer-dimer hybrid proteins (both with the 8 amino acid linker) in PBS, pH 7.4, 0.25% HSA were created with the Aeroneb Pro™ (AeroGen, Mountain View, Calif.) nebulizer, in-line with a Bird Mark 7A respirator, and administered to anesthetized naïve cynomolgus monkeys through endotracheal tubes (approximating normal tidal breathing). Blood samples were taken at various time points, and the amount of IFNβ-containing protein in the resulting serum was quantitated using a human IFNβ Immunoassay (Biosource International, Camarillo, Calif.). Pharmacokinetic parameters were calculated using the software WinNonLin. Table 9 presents the results of cynomolgus monkeys treated with IFNβ Fc N297A monomer-dimer hybrid or IFNβ Fc homodimer.

TABLE 9

ADMINISTRATION OF IFNβFC N297A MONOMER-DIMER
HYBRID AND IFNβFC HOMODIMER TO MONKEYS

| Protein | Monkey # | Route | Approx. Deposited Dose[1] (μg/kg) | $C_{max}$ (ng/ml) | AUC (hr * ng/ml) | $t_{1/2}$ (hr) | $t_{1/2}$ avg (hr) |
|---|---|---|---|---|---|---|---|
| IFNβFc N297A monomer-dimer hybrid | CO7308 | pulm | 20 | 23.3 | 987.9 | 27.6 | 27.1 |
| | CO7336 | pulm | 20 | 22.4 | 970.6 | 25.6 | |
| | CO7312 | pulm | 20 | 21.2 | 1002.7 | 28.0 | |
| IFNβFc homodimer | CO7326 | pulm | 20 | 2.6 | 94.6 | 11.1 | 11.4 |
| | CO7338 | pulm | 20 | 5.0 | 150.6 | 11.7 | |

Figure 15:
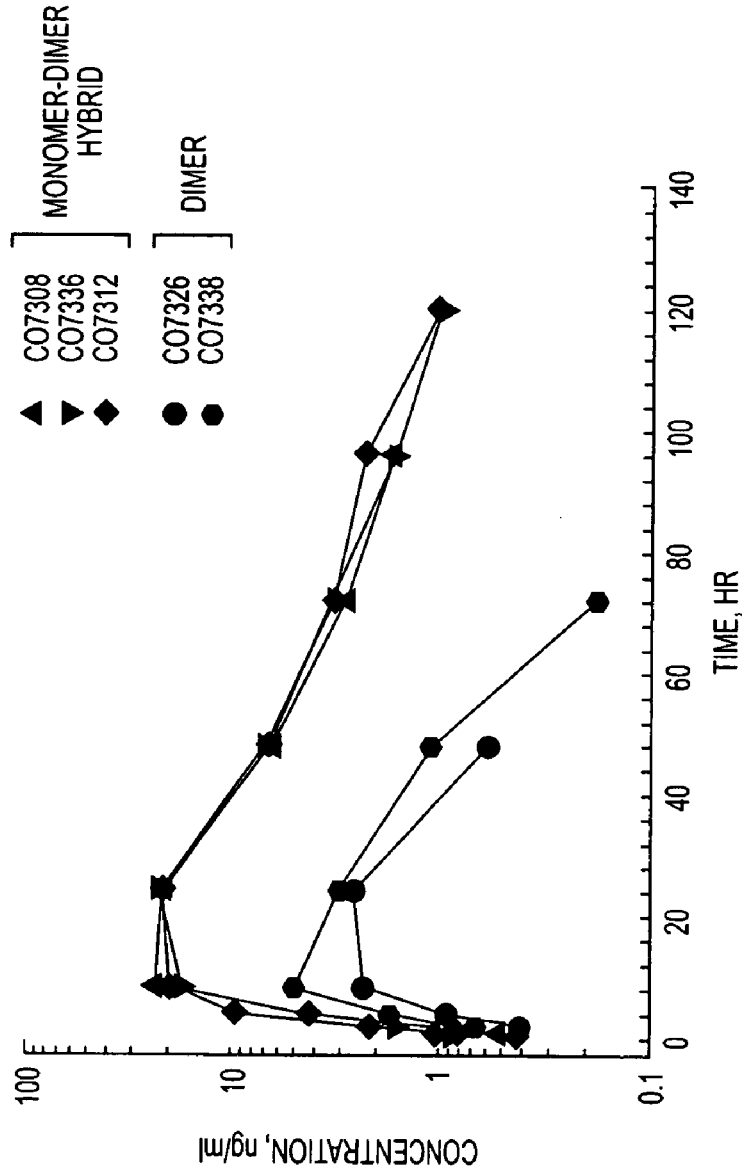
FIG. 15 shows the pharmacokinetics of IFNβFc with an 8 amino acid linker in cynomolgus monkeys after a single pulmonary dose.

[1]Based on 15% deposition fraction of nebulized dose as determined by gamma scintigraphy The pharmacokinetics of IFNβFc with an 8 amino acid linker administered to cynomolgus monkeys is presented in FIG. 15. The figure compares the IFNβFc homodimer with the IFNβPFc N297A monomer-dimer hybrid in monkeys after administration of a single pulmonary dose. Significantly higher serum levels were obtained in monkeys treated with the monomer-dimer hybrid compared to the homodimer.

Figure 16:
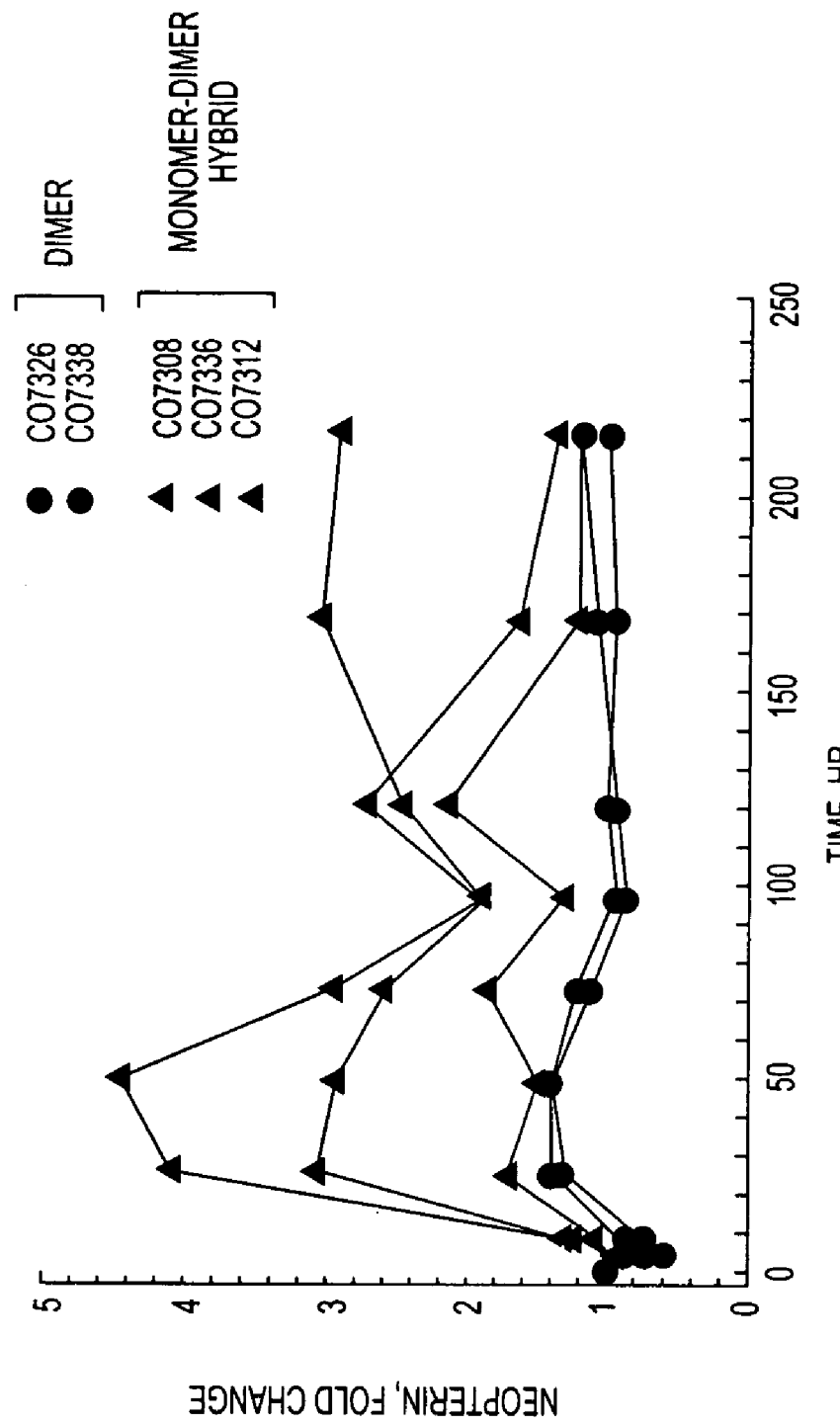
FIG. 16 shows neopterin stimulation in response to the IFNβ-Fc homodimer and the IFNβ-Fc N297A monomer-dimer hybrid in cynomolgus monkeys.

Serum samples were also analyzed for neopterin levels (a biomarker of IFNβ activity) using a neopterin immunoassay (MP Biomedicals, Orangeburg, N.Y.). The results for this analysis are shown in FIG. 16. The figure compares neopterin stimulation in response to the IFNβ-Fc homodimer and the IFNβ-Fc N297A monomer-dimer hybrid. It can be seen that significantly higher neopterin levels were detected in monkeys treated with IFNβ-Fc N297A monomer-dimer hybrid as compared to the IFNβ-Fc homodimer.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. An isolated monomer-dimer hybrid immunoconjugate comprising $$X-L_a-F_1:F_2 \text{ or } F_2:F_1-L_a-X$$

wherein
X is a single biologically active molecule,
L is a linker,
a is any integer or zero,
: represents a chemical association,
$F_1$ is at least a portion of an immunoglobulin constant region comprising an FcRn binding site and does not comprise a biologically active molecule, and
$F_2$ is at least a portion of an immunoglobulin constant region comprising an FcRn binding site and does not comprise a biologically active molecule or immunoglobulin variable region.

2. The monomer-dimer hybrid immunoconjugate of claim 1, wherein $F_2$ further comprises an affinity tag.

3. The protein of claim 2, wherein the affinity tag is a FLAG tag or His tag.

4. An isolated monomer-dimer hybrid immunoconjugate of the formula $$X-L_a-F_1:F_2-T \text{ or } T-F_2:F_1-L_a-X$$

wherein
X is a single biologically active molecule,
L is a linker,
a is any integer or zero,
T is a molecule having a molecular weight less than 2 kD,
: represents a chemical association,
$F_1$ is an immunoglobulin constant region or portion thereof comprising an FcRn binding site, and
$F_2$ is at least a portion of an immunoglobulin constant region comprising an FcRn binding site.

5. The monomer-dimer hybrid immunoconjugate of claim 4, wherein T is attached to the C terminus of $F_2$.

6. The monomer-dimer hybrid immunoconjugate of claim 4, wherein T is attached to the N terminus of $F_2$.

7. The monomer-dimer hybrid immunoconjugate of claim 4, wherein T is an affinity tag.

8. The monomer-dimer hybrid immunoconjugate of claim 7, wherein the affinity tag is a FLAG tag or His tag.

9. The monomer-dimer hybrid immunoconjugate of claim 1 or 4, wherein $F_1$ and $F_2$ are Fc fragments.

10. The monomer-dimer hybrid immunoconjugate of claim 1 or 4, wherein the immunoglobulin is IgG.

11. The monomer-dimer hybrid immunoconjugate of claim 10, wherein the IgG is an IgG1 or an IgG2.

12. The monomer-dimer hybrid immunoconjugate of claim 1 or 4, wherein X is a polypeptide.

13. The monomer-dimer hybrid immunoconjugate of claim 12, wherein X is a protein.

14. The monomer-dimer hybrid immunoconjugate of claim 13, wherein the protein is a clotting factor.

15. The monomer-dimer hybrid immunoconjugate of claim 14, wherein the clotting factor is Factor IX.

16. The monomer-dimer hybrid immunoconjugate of claim 14, wherein the clotting factor is Factor VIII.

17. The monomer-dimer hybrid immunoconjugate of claim 14, wherein the clotting factor is Factor VII or VIIa.

18. The monomer-dimer hybrid immunoconjugate of claim 13, wherein the protein is follicle stimulating hormone (FSH).

19. The monomer-dimer hybrid immunoconjugate of claim 13, wherein the protein is interferon.

20. The monomer-dimer hybrid immunoconjugate of claim 19, wherein the protein is interferon α.

21. The monomer-dimer hybrid immunoconjugate of claim 20, wherein $L_a$ consists of 15-25 amino acids.

22. The monomer-dimer hybrid immunoconjugate of claim 20, wherein $L_a$ consists of 15-20 amino acids.

23. The monomer-dimer hybrid immunoconjugate of claim 19, wherein the protein is interferon β.

24. The monomer-dimer hybrid immunoconjugate of claim 13, wherein the protein is a growth factor.

25. The monomer-dimer hybrid immunoconjugate of claim 24, wherein the growth factor is erythropoietin.

26. The monomer-dimer hybrid immunoconjugate of claim 12, wherein X is a peptide.

27. The monomer-dimer hybrid immunoconjugate of claim 26, wherein the peptide is a viral fusion inhibitor.

28. The monomer-dimer hybrid immunoconjugate of claim 27, wherein the viral fusion inhibitor is an HIV fusion inhibitor.

29. The monomer-dimer hybrid immunoconjugate of claim 28, wherein the HIV fusion inhibitor is T20 (SEQ ID NO:1), T21 (SEQ ID NO:2), or T1249 (SEQ ID NO:3).

30. The monomer-dimer hybrid immunoconjugate of claim 26, wherein the peptide is leuprolide.

31. The monomer-dimer hybrid immunoconjugate of claim 1 or 4, wherein X is a small molecule.

32. The monomer-dimer hybrid immunoconjugate of claim 31, wherein the small molecule is a VLA4 antagonist.

33. The monomer-dimer hybrid immunoconjugate of claim 1 or 4, wherein X is a nucleic acid.

34. The monomer-dimer hybrid immunoconjugate of claim 33, wherein the nucleic acid is DNA.

35. The monomer-dimer hybrid immunoconjugate of claim 33, wherein the nucleic acid is RNA.

36. The monomer-dimer hybrid immunoconjugate of claim 33, wherein the nucleic acid is an antisense molecule.

37. The monomer-dimer hybrid immunoconjugate of claim 33, wherein the nucleic acid is a ribozyme.

38. The monomer-dimer hybrid immunoconjugate of claim 1 or 4, wherein the chemical association between $F_1$ and $F_2$ is a non-covalent interaction.

39. The monomer-dimer hybrid immunoconjugate of claim 1 or 4, wherein the chemical association between $F_1$ and $F_2$ is a covalent bond.

40. The monomer-dimer hybrid immunoconjugate of claim 1 or 4, wherein the chemical association between $F_1$ and $F_2$ is a disulfide bond.

41. The monomer-dimer hybrid immunoconjugate of claim 1 or 4, wherein the chemical association between $F_1$ and $F_2$ is not a disulfide bond.

42. An isolated monomer-dimer hybrid immunoconjugate of the formula $$X\text{-}L_a\text{-}F_1\text{:}F_2 \text{ or } F_2\text{:}F_1\text{-}L_a\text{-}X$$

wherein
X is erythropoietin,
L is a linker,
a is any integer or zero,
: represents a chemical association,
$F_1$ is an immunoglobulin constant region or portion thereof comprising an FcRn binding site; and
$F_2$ is at least a portion of an immunoglobulin constant region comprising an FcRn binding site.

43. The protein monomer-dimer hybrid immunoconjugate of claim 42, wherein L is an eight amino acid linker having the amino acid sequence EFAGAAAV (SEQ ID NO:31).

44. The of claim 42, wherein F1 and F2 are Fc fragments having a mutation of asparagine to alanine at position 297.

45. An isolated monomer-dimer hybrid immunoconjugate of the formula $$X\text{-}L_a\text{-}F_1\text{:}F_2 \text{ or } F_2\text{:}F_1\text{-}L_a\text{-}X$$

wherein
X is IFNβ,
L is a linker,
a is any integer or zero,
: represents a chemical association,
$F_1$ is an immunoglobulin constant region or portion thereof comprising an FcRn binding site; and
$F_2$ is at least a portion of an immunoglobulin constant region comprising an FcRn binding site.

46. The monomer-dimer hybrid immunoconjugate of claim 45, wherein $F_1$ and $F_2$ are Fc fragments having a mutation of asparagine to alanine at position 297.

47. An isolated monomer-dimer hybrid immunoconjugate of the formula $$X\text{-}L_a\text{-}F_1\text{:}F_2 \text{ or } F_2\text{:}F_1\text{-}L_a\text{-}X$$

wherein
X is Factor IX,
L is a linker,
a is any integer or zero,
: represents a chemical association,
$F_1$ is an immunoglobulin constant region or portion thereof comprising an FcRn binding site; and
$F_2$ is at least a portion of an immunoglobulin constant region comprising an FcRn binding site.

48. The monomer-dimer hybrid immunoconjugate of claim 47, wherein $F_1$ and $F_2$ are Fc fragments having a mutation of asparagine to alanine at position 297.

* * * * *

UNITED STATES PATENT AND TRADEMARK OFFICE
CERTIFICATE OF CORRECTION

| | | |
|---|---|---|
| PATENT NO. | : 7,404,956 B2 | Page 1 of 1 |
| APPLICATION NO. | : 10/841250 | |
| DATED | : July 29, 2008 | |
| INVENTOR(S) | : Robert T. Peters et al. | |

It is certified that error appears in the above-identified patent and that said Letters Patent is hereby corrected as shown below:

IN THE CLAIMS:

Claim 43, column 1, line 35, "43. The protein monomer-dimer hybrid immunoconjugate," should read --43. The monomer-dimer hybrid immunoconjugate--.

Claim 44, column 2, line 1, "44. The of claim 42, wherein F1 and F2 are Fc fragments" should read --44. The monomer-dimer immunoconjugate of claim 42, wherein $F_1$ and $F_2$ are Fc fragments--.

Signed and Sealed this

Sixteenth Day of September, 2008

JON W. DUDAS
*Director of the United States Patent and Trademark Office*

(12) EX PARTE REEXAMINATION CERTIFICATE (10783rd)
United States Patent
Peters et al.

(10) Number: US 7,404,956 C1
(45) Certificate Issued: Dec. 28, 2015

(54) IMMUNOGLOBULIN CHIMERIC MONOMER-DIMER HYBRIDS

(75) Inventors: Robert T. Peters, West Roxbury, MA (US); Adam R. Mezo, Waltham, MA (US); Daniel S. Rivera, Providence, RI (US); Alan J. Bitonti, Acton, MA (US); Susan C. Low, Pepperell, MA (US)

(73) Assignee: BIOGEN IDEC HEMOPHILIA INC., Waltham, MA (US)

Reexamination Request:
No. 90/013,242, Jun. 2, 2014

Reexamination Certificate for:
Patent No.: 7,404,956
Issued: Jul. 29, 2008
Appl. No.: 10/841,250
Filed: May 6, 2004

Certificate of Correction issued Sep. 16, 2008

Related U.S. Application Data

(60) Provisional application No. 60/469,600, filed on May 6, 2003, provisional application No. 60/487,964, filed on Jul. 17, 2003, provisional application No. 60/539,207, filed on Jan. 26, 2004.

(51) Int. Cl.
*A61K 39/00* (2006.01)
*C07K 1/00* (2006.01)
*C07K 14/00* (2006.01)
*C07K 16/00* (2006.01)
*C12P 21/08* (2006.01)
*A61K 47/48* (2006.01)
*C07K 14/555* (2006.01)
*C07K 14/56* (2006.01)
*C07K 14/565* (2006.01)
*C07K 14/745* (2006.01)
*C12N 9/64* (2006.01)
*C12N 9/96* (2006.01)
*C07K 14/475* (2006.01)
*C07K 14/505* (2006.01)

(52) U.S. Cl.
CPC ..... *A61K 47/48369* (2013.01); *A61K 47/48215* (2013.01); *A61K 47/48415* (2013.01); *A61K 47/48423* (2013.01); *C07K 14/475* (2013.01); *C07K 14/505* (2013.01); *C07K 14/555* (2013.01); *C07K 14/56* (2013.01); *C07K 14/565* (2013.01); *C07K 14/745* (2013.01); *C07K 16/00* (2013.01); *C12N 9/644* (2013.01); *C12N 9/647* (2013.01); *C12N 9/6437* (2013.01); *C12N 9/96* (2013.01); *C12Y 304/21021* (2013.01); *C12Y 304/21022* (2013.01); *C07K 2317/52* (2013.01); *C07K 2319/00* (2013.01); *C07K 2319/30* (2013.01)

(58) Field of Classification Search
CPC .................................. A61K 47/48369
See application file for complete search history.

(56) References Cited

To view the complete listing of prior art documents cited during the proceeding for Reexamination Control Number 90/013,242, please refer to the USPTO's public Patent Application Information Retrieval (PAIR) system under the Display References tab.

*Primary Examiner* — Johnny F Railey

(57) ABSTRACT

The invention relates to a chimeric monomer-dimer hybrid protein wherein said protein comprises a first and a second polypeptide chain, said first polypeptide chain comprising at least a portion of an immunoglobulin constant region and a biologically active molecule, and said second polypeptide chain comprising at least a portion of an immunoglobulin constant region without the biologically active molecule of the first chain. The invention also relates to methods of using and methods of making the chimeric monomer-dimer hybrid protein of the invention.

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 42-48 is confirmed.

Claims 2, 3, 12, 13, 24, 25 and 31-37 are cancelled.

Claims 1, 14-20, 23, 26, 27 and 30 are determined to be patentable as amended.

Claims 9-11, 21, 22, 28, 29 and 38-41, dependent on an amended claim, are determined to be patentable.

New claims 49-114 are added and determined to be patentable.

Claims 4-8 were not reexamined.

1. An isolated monomer-dimer hybrid immunoconjugate comprising $$X\text{-}L_a\text{-}F_1\text{:}F_2 \text{ or } F_2\text{:}F_1\text{-}L_a\text{-}X$$

wherein
X is a single biologically active molecule, *which is selected from the group consisting of a cytokine, an antiviral agent, a hormone, a cell surface receptor, and a clotting factor,*
L is a linker,
a is any integer or zero,
: represents a chemical association,
$F_1$ is at least a portion of an immunoglobulin constant region comprising an FcRn binding site *and does not comprise a biologically active molecule*, and
$F_2$ is at least a portion of an immunoglobulin constant region comprising an FcRn binding site *and does not comprise a biologically active molecule or immunoglobulin variable region*.

14. [The] *An isolated* monomer-dimer hybrid immunoconjugate [of claim 13,] *comprising*

$$X\text{-}L_a\text{-}F_1\text{:}F_2 \text{ or } F_2\text{:}F_1\text{-}L_a\text{-}X$$

wherein
[the protein] *X is a single biologically active molecule, which is* a clotting factor,
*L is a linker,*
*a is any integer or zero,*
*: represents a chemical association,*
*$F_1$ is at least a portion of an immunoglobulin constant region comprising an FcRn binding site and does not comprise a biologically active molecule, and*
*$F_2$ is at least a portion of an immunoglobulin constant region comprising an FcRn binding site and does not comprise a biologically active molecule or immunoglobulin variable region*.

15. The monomer-dimer hybrid immunoconjugate of claim 14 *or claim 49*, wherein the clotting factor is Factor IX.

16. The monomer-dimer hybrid immunoconjugate of claim 14 *or claim 49*, wherein the clotting factor is Factor VIII.

17. The monomer-dimer hybrid immunoconjugate of claim 14 *or claim 49*, wherein the clotting factor is Factor VII or VIIa.

18. The monomer-dimer hybrid immunoconjugate of claim [13] *1*, wherein the [protein] *hormone* is follicle stimulating hormone (FSH).

19. The monomer-dimer hybrid immunoconjugate of claim [13] *1*, wherein the [protein] *cytokine* is *an* interferon.

20. The monomer-dimer hybrid immunoconjugate of claim 19, wherein the [protein] *interferon* is interferon α.

23. The monomer-dimer hybrid immunoconjugate of claim 19, wherein the [protein] *interferon* is interferon β.

26. The monomer-dimer hybrid immunoconjugate of claim [12] *1 or 4*, wherein [X is a peptide] *the biologically active molecule is an antiviral agent*.

27. The monomer-dimer hybrid immunoconjugate of claim 26, wherein the [peptide] *antiviral agent* is a viral fusion inhibitor.

30. The monomer-dimer hybrid immunoconjugate of claim [26] *1*, wherein the [peptide] *hormone* is leuprolide.

*49. An isolated monomer-dimer hybrid immunoconjugate of the formula*

$$X\text{-}L_a\text{-}F_1\text{:}F_2\text{-}T \text{ or } T\text{-}F_2\text{:}F_1\text{-}L_a\text{-}X$$

*wherein*
*X is a single biologically active molecule, which is a clotting factor,*
*L is a linker,*
*a is any integer or zero,*
*T is a molecule having a molecular weight less than 2 kD,*
*: represents a chemical association,*
*$F_1$ is an immunoglobulin constant region or portion thereof comprising an FcRn binding site, and*
*$F_2$ is at least a portion of an immunoglobulin constant region comprising an FcRn binding site.*

*50. The monomer-dimer hybrid immunoconjugate of claim 14 or 49, wherein the clotting factor comprises Factor VIII, Factor IX, Factor XI, Factor XII, fibrinogen, prothrombin, Factor V, Factor VII, Factor X, Factor XIII or von Willebrand Factor.*

*51. The monomer-dimer hybrid immunoconjugate of claim 1 or 4, wherein the linker comprises polyethylene glycol (PEG) or amino acids.*

*52. The monomer-dimer hybrid immunoconjugate of claim 14 or 49, wherein the linker comprises polyethylene glycol (PEG) or amino acids.*

*53. The monomer-dimer hybrid immunoconjugate of claim 1, wherein X is a cytokine.*

*54. The monomer-dimer hybrid immunoconjugate of claim 53, wherein the cytokine comprises EPO, IFN-α, IFN-β, RANTES, MIP1α, MIP1β, IL-2, IL-3, GM-CSF, or tumor necrosis factor.*

*55. The monomer-dimer hybrid immunoconjugate of claim 53, wherein the linker comprises polyethylene glycol (PEG) or amino acids.*

*56. The monomer-dimer hybrid immunoconjugate of claim 1, wherein X is a hormone.*

*57. The monomer-dimer hybrid immunoconjugate of claim 56, wherein the hormone comprises gonadotropin releasing hormone (GnRH), growth hormone, leuprolide, follicle stimulating hormone, progesterone, estrogen, or testosterone.*

*58. The monomer-dimer hybrid immunoconjugate of claim 56, wherein the linker comprises polyethylene glycol (PEG) or amino acids.*

*59. The monomer-dimer hybrid immunoconjugate of claim 1, wherein X is a cell surface receptor.*

60. The monomer-dimer hybrid immunoconjugate of claim 59, wherein the linker comprises polyethylene glycol (PEG) or amino acids.

61. The monomer-dimer hybrid immunoconjugate of claim 59, wherein the cell surface receptor comprises CD4, CCR5, CXCR4, CD21, CD46, TNFα receptor, erythropoietin receptor, CD25, CD122 or CD132.

62. The monomer-dimer hybrid immunoconjugate of claim 26, wherein the linker comprises polyethylene glycol (PEG) or amino acids.

63. The monomer-dimer hybrid immunoconjugate of claim 14 or 49, wherein $F_1$ is an Fc fragment and $F_2$ is an Fc fragment.

64. The monomer-dimer hybrid immunoconjugate of claim 14 or 49, wherein the immunoglobulin constant region in $F_1$ or $F_2$ is of IgG.

65. The monomer-dimer hybrid immunoconjugate of claim 64, wherein the immunoglobulin constant region in $F_1$ or $F_2$ is of IgG1 or IgG2.

66. The monomer-dimer hybrid immunoconjugate of claim 63, wherein the chemical association between $F_1$ and $F_2$ is a disulfide bond.

67. The monomer-dimer hybrid immunoconjugate of claim 15, wherein $F_1$ is an Fc fragment and $F_2$ is an Fc fragment.

68. The monomer-dimer hybrid immunoconjugate of claim 67, wherein the chemical association between $F_1$ and $F_2$ is a disulfide bond.

69. The monomer-dimer hybrid immunoconjugate of claim 16, wherein $F_1$ is an Fc fragment and $F_2$ is an Fc fragment.

70. The monomer-dimer hybrid immunoconjugate of claim 69 wherein the chemical association between $F_1$ and $F_2$ is a disulfide bond.

71. The monomer-dimer hybrid immunoconjugate of claim 17, wherein $F_1$ is an Fc fragment and $F_2$ is an Fc fragment.

72. The monomer-dimer hybrid immunoconjugate of claim 71, wherein the chemical association between $F_1$ and $F_2$ is a disulfide bond.

73. The monomer-dimer hybrid immunoconjugate of claim 49, wherein $F_1$ is an Fc fragment and $F_2$ is an Fc fragment.

74. The monomer-dimer hybrid immunoconjugate of claim 49, wherein the immunoglobulin constant region in $F_1$ or $F_2$ is of IgG.

75. The monomer-dimer hybrid immunoconjugate of claim 74, wherein the immunoglobulin constant region in $F_1$ or $F_2$ is of IgG1 or IgG2.

76. The monomer-dimer hybrid immunoconjugate of claim 49, wherein the chemical association between $F_1$ and $F_2$ is a disulfide bond.

77. The monomer-dimer hybrid immunoconjugate of claim 26, wherein $F_1$ is an Fc fragment and $F_2$ is an Fc fragment.

78. The monomer-dimer hybrid immunoconjugate of claim 26, wherein the immunoglobulin constant region in $F_1$ or $F_2$ is of IgG.

79. The monomer-dimer hybrid immunoconjugate of claim 78, wherein the immunoglobulin constant region in $F_1$ or $F_2$ is of IgG1 or IgG2.

80. The monomer-dimer hybrid immunoconjugate of claim 26, wherein the chemical association between $F_1$ and $F_2$ is a disulfide bond.

81. The monomer-dimer hybrid immunoconjugate of claim 53, wherein $F_1$ is an Fc fragment and $F_2$ is an Fc fragment.

82. The monomer-dimer hybrid immunoconjugate of claim 53, wherein the immunoglobulin constant region in $F_1$ or $F_2$ is of IgG.

83. The monomer-dimer hybrid immunoconjugate of claim 82, wherein the immunoglobulin constant region in $F_1$ or $F_2$ is of IgG1 or IgG2.

84. The monomer-dimer hybrid immunoconjugate of claim 53, wherein the chemical association between $F_1$ and $F_2$ is a disulfide bond.

85. The monomer-dimer hybrid immunoconjugate of claim 56, wherein $F_1$ is an Fc fragment and $F_2$ is an Fc fragment.

86. The monomer-dimer hybrid immunoconjugate of claim 56, wherein the immunoglobulin constant region in $F_1$ or $F_2$ is of IgG.

87. The monomer-dimer hybrid immunoconjugate of claim 86, wherein the immunoglobulin constant region in $F_1$ or $F_2$ is of IgG1 or IgG2.

88. The monomer-dimer hybrid immunoconjugate of claim 56, wherein the chemical association between $F_1$ and $F_2$ is a disulfide bond.

89. The monomer-dimer hybrid immunoconjugate of claim 59, wherein $F_1$ is an Fc fragment and $F_2$ is an Fc fragment.

90. The monomer-dimer hybrid immunoconjugate of claim 59, wherein the immunoglobulin constant region in $F_1$ or $F_2$ is of IgG.

91. The monomer-dimer hybrid immunoconjugate of claim 90, wherein the immunoglobulin constant region in $F_1$ or $F_2$ is of IgG1 or IgG2.

92. The monomer-dimer hybrid immunoconjugate of claim 59, wherein the chemical association between $F_1$ and $F_2$ is a disulfide bond.

93. A pharmaceutical composition comprising the monomer-dimer immunoconjugate of claim 1 and a pharmaceutically acceptable carrier.

94. A pharmaceutical composition comprising the monomer-dimer immunoconjugate of claim 14 and a pharmaceutically acceptable carrier.

95. A pharmaceutical composition comprising the monomer-dimer immunoconjugate of claim 15 and a pharmaceutically acceptable carrier.

96. A pharmaceutical composition comprising the monomer-dimer immunoconjugate of claim 16 and a pharmaceutically acceptable carrier.

97. A pharmaceutical composition comprising the monomer-dimer immunoconjugate of claim 17 and a pharmaceutically acceptable carrier.

98. A pharmaceutical composition comprising the monomer-dimer immunoconjugate of claim 26 and a pharmaceutically acceptable carrier.

99. A pharmaceutical composition comprising the monomer-dimer immunoconjugate of claim 49 and a pharmaceutically acceptable carrier.

100. A pharmaceutical composition comprising the monomer-dimer immunoconjugate of claim 53 and a pharmaceutically acceptable carrier.

101. A pharmaceutical composition comprising the monomer-dimer immunoconjugate of claim 56 and a pharmaceutically acceptable carrier.

102. A pharmaceutical composition comprising the monomer-dimer immunoconjugate of claim 59 and a pharmaceutically acceptable carrier.

103. The monomer-dimer hybrid immunoconjugate of claim 1, wherein a is zero.

104. The monomer-dimer hybrid immunoconjugate of claim 14, wherein a is zero.

105. The monomer-dimer hybrid immunoconjugate of claim 26, wherein a is zero.

106. The monomer-dimer hybrid immunoconjugate of claim 49, wherein a is zero.

107. The monomer-dimer hybrid immunoconjugate of claim 53, wherein a is zero.

108. The monomer-dimer hybrid immunoconjugate of claim 56, wherein a is zero.

109. The monomer-dimer hybrid immunoconjugate of claim 59, wherein a is zero.

110. The monomer-dimer hybrid immunoconjugate of claim 103, wherein the chemical association between $F_1$ and $F_2$ is a disulfide bond.

111. The monomer-dimer hybrid immunoconjugate of claim 110, wherein $F_1$ and $F_2$ are human $IgG_1$ Fc fragments.

112. The monomer-dimer hybrid immunoconjugate of claim 111, wherein the biologically active molecule is a clotting factor.

113. The monomer-dimer hybrid immunoconjugate of claim 112, wherein the clotting factor is Factor IX.

114. The monomer-dimer hybrid immunoconjugate of claim 112, wherein the clotting factor is Factor VIII.

* * * * *

SEQUENCE LISTING

<160> NUMBER OF SEQ ID NOS: 103

<210> SEQ ID NO 1
<211> LENGTH: 36
<212> TYPE: PRT
<213> ORGANISM: Artificial
<220> FEATURE:
<223> OTHER INFORMATION: Engineered Chimeric Sequence

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 37
<212> TYPE: PRT
<213> ORGANISM: Artificial
<220> FEATURE:
<223> OTHER INFORMATION: Engineered Chimeric Sequence

<400> SEQUENCE: 2

Asn Asn Leu Arg Ala Ile Glu Ala Gln Gln His Leu Leu Gln Leu Thr
1               5                   10                  15

Val Trp Gly Ile Lys Gln Leu Gln Ala Arg Ile Leu Ala Val Glu Arg
            20                  25                  30

Tyr Leu Lys Asp Gln
        35

<210> SEQ ID NO 3
<211> LENGTH: 39
<212> TYPE: PRT
<213> ORGANISM: Artificial
<220> FEATURE:
<223> OTHER INFORMATION: Engineered Chimeric Sequence

<400> SEQUENCE: 3

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 4
<211> LENGTH: 238
<212> TYPE: PRT
<213> ORGANISM: Artificial
<220> FEATURE:
<223> OTHER INFORMATION: Engineered Chimeric Sequence

<400> SEQUENCE: 4

Met Gly Ile Glu Gly Arg Gly Ala Ala Ala Val Asp Thr Ser His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
            115                 120                 125

Lys Ala Lys Gly Gln Pro Arg Glu Pro Gln Val Tyr Thr Leu Pro Pro
        130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Phe
225                 230                 235

<210> SEQ ID NO 5
<211> LENGTH: 714
<212> TYPE: DNA
<213> ORGANISM: Artificial
<220> FEATURE:
<223> OTHER INFORMATION: Engineered Chimeric Sequence

<400> SEQUENCE: 5

| | | | | | | |
|---|---|---|---|---|---|---|
| atgggcattg | aaggcagagg | cgccgctgcg | gtcgatacta | gtcacacatg | cccaccgtgc | 60 |
| ccagcacctg | aactcctggg | gggaccgtca | gtcttcctct | tccccccaaa | acccaaggac | 120 |
| accctcatga | tctcccggac | ccctgaggtc | acatgcgtgg | tggtggacgt | gagccacgaa | 180 |
| gaccctgagg | tcaagttcaa | ctggtacgtg | gacggcgtgg | aggtgcataa | tgccaagaca | 240 |
| aagccgcggg | aggagcagta | caacagcacg | taccgtgtgg | tcagcgtcct | caccgtcctg | 300 |
| caccaggact | ggctgaatgg | caaggagtac | aagtgcaagg | tctccaacaa | agccctccca | 360 |
| gcccccatcg | agaaaaccat | ctccaaagcc | aagggcagc | cccgagaacc | acaggtgtac | 420 |
| accctgcccc | catcccggga | tgagctgacc | aagaaccagg | tcagcctgac | ctgcctggtc | 480 |
| aaaggcttct | atcccagcga | catcgccgtg | gagtgggaga | gcaatgggca | gccggagaac | 540 |
| aactacaaga | ccacgcctcc | cgtgttggac | tccgacggct | ccttcttcct | ctacagcaag | 600 |
| ctcaccgtgg | acaagagcag | gtggcagcag | gggaacgtct | tctcatgctc | cgtgatgcat | 660 |
| gaggctctgc | acaaccacta | cacgcagaag | agtctctccc | tgtctccggg | tttt | 714 |

<210> SEQ ID NO 6
<211> LENGTH: 671
<212> TYPE: PRT
<213> ORGANISM: Artificial
<220> FEATURE:
<223> OTHER INFORMATION: Engineered Chimeric Sequence

<400> SEQUENCE: 6

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu

```
           50                  55                  60
Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                    85                  90                  95

Gly Ser Cys Lys Asp Gln Leu Gln Ser Tyr Ile Cys Phe Cys Leu Pro
                100                 105                 110

Ala Phe Glu Gly Arg Asn Cys Glu Thr His Lys Asp Gln Leu Ile
            115                 120                 125

Cys Val Asn Glu Asn Gly Gly Cys Glu Gln Tyr Cys Ser Asp His Thr
        130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
                180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
        210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
        370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Asp Lys Thr His
        435                 440                 445

Thr Cys Pro Pro Cys Pro Ala Pro Glu Leu Leu Gly Gly Pro Ser Val
        450                 455                 460

Phe Leu Phe Pro Pro Lys Pro Lys Asp Thr Leu Met Ile Ser Arg Thr
465                 470                 475                 480
```

-continued

```
Pro Glu Val Thr Cys Val Val Asp Val Ser His Glu Asp Pro Glu
                485                 490                 495
Val Lys Phe Asn Trp Tyr Val Asp Gly Val Glu Val His Asn Ala Lys
            500                 505                 510
Thr Lys Pro Arg Glu Glu Gln Tyr Asn Ser Thr Tyr Arg Val Val Ser
        515                 520                 525
Val Leu Thr Val Leu His Gln Asp Trp Leu Asn Gly Lys Glu Tyr Lys
    530                 535                 540
Cys Lys Val Ser Asn Lys Ala Leu Pro Ala Pro Ile Glu Lys Thr Ile
545                 550                 555                 560
Ser Lys Ala Lys Gly Gln Pro Arg Glu Pro Gln Val Tyr Thr Leu Pro
                565                 570                 575
Pro Ser Arg Asp Glu Leu Thr Lys Asn Gln Val Ser Leu Thr Cys Leu
            580                 585                 590
Val Lys Gly Phe Tyr Pro Ser Asp Ile Ala Val Glu Trp Glu Ser Asn
        595                 600                 605
Gly Gln Pro Glu Asn Asn Tyr Lys Thr Thr Pro Pro Val Leu Asp Ser
    610                 615                 620
Asp Gly Ser Phe Phe Leu Tyr Ser Lys Leu Thr Val Asp Lys Ser Arg
625                 630                 635                 640
Trp Gln Gln Gly Asn Val Phe Ser Cys Ser Val Met His Glu Ala Leu
                645                 650                 655
His Asn His Tyr Thr Gln Lys Ser Leu Ser Leu Ser Pro Gly Lys
            660                 665                 670
```

<210> SEQ ID NO 7
<211> LENGTH: 2016
<212> TYPE: DNA
<213> ORGANISM: Artificial
<220> FEATURE:
<223> OTHER INFORMATION: Engineered Chimeric Sequence

<400> SEQUENCE: 7

```
atggtctccc aggccctcag gctcctctgc cttctgcttg gcttcagggg ctgcctggct    60
gcagtcttcg taacccagga ggaagcccac ggcgtcctgc accggcgccg gcgcgccaac   120
gcgttcctgg aggagctgcg gccgggctcc ctggagaggg agtgcaagga ggagcagtgc   180
tccttcgagg aggcccggga gatcttcaag gacgcggaga ggacgaagct gttctggatt   240
tcttacagtg atggggacca gtgtgcctca gtccatgcc agaatggggg ctcctgcaag   300
gaccagctcc agtcctatat ctgcttctgc ctccctgcct cgagggccg aactgtgag    360
acgcacaagg atgaccagct gatctgtgtg aacgagaacg gcggctgtga gcagtactgc   420
agtgaccaca cgggcaccaa gcgctcctgt cggtgccacg aggggtactc tctgctggca   480
gacggggtgt cctgcacacc cacagttgaa tatccatgtg aaaaatacc tattctagaa    540
aaaagaaatg ccagcaaacc ccaaggccga attgtggggg caaggtgtg ccccaaaggg    600
gagtgtccat ggcaggtcct gttgttggtg aatggagctc agttgtgtgg gggaccctg    660
atcaacacca tctgggtggt ctccgcggcc cactgtttcg acaaaatcaa gaactggagg   720
aacctgatcg cggtgctggg cgagcacgac ctcagcgagc acgacgggga tgagcagagc   780
cggcgggtgg cgcaggtcat catccccagc acgtacgtcc cgggcaccac caaccacgac   840
atcgcgctgc tccgcctgca ccagcccgtg gtcctcactg accatgtggt gccctctgc    900
ctgcccgaac ggacgttctc tgagaggacg ctggccttcg tgcgcttctc attggtcagc   960
```

-continued

```
ggctggggcc agctgctgga ccgtggcgcc acggccctgg agctcatggt cctcaacgtg      1020 cccggctga tgacccagga ctgcctgcag cagtcacgga aggtgggaga ctcccaaat       1080 atcacggagt acatgttctg tgccggctac tcggatggca gcaaggactc ctgcaagggg      1140
gacagtggag gcccacatgc cacccactac cggggcacgt ggtacctgac gggcatcgtc      1200
agctggggcc agggctgcgc aaccgtgggc cactttgggg tgtacaccag ggtctcccag      1260
tacatcgagt ggctgcaaaa gctcatgcgc tcagagccac gcccaggagt cctcctgcga      1320
gccccatttc ccgacaaaac tcacacgtgc ccgccgtgcc cagctccgga actgctgggc      1380
ggaccgtcag tcttcctctt ccccccaaaa cccaaggaca ccctcatgat ctcccggacc      1440
cctgaggtca catgcgtggt ggtggacgtg agccacgaag accctgaggt caagttcaac      1500
tggtacgtgg acggcgtgga ggtgcataat gccaagacaa agccgcggga ggagcagtac      1560
aacagcacgt accgtgtggt cagcgtcctc accgtcctgc accaggactg gctgaatggc      1620
aaggagtaca agtgcaaggt ctccaacaaa gccctcccag cccccatcga gaaaaccatc      1680
tccaaagcca aagggcagcc ccgagaacca caggtgtaca ccctgccccc atcccgggat      1740
gagctgacca agaaccaggt cagcctgacc tgcctggtca aaggcttcta tcccagcgac      1800
atcgccgtgg agtgggagag caatgggcag ccggagaaca actacaagac cacgcctccc      1860
gtgttggact ccgacggctc cttcttcctc tacagcaagc tcaccgtgga caagagcagg      1920
tggcagcagg ggaacgtctt ctcatgctcc gtgatgcatg aggctctgca caaccactac      1980
acgcagaaga gcctctccct gtctccgggt aaatga                               2016
```

<210> SEQ ID NO 8
<211> LENGTH: 696
<212> TYPE: PRT
<213> ORGANISM: Artificial
<220> FEATURE:
<223> OTHER INFORMATION: Engineered Chimeric Sequence

<400> SEQUENCE: 8

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175
```

-continued

```
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
            195                 200                 205
Thr Ile Leu Asp Asn Ile Thr Gln Ser Thr Gln Ser Phe Asn Asp Phe
            210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
            275                 280                 285
His Thr Glu Gln Lys Arg Asn Val Ile Arg Ile Ile Pro His His Asn
            290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
            355                 360                 365
Leu Gln Tyr Leu Arg Val Pro Leu Val Asp Arg Ala Thr Cys Leu Arg
            370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
            435                 440                 445
Arg Tyr Val Asn Trp Ile Lys Glu Lys Thr Lys Leu Thr Glu Phe Ala
450                 455                 460
Gly Ala Ala Ala Val Asp Lys Thr His Thr Cys Pro Pro Cys Pro Ala
465                 470                 475                 480
Pro Glu Leu Leu Gly Gly Pro Ser Val Phe Leu Phe Pro Pro Lys Pro
                485                 490                 495
Lys Asp Thr Leu Met Ile Ser Arg Thr Pro Glu Val Thr Cys Val Val
            500                 505                 510
Val Asp Val Ser His Glu Asp Pro Glu Val Lys Phe Asn Trp Tyr Val
            515                 520                 525
Asp Gly Val Glu Val His Asn Ala Lys Thr Lys Pro Arg Glu Glu Gln
            530                 535                 540
Tyr Asn Ser Thr Tyr Arg Val Val Ser Val Leu Thr Val Leu His Gln
545                 550                 555                 560
Asp Trp Leu Asn Gly Lys Glu Tyr Lys Cys Lys Val Ser Asn Lys Ala
                565                 570                 575
Leu Pro Ala Pro Ile Glu Lys Thr Ile Ser Lys Ala Lys Gly Gln Pro
            580                 585                 590
Arg Glu Pro Gln Val Tyr Thr Leu Pro Pro Ser Arg Asp Glu Leu Thr
```

|     |     |     | 595 |     |     |     |     | 600 |     |     |     |     | 605 |     |
| --- | --- | --- | --- | --- | --- | --- | --- | --- | --- | --- | --- | --- | --- | --- |
| Lys | Asn | Gln | Val | Ser | Leu | Thr | Cys | Leu | Val | Lys | Gly | Phe | Tyr | Pro | Ser |
|     | 610 |     |     |     |     | 615 |     |     |     |     | 620 |     |     |     |     |

Asp Ile Ala Val Glu Trp Glu Ser Asn Gly Gln Pro Glu Asn Asn Tyr
625             630             635             640

Lys Thr Thr Pro Pro Val Leu Asp Ser Asp Gly Ser Phe Phe Leu Tyr
            645             650             655

Ser Lys Leu Thr Val Asp Lys Ser Arg Trp Gln Gln Gly Asn Val Phe
            660             665             670

Ser Cys Ser Val Met His Glu Ala Leu His Asn His Tyr Thr Gln Lys
            675             680             685

Ser Leu Ser Leu Ser Pro Gly Lys
    690             695

<210> SEQ ID NO 9
<211> LENGTH: 2091
<212> TYPE: DNA
<213> ORGANISM: Artificial
<220> FEATURE:
<223> OTHER INFORMATION: Engineered Chimeric Sequence

<400> SEQUENCE: 9

| atgcagcgcg | tgaacatgat | catggcagaa | tcaccaggcc | tcatcaccat | ctgcctttta | 60 |
| ggatatctac | tcagtgctga | atgtacagtt | tttcttgatc | atgaaaacgc | caacaaaatt | 120 |
| ctgaatcggc | aaagaggta | taattccaggt | aaattggaag | agtttgttca | agggaaccctt | 180 |
| gagagagaat | gtatggaaga | aaagtgtagt | tttgaagaag | cacgagaagt | ttttgaaaac | 240 |
| actgaaagaa | caactgaatt | ttggaagcag | tatgttgatg | gagatcagtg | tgagtccaat | 300 |
| ccatgtttaa | atggcggcag | ttgcaaggat | gacattaatt | cctatgaatg | ttggtgtccc | 360 |
| tttggatttg | aaggaaagaa | ctgtgaatta | gatgtaacat | gtaacattaa | gaatggcaga | 420 |
| tgcgagcagt | tttgtaaaaa | tagtgctgat | aacaaggtgg | tttgctcctg | tactgaggga | 480 |
| tatcgacttg | cagaaaaacca | gaagtcctgt | gaaccagcag | tgccatttcc | atgtggaaga | 540 |
| gtttctgttt | cacaaacttc | taagctcacc | cgtgctgaga | ctgttttttcc | tgatgtggac | 600 |
| tatgtaaatt | ctactgaagc | tgaaaccatt | ttggataaca | tcactcaaag | cacccaatca | 660 |
| tttaatgact | tcactcgggt | tgttggtgga | gaagatgcca | aaccaggtca | attcccttgg | 720 |
| caggttgttt | tgaatggtaa | agttgatgca | ttctgtggag | gctctatcgt | taatgaaaaa | 780 |
| tggattgtaa | ctgctgccca | ctgtgttgaa | actggtgtta | aaattacagt | tgtcgcaggt | 840 |
| gaacataata | ttgaggagac | agaacataca | gagcaaaagc | gaaatgtgat | tcgaattatt | 900 |
| cctcaccaca | actacaatgc | agctattaat | aagtacaacc | atgacattgc | ccttctggaa | 960 |
| ctggacgaac | ccttagtgct | aaacagctac | gttacaccta | tttgcattgc | tgacaaggaa | 1020 |
| tacacgaaca | tcttcctcaa | atttggatct | ggctatgtaa | gtggctgggg | aagagtcttc | 1080 |
| cacaaaggga | gatcagcttt | agttcttcag | taccttagag | ttccacttgt | tgaccgagcc | 1140 |
| acatgtcttc | gatctacaaa | gttcaccatc | tataacaaca | tgttctgtgc | tggcttccat | 1200 |
| gaaggaggta | gagattcatg | tcaaggagat | agtgggggac | ccatgttac | tgaagtggaa | 1260 |
| gggaccagtt | tcttaactgg | aattattagc | tggggtgaag | agtgtgcaat | gaaaggcaaa | 1320 |
| tatggaatat | ataccaaggt | atcccggtat | gtcaactgga | ttaaggaaaa | aacaaagctc | 1380 |
| actgaattcg | ccggcgccgc | tgcggtcgac | aaaactcaca | catgcccacc | gtgcccagca | 1440 |
| cctgaactcc | tggggggacc | gtcagtcttc | ctcttccccc | caaaacccaa | ggacaccctc | 1500 |

-continued

```
atgatctccc ggacccctga ggtcacatgc gtggtggtgg acgtgagcca cgaagaccct   1560
gaggtcaagt tcaactggta cgtggacggc gtggaggtgc ataatgccaa gacaaagccg   1620
cgggaggagc agtacaacag cacgtaccgt gtggtcagcg tcctcaccgt cctgcaccag   1680
gactggctga atggcaagga gtacaagtgc aaggtctcca acaaagccct cccagccccc   1740
atcgagaaaa ccatctccaa agccaaaggg cagccccgag aaccacaggt gtacaccctg   1800
cccccatccc gggatgagct gaccaagaac caggtcagcc tgacctgcct ggtcaaaggc   1860
ttctatccca gcgacatcgc cgtggagtgg gagagcaatg ggcagccgga gaacaactac   1920
aagaccacgc ctcccgtgtt ggactccgac ggctccttct tcctctacag caagctcacc   1980
gtggacaaga gcaggtggca gcaggggaac gtcttctcat gctccgtgat gcatgaggct   2040
ctgcacaacc actacacgca gaagagcctc tccctgtctc cgggtaaatg a            2091
```

<210> SEQ ID NO 10
<211> LENGTH: 423
<212> TYPE: PRT
<213> ORGANISM: Artificial
<220> FEATURE:
<223> OTHER INFORMATION: Engineered Chimeric Sequence

<400> SEQUENCE: 10

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu Glu Phe Ala Gly
            180                 185                 190

Ala Ala Ala Val Asp Lys Thr His Thr Cys Pro Pro Cys Pro Ala Pro
        195                 200                 205

Glu Leu Leu Gly Gly Pro Ser Val Phe Leu Phe Pro Pro Lys Pro Lys
    210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255
```

```
Gly Val Glu Val His Asn Ala Lys Thr Lys Pro Arg Glu Glu Gln Tyr
            260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
    290                 295                 300

Pro Ala Pro Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
    370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys
            420
```

<210> SEQ ID NO 11
<211> LENGTH: 1272
<212> TYPE: DNA
<213> ORGANISM: Artificial
<220> FEATURE:
<223> OTHER INFORMATION: Engineered Chimeric Sequence

<400> SEQUENCE: 11

| | | |
|---|---|---|
| atggccttga cctttgcttt actggtggcc ctcctggtgc tcagctgcaa gtcaagctgc | 60 |
| tctgtgggct gtgatctgcc tcaaacccac agcctgggta gcaggaggac cttgatgctc | 120 |
| ctggcacaga tgaggagaat ctctctttc cctgcttga aggacagaca tgactttgga | 180 |
| tttccccagg aggagtttgg caaccagttc caaaaggctg aaaccatccc tgtcctccat | 240 |
| gagatgatcc agcagatctt caatctcttc agcacaaagg actcatctgc tgcttgggat | 300 |
| gagaccctcc tagacaaatt ctacactgaa ctctaccagc agctgaatga cctggaagcc | 360 |
| tgtgtgatac agggggtggg ggtgacagag actcccctga tgaaggagga ctccattctg | 420 |
| gctgtgagga atacttcca agaatcact ctctatctga agagaagaa atacagccct | 480 |
| tgtgcctggg aggttgtcag agcagaaatc atgagatctt tttctttgtc aacaaacttg | 540 |
| caagaaagtt taagaagtaa ggaagaattc gccggcgccg ctgcggtcga caaaactcac | 600 |
| acatgcccac cgtgcccagc acctgaactc ctggggggac cgtcagtctt cctcttcccc | 660 |
| ccaaaaccca aggacaccct catgatctcc cggacccctg aggtcacatg cgtggtggtg | 720 |
| gacgtgagcc acgaagaccc tgaggtcaag ttcaactggt acgtggacgg cgtggaggtg | 780 |
| cataatgcca agacaaagcc gcgggaggag cagtacaaca gcacgtaccg tgtggtcagc | 840 |
| gtcctcaccg tcctgcacca ggactggctg aatggcaagg agtacaagtg caaggtctcc | 900 |
| aacaaagccc tcccagcccc catcgagaaa accatctcca aagccaaagg gcagccccga | 960 |
| gaaccacagg tgtacaccct gcccccatcc cgggatgagc tgaccaagaa ccaggtcagc | 1020 |
| ctgacctgcc tggtcaaagg cttctatccc agcgacatcg ccgtggagtg ggagagcaat | 1080 |

-continued

```
gggcagccgg agaacaacta caagaccacg cctcccgtgt tggactccga cggctccttc    1140
ttcctctaca gcaagctcac cgtggacaag agcaggtggc agcaggggaa cgtcttctca    1200
tgctccgtga tgcatgaggc tctgcacaac cactacacgc agaagagcct ctccctgtct    1260
ccgggtaaat ga                                                        1272
```

<210> SEQ ID NO 12
<211> LENGTH: 415
<212> TYPE: PRT
<213> ORGANISM: Artificial
<220> FEATURE:
<223> OTHER INFORMATION: Engineered Chimeric Sequence

<400> SEQUENCE: 12

```
Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
           100                 105                 110

Gln Gln Leu Asn Asp Leu Glu Ala Cys Val Ile Gln Gly Val Gly Val
       115                 120                 125

Thr Glu Thr Pro Leu Met Lys Glu Asp Ser Ile Leu Ala Val Arg Lys
   130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
               165                 170                 175

Ser Thr Asn Leu Gln Glu Ser Leu Arg Ser Lys Glu Asp Lys Thr His
           180                 185                 190

Thr Cys Pro Pro Cys Pro Ala Pro Glu Leu Leu Gly Gly Pro Ser Val
       195                 200                 205

Phe Leu Phe Pro Pro Lys Pro Lys Asp Thr Leu Met Ile Ser Arg Thr
   210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
               245                 250                 255

Thr Lys Pro Arg Glu Glu Gln Tyr Asn Ser Thr Tyr Arg Val Val Ser
           260                 265                 270

Val Leu Thr Val Leu His Gln Asp Trp Leu Asn Gly Lys Glu Tyr Lys
       275                 280                 285

Cys Lys Val Ser Asn Lys Ala Leu Pro Ala Pro Ile Glu Lys Thr Ile
   290                 295                 300

Ser Lys Ala Lys Gly Gln Pro Arg Glu Pro Gln Val Tyr Thr Leu Pro
305                 310                 315                 320

Pro Ser Arg Asp Glu Leu Thr Lys Asn Gln Val Ser Leu Thr Cys Leu
```

```
                    325                 330                 335
Val Lys Gly Phe Tyr Pro Ser Asp Ile Ala Val Glu Trp Glu Ser Asn
                340                 345                 350
Gly Gln Pro Glu Asn Asn Tyr Lys Thr Thr Pro Pro Val Leu Asp Ser
            355                 360                 365
Asp Gly Ser Phe Phe Leu Tyr Ser Lys Leu Thr Val Asp Lys Ser Arg
        370                 375                 380
Trp Gln Gln Gly Asn Val Phe Ser Cys Ser Val Met His Glu Ala Leu
385                 390                 395                 400
His Asn His Tyr Thr Gln Lys Ser Leu Ser Leu Ser Pro Gly Lys
                405                 410                 415

<210> SEQ ID NO 13
<211> LENGTH: 1272
<212> TYPE: DNA
<213> ORGANISM: Artificial
<220> FEATURE:
<223> OTHER INFORMATION: Engineered Chimeric Sequence

<400> SEQUENCE: 13
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagacccctc tagacaaatt ctacactgaa ctctaccagc agctgaatga cctggaagcc     360
tgtgtgatac aggggtgggg ggtgacagag actcccctga tgaaggagga ctccattctg     420
gctgtgagga atacttcca agaatcact ctctatctga agagaagaa atacagccct     480
tgtgcctggg aggttgtcag agcagaaatc atgagatctt tttctttgtc aacaaacttg     540
caagaaagtt taagaagtaa ggaagaattc gccggcgccg ctgcggtcga caaaactcac     600
acatgcccac cgtgcccagc acctgaactc ctggggggac cgtcagtctt cctcttcccc     660
ccaaaaccca aggacaccct catgatctcc cggacccctg aggtcacatg cgtggtggtg     720
gacgtgagcc acgaagaccc tgaggtcaag ttcaactggt acgtggacgg cgtggaggtg     780
cataatgcca agacaaagcc gcgggaggag cagtacaaca gcacgtaccg tgtggtcagc     840
gtcctcaccg tcctgcacca ggactggctg aatggcaagg agtacaagtg caaggtctcc     900
aacaaagccc tcccagcccc catcgagaaa accatctcca agccaaagg gcagccccga     960
gaaccacagg tgtacaccct gcccccatcc cgggatgagc tgaccaagaa ccaggtcagc    1020
ctgacctgcc tggtcaaagg cttctatccc agcgacatcg ccgtggagtg ggagagcaat    1080
gggcagccgg agaacaacta caagaccacg cctcccgtgt ggactccga cggctccttc    1140
ttcctctaca gcaagctcac cgtggacaag agcaggtggc agcaggggaa cgtcttctca    1200
tgctccgtga tgcatgaggc tctgcacaac cactacacgc agaagagcct ctccctgtct    1260
ccgggtaaat ga                                                        1272

<210> SEQ ID NO 14
<211> LENGTH: 256
<212> TYPE: PRT
<213> ORGANISM: Artificial
<220> FEATURE:
<223> OTHER INFORMATION: Engineered Chimeric Sequence
```

<400> SEQUENCE: 14

```
Met Glu Thr Asp Thr Leu Leu Leu Trp Val Leu Leu Leu Trp Val Pro
1               5                   10                  15

Gly Ser Thr Gly Asp Asp Tyr Lys Asp Asp Asp Lys Asp Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Tyr Ser Lys Leu Thr Val Asp Lys Ser
    210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255
```

<210> SEQ ID NO 15
<211> LENGTH: 771
<212> TYPE: DNA
<213> ORGANISM: Artificial
<220> FEATURE:
<223> OTHER INFORMATION: Engineered Chimeric Sequence

<400> SEQUENCE: 15

```
atggagacag acacactcct gctatgggta ctgctgctct gggttccagg ttccactggt    60
gacgactaca aggacgacga tgacaaggac aaaactcaca catgcccacc gtgcccagct   120
ccggaactcc tggggggacc gtcagtcttc ctcttccccc caaaacccaa ggacaccctc   180
atgatctccc ggacccctga ggtcacatgc gtggtggtgg acgtgagcca cgaagaccct   240
gaggtcaagt tcaactggta cgtggacggc gtggaggtgc ataatgccaa gacaaagccg   300
cgggaggagc agtacaacag cacgtaccgt gtggtcagcg tcctcaccgt cctgcaccag   360
gactggctga atggcaagga gtacaagtgc aaggtctcca acaaagccct cccagccccc   420
atcgagaaaa ccatctccaa agccaaaggg cagccccgag aaccacaggt gtacaccctg   480
cccccatccc gggatgagct gaccaagaac caggtcagcc tgacctgcct ggtcaaaggc   540
ttctatccca gcgacatcgc cgtggagtgg gagagcaatg gcagccggga gaacaactac   600
```

-continued

```
aagaccacgc ctcccgtgtt ggactccgac ggctccttct tcctctacag caagctcacc      660
gtggacaaga gcaggtggca gcagggga ac gtcttctcat gctccgtgat gcatgaggct      720
ctgcacaacc actacacgca gaagagcctc tccctgtctc cgggtaaatg a                771
```

<210> SEQ ID NO 16
<211> LENGTH: 444
<212> TYPE: PRT
<213> ORGANISM: Artificial
<220> FEATURE:
<223> OTHER INFORMATION: Engineered Chimeric Sequence

<400> SEQUENCE: 16

```
Met Val Pro Cys Thr Leu Leu Leu Leu Ala Ala Leu Ala Pro
1               5                   10                  15

Thr Gln Thr Arg Ala Gly Ser Arg Ala Pro Pro Arg Leu Ile Cys Asp
            20                  25                  30

Ser Arg Val Leu Gln Arg Tyr Leu Leu Glu Ala Lys Glu Ala Glu Asn
        35                  40                  45

Ile Thr Thr Gly Cys Ala Glu His Cys Ser Leu Asn Glu Asn Ile Thr
    50                  55                  60

Val Pro Asp Thr Lys Val Asn Phe Tyr Ala Trp Lys Arg Met Glu Val
65                  70                  75                  80

Gly Gln Gln Ala Val Glu Val Trp Gln Gly Leu Ala Leu Leu Ser Glu
                85                  90                  95

Ala Val Leu Arg Gly Gln Ala Leu Leu Val Asn Ser Ser Gln Pro Trp
            100                 105                 110

Glu Pro Leu Gln Leu His Val Asp Lys Ala Val Ser Gly Leu Arg Ser
        115                 120                 125

Leu Thr Thr Leu Leu Arg Ala Leu Gly Ala Gln Lys Glu Ala Ile Ser
    130                 135                 140

Pro Pro Asp Ala Ala Ser Ala Ala Pro Leu Arg Thr Ile Thr Ala Asp
145                 150                 155                 160

Thr Phe Arg Lys Leu Phe Arg Val Tyr Ser Asn Phe Leu Arg Gly Lys
                165                 170                 175

Leu Lys Leu Tyr Thr Gly Glu Ala Cys Arg Thr Gly Asp Arg Glu Phe
            180                 185                 190

Gly Gly Glu Tyr Gln Ala Leu Glu Lys Glu Val Ala Gln Leu Glu Ala
        195                 200                 205

Glu Asn Gln Ala Leu Glu Lys Glu Val Ala Gln Leu Glu His Glu Gly
    210                 215                 220

Gly Gly Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335
```

```
Lys Gly Gln Pro Arg Glu Pro Gln Val Tyr Thr Leu Pro Pro Ser Arg
        340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 17
<211> LENGTH: 1335
<212> TYPE: DNA
<213> ORGANISM: Artificial
<220> FEATURE:
<223> OTHER INFORMATION: Engineered Chimeric Sequence

<400> SEQUENCE: 17

```
atggtaccgt gcacgctgct cctgctgttg gcggccgccc tggctccgac tcagacccgc      60
gccggctcta gagccccacc acgcctcatc tgtgacagcc gagtcctgca gaggtacctc     120
ttggaggcca aggaggccga gaatatcacg acgggctgtg ctgaacactg cagcttgaat     180
gagaatatca ctgtcccaga caccaaagtt aatttctatg cctggaagag gatggaggtc     240
gggcagcagg ccgtagaagt ctggcagggc ctggccctgc tgtcggaagc tgtcctgcgg     300
ggccaggccc tgttggtcaa ctcttcccag ccgtgggagc ccctgcagct gcatgtggat     360
aaagccgtca gtggccttcg cagcctcacc actctgcttc gggctctggg agcccagaag     420
gaagccatct cccctccaga tgcggcctca gctgctccac tccgaacaat cactgctgac     480
actttccgca aactcttccg agtctactcc aatttcctcc ggggaaagct gaagctgtac     540
acaggggagg cctgcaggac cggtgacagg gaattcggtg tgagtaccaa ggccctggag     600
aaggaggtgg cccagctgga ggccgagaac caggccctgg agaaggaggt ggcccagctg     660
gagcacgagg tggtggtcc cgcacccgag ctgctgggcg accgtcagt cttcctcttc     720
cccccaaaac ccaaggacac cctcatgatc tcccggaccc ctgaggtcac atgcgtggtg     780
gtggacgtga gccacgaaga ccctgaggtc aagttcaact ggtacgtgga cggcgtggag     840
gtgcataatg ccaagacaaa gccgcgggag gagcagtaca acagcacgta ccgtgtggtc     900
agcgtcctca ccgtcctgca ccaggactgg ctgaatggca aggagtacaa gtgcaaggtc     960
tccaacaaag ccctcccagc ccccatcgag aaaaccatct ccaaagccaa agggcagccc    1020
cgagaaccac aggtgtacac cctgccccca tcccgggatg agctgaccaa gaaccaggtc    1080
agcctgacct gcctggtcaa aggcttctat cccagcgaca tcgccgtgga gtgggagagc    1140
aatgggcagc cggagaacaa ctacaagacc acgcctcccg tgttggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aatga                                                     1335
```

<210> SEQ ID NO 18
<211> LENGTH: 276
<212> TYPE: PRT
<213> ORGANISM: Artificial
<220> FEATURE:
<223> OTHER INFORMATION: Engineered Chimeric Sequence

<400> SEQUENCE: 18

Met Val Pro Cys Thr Leu Leu Leu Leu Ala Ala Ala Leu Ala Pro
1               5                   10                  15

Thr Gln Thr Arg Ala Gly Glu Phe Gly Gly Glu Tyr Gln Ala Leu Lys
                20                  25                  30

Lys Lys Val Ala Gln Leu Lys Ala Lys Asn Gln Ala Leu Lys Lys Lys
            35                  40                  45

Val Ala Gln Leu Lys His Lys Gly Gly Pro Ala Pro Glu Leu Leu
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Asp Val Ser
                85                  90                  95

His Glu Asp Pro Glu Val Lys Phe Asn Trp Tyr Val Asp Gly Val Glu
                100                 105                 110

Val His Asn Ala Lys Thr Lys Pro Arg Glu Glu Gln Tyr Asn Ser Thr
            115                 120                 125

Tyr Arg Val Val Ser Val Leu Thr Val Leu His Gln Asp Trp Leu Asn
            130                 135                 140

Gly Lys Glu Tyr Lys Cys Lys Val Ser Asn Lys Ala Leu Pro Ala Pro
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Arg Asp Glu Leu Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
            210                 215                 220

Pro Val Leu Asp Ser Asp Gly Ser Phe Phe Leu Tyr Ser Lys Leu Thr
225                 230                 235                 240

Val Asp Lys Ser Arg Trp Gln Gln Gly Asn Val Phe Ser Cys Ser Val
                245                 250                 255

Met His Glu Ala Leu His Asn His Tyr Thr Gln Lys Ser Leu Ser Leu
            260                 265                 270

Ser Pro Gly Lys
        275

<210> SEQ ID NO 19
<211> LENGTH: 831
<212> TYPE: DNA
<213> ORGANISM: Artificial
<220> FEATURE:
<223> OTHER INFORMATION: Engineered Chimeric Sequence

<400> SEQUENCE: 19
atggtaccgt gcacgctgct cctgctgttg gcggccgccc tggctccgac tcagacccgc      60
gccggcgaat tcggtggtga gtaccaggcc ctgaagaaga aggtggccca gctgaaggcc     120
aagaaccagg ccctgaagaa gaaggtggcc cagctgaagc acaagggcgg cggccccgcc     180

-continued

```
ccagagctcc tgggcggacc gtcagtcttc ctcttccccc caaaacccaa ggacaccctc      240
atgatctccc ggacccctga ggtcacatgc gtggtggtgg acgtgagcca cgaagaccct      300
gaggtcaagt tcaactggta cgtggacggc gtggaggtgc ataatgccaa gacaaagccg      360
cgggaggagc agtacaacag cacgtaccgt gtggtcagcg tcctcaccgt cctgcaccag      420
gactggctga atggcaagga gtacaagtgc aaggtctcca acaaagccct cccagccccc      480
atcgagaaaa ccatctccaa agccaaaggg cagccccgag aaccacaggt gtacaccctg      540
cccccatccc gggatgagct gaccaagaac caggtcagcc tgacctgcct ggtcaaaggc      600
ttctatccca gcgacatcgc cgtggagtgg gagagcaatg ggcagccgga gaacaactac      660
aagaccacgc ctcccgtgtt ggactccgac ggctccttct tcctctacag caagctcacc      720
gtggacaaga gcaggtggca gcaggggaac gtcttctcat gctccgtgat gcatgaggct      780
ctgcacaacc actacacgca gaagagcctc tccctgtctc cgggtaaatg a              831
```

<210> SEQ ID NO 20
<211> LENGTH: 245
<212> TYPE: PRT
<213> ORGANISM: Artificial
<220> FEATURE:
<223> OTHER INFORMATION: Engineered Chimeric Sequence

<400> SEQUENCE: 20

```
Met Ala Leu Thr Phe Ala Leu Leu Val Ala Leu Leu Val Leu Ser Cys
 1               5                  10                  15

Lys Ser Ser Cys Ser Val Gly Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245
```

<210> SEQ ID NO 21
<211> LENGTH: 738
<212> TYPE: DNA
<213> ORGANISM: Artificial
<220> FEATURE:
<223> OTHER INFORMATION: Engineered Chimeric Sequence

<400> SEQUENCE: 21

```
atggccttga cctttgcttt actggtggcc ctcctggtgc tcagctgcaa gtcaagctgc      60
tctgtgggct gcccgccgtg cccagctccg gaactgctgg gcggaccgtc agtcttcctc     120
ttccccccaa acccaagga caccctcatg atctcccgga cccctgaggt cacatgcgtg     180
gtggtggacg tgagccacga agaccctgag gtcaagttca actggtacgt ggacggcgtg     240
gaggtgcata atgccaagac aaagccgcgg gaggagcagt acaacagcac gtaccgtgtg     300
gtcagcgtcc tcaccgtcct gcaccaggac tggctgaatg gcaaggagta caagtgcaag     360
gtctccaaca aagccctccc agcccccatc gagaaaacca tctccaaagc caaagggcag     420
ccccgagaac acaggtgta caccctgccc ccatcccggg atgagctgac caagaaccag     480
gtcagcctga cctgcctggt caaaggcttc tatcccagcg acatcgccgt ggagtgggag     540
agcaatgggc agccggagaa caactacaag accacgcctc ccgtgttgga ctccgacggc     600
tccttcttcc tctacagcaa gctcaccgtg gacaagagca ggtggcagca ggggaacgtc     660
ttctcatgct ccgtgatgca tgaggctctg cacaaccact acacgcagaa gagcctctcc     720
ctgtctccgg gtaaatga                                                    738
```

<210> SEQ ID NO 22
<211> LENGTH: 430
<212> TYPE: PRT
<213> ORGANISM: Artificial
<220> FEATURE:
<223> OTHER INFORMATION: Engineered Chimeric Sequence

<400> SEQUENCE: 22

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175
```

```
Ser Thr Asn Leu Gln Glu Ser Leu Arg Ser Lys Glu Gly Gly Gly
            180                 185                 190

Ser Gly Gly Gly Gly Ser Gly Gly Gly Ser Asp Lys Thr His Thr
        195                 200                 205

Cys Pro Pro Cys Pro Ala Pro Glu Leu Leu Gly Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Lys Phe Asn Trp Tyr Val Asp Gly Val Glu Val His Asn Ala Lys Thr
            260                 265                 270

Lys Pro Arg Glu Glu Gln Tyr Asn Ser Thr Tyr Arg Val Val Ser Val
        275                 280                 285

Leu Thr Val Leu His Gln Asp Trp Leu Asn Gly Lys Glu Tyr Lys Cys
    290                 295                 300

Lys Val Ser Asn Lys Ala Leu Pro Ala Pro Ile Glu Lys Thr Ile Ser
305                 310                 315                 320

Lys Ala Lys Gly Gln Pro Arg Glu Pro Gln Val Tyr Thr Leu Pro Pro
                325                 330                 335

Ser Arg Asp Glu Leu Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
        355                 360                 365

Gln Pro Glu Asn Asn Tyr Lys Thr Thr Pro Pro Val Leu Asp Ser Asp
    370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
                405                 410                 415

Asn His Tyr Thr Gln Lys Ser Leu Ser Leu Ser Pro Gly Lys
            420                 425                 430

<210> SEQ ID NO 23
<211> LENGTH: 1293
<212> TYPE: DNA
<213> ORGANISM: Artificial
<220> FEATURE:
<223> OTHER INFORMATION: Engineered Chimeric Sequence

<400> SEQUENCE: 23
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaggcc     360
tgtgtgatac aggggtgggg ggtgacagag actcccctga tgaaggagga ctccattctg     420
gctgtgagga atacttcca agaatcact ctctatctga agagaagaa atacagccct        480 tgtgcctggg aggttgtcag agcagaaatc atgagatctt ttctctttgtc aacaaacttg   540 caagaaagtt tacgtagtaa ggaaggtggc ggcggatccg gtggaggcgg gtccggcggt    600
```

-continued

```
ggagggagcg acaaaactca cacgtgcccg ccgtgcccag ctccggaact gctgggcgga    660
ccgtcagtct tcctcttccc cccaaaaccc aaggacaccc tcatgatctc ccggacccct    720
gaggtcacat gcgtggtggt ggacgtgagc cacgaagacc ctgaggtcaa gttcaactgg    780
tacgtggacg gcgtggaggt gcataatgcc aagacaaagc cgcgggagga gcagtacaac    840
agcacgtacc gtgtggtcag cgtcctcacc gtcctgcacc aggactggct gaatggcaag    900
gagtacaagt gcaaggtctc caacaaagcc ctcccagccc ccatcgagaa aaccatctcc    960
aaagccaaag gcagccccg agaaccacag gtgtacaccc tgcccccatc ccgggatgag    1020
ctgaccaaga accaggtcag cctgacctgc ctggtcaaag gcttctatcc cagcgacatc    1080
gccgtggagt gggagagcaa tgggcagccg gagaacaact acaagaccac gcctcccgtg    1140
ttggactccg acggctcctt cttcctctac agcaagctca ccgtggacaa gagcaggtgg    1200
cagcagggga acgtcttctc atgctccgtg atgcatgagg ctctgcacaa ccactacacg    1260
cagaagagcc tctccctgtc tccgggtaaa tga                                 1293
```

<210> SEQ ID NO 24
<211> LENGTH: 428
<212> TYPE: PRT
<213> ORGANISM: Artificial
<220> FEATURE:
<223> OTHER INFORMATION: Engineered Chimeric Sequence

<400> SEQUENCE: 24

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Glu Phe Ala Gly Ala Ala Val Asp Lys Thr His Thr Cys Pro
        195                 200                 205

Pro Cys Pro Ala Pro Glu Leu Leu Gly Gly Pro Ser Val Phe Leu Phe
    210                 215                 220

Pro Pro Lys Pro Lys Asp Thr Leu Met Ile Ser Arg Thr Pro Glu Val
225                 230                 235                 240
```

```
Thr Cys Val Val Val Asp Val Ser His Glu Asp Pro Glu Val Lys Phe
                245                 250                 255
Asn Trp Tyr Val Asp Gly Val Glu Val His Asn Ala Lys Thr Lys Pro
                260                 265                 270
Arg Glu Glu Gln Tyr Asn Ser Thr Tyr Arg Val Val Ser Val Leu Thr
            275                 280                 285
Val Leu His Gln Asp Trp Leu Asn Gly Lys Glu Tyr Lys Cys Lys Val
        290                 295                 300
Ser Asn Lys Ala Leu Pro Ala Pro Ile Glu Lys Thr Ile Ser Lys Ala
305                 310                 315                 320
Lys Gly Gln Pro Arg Glu Pro Gln Val Tyr Thr Leu Pro Pro Ser Arg
                325                 330                 335
Asp Glu Leu Thr Lys Asn Gln Val Ser Leu Thr Cys Leu Val Lys Gly
                340                 345                 350
Phe Tyr Pro Ser Asp Ile Ala Val Glu Trp Glu Ser Asn Gly Gln Pro
            355                 360                 365
Glu Asn Asn Tyr Lys Thr Thr Pro Pro Val Leu Asp Ser Asp Gly Ser
        370                 375                 380
Phe Phe Leu Tyr Ser Lys Leu Thr Val Asp Lys Ser Arg Trp Gln Gln
385                 390                 395                 400
Gly Asn Val Phe Ser Cys Ser Val Met His Glu Ala Leu His Asn His
                405                 410                 415
Tyr Thr Gln Lys Ser Leu Ser Leu Ser Pro Gly Lys
                420                 425
```

<210> SEQ ID NO 25
<211> LENGTH: 1287
<212> TYPE: DNA
<213> ORGANISM: Artificial
<220> FEATURE:
<223> OTHER INFORMATION: Engineered Chimeric Sequence

<400> SEQUENCE: 25

```
atgggagtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg gcagcaggc cgtagaagtc tggcagggcc tggccctgct gtcggaagct     300
gtcctgcggg gccaggccct gttggtcaac tcttcccagc cgtgggagcc cctgcagctg     360
catgtggata agccgtcag tggccttcgc agcctcacca ctctgcttcg ggctctggga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca ggggaggc ctgcagaaca ggggacagag agttcgccgg cgccgctgcg     600
gtcgacaaaa ctcacacatg cccaccgtgc ccagctccgg aactcctggg cggaccgtca     660
gtcttcctct tccccccaaa acccaaggac accctcatga tctcccggac ccctgaggtc     720
acatgcgtgg tggtggacgt gagccacgaa gaccctgagg tcaagttcaa ctggtacgtg     780
gacggcgtgg aggtgcataa tgccaagaca aagccgcggg aggagcagta caacagcacg     840
taccgtgtgg tcagcgtcct caccgtcctg caccaggact ggctgaatgg caaggagtac     900
aagtgcaagg tctccaacaa agccctccca gcccccatcg agaaaaccat ctccaaagcc     960
aaagggcagc cccgagaacc acaggtgtac accctgcccc catcccggga tgagctgacc    1020
```

```
aagaaccagg tcagcctgac ctgcctggtc aaaggcttct atcccagcga catcgccgtg    1080
gagtgggaga gcaatgggca gccggagaac aactacaaga ccacgcctcc cgtgttggac    1140
tccgacggct ccttcttcct ctacagcaag ctcaccgtgg acaagagcag gtggcagcag    1200
gggaacgtct tctcatgctc cgtgatgcat gaggctctgc acaaccacta cacgcagaag    1260
agcctctccc tgtctccggg taaatga                                         1287
```

<210> SEQ ID NO 26
<211> LENGTH: 11
<212> TYPE: PRT
<213> ORGANISM: Artificial
<220> FEATURE:
<223> OTHER INFORMATION: Engineered Chimeric Sequence

<400> SEQUENCE: 26

Pro Lys Asn Ser Ser Met Ile Ser Asn Thr Pro
1               5                   10

<210> SEQ ID NO 27
<211> LENGTH: 7
<212> TYPE: PRT
<213> ORGANISM: Artificial
<220> FEATURE:
<223> OTHER INFORMATION: Engineered Chimeric Sequence

<400> SEQUENCE: 27

His Gln Ser Leu Gly Thr Gln
1               5

<210> SEQ ID NO 28
<211> LENGTH: 8
<212> TYPE: PRT
<213> ORGANISM: Artificial
<220> FEATURE:
<223> OTHER INFORMATION: Engineered Chimeric Sequence

<400> SEQUENCE: 28

His Gln Asn Leu Ser Asp Gly Lys
1               5

<210> SEQ ID NO 29
<211> LENGTH: 8
<212> TYPE: PRT
<213> ORGANISM: Artificial
<220> FEATURE:
<223> OTHER INFORMATION: Engineered Chimeric Sequence

<400> SEQUENCE: 29

His Gln Asn Ile Ser Asp Gly Lys
1               5

<210> SEQ ID NO 30
<211> LENGTH: 8
<212> TYPE: PRT
<213> ORGANISM: Artificial
<220> FEATURE:
<223> OTHER INFORMATION: Engineered Chimeric Sequence

<400> SEQUENCE: 30

Val Ile Ser Ser His Leu Gly Gln
1               5

<210> SEQ ID NO 31
<211> LENGTH: 8

```
<212> TYPE: PRT
<213> ORGANISM: Artificial
<220> FEATURE:
<223> OTHER INFORMATION: Engineered Chimeric Sequence

<400> SEQUENCE: 31

Glu Phe Ala Gly Ala Ala Ala Val
1               5

<210> SEQ ID NO 32
<211> LENGTH: 2
<212> TYPE: PRT
<213> ORGANISM: Artificial
<220> FEATURE:
<223> OTHER INFORMATION: Engineered Chimerica Sequence

<400> SEQUENCE: 32

Gly Ala
1

<210> SEQ ID NO 33
<211> LENGTH: 3
<212> TYPE: PRT
<213> ORGANISM: Artificial
<220> FEATURE:
<223> OTHER INFORMATION: Engineered Chimeric Sequence

<400> SEQUENCE: 33

Gly Gly Ser
1

<210> SEQ ID NO 34
<211> LENGTH: 8
<212> TYPE: PRT
<213> ORGANISM: Artificial
<220> FEATURE:
<223> OTHER INFORMATION: Engineered Chimeric Seqeunce

<400> SEQUENCE: 34

Gly Gly Ser Gly Gly Gly Gly Ser
1               5

<210> SEQ ID NO 35
<211> LENGTH: 3
<212> TYPE: PRT
<213> ORGANISM: Artificial
<220> FEATURE:
<223> OTHER INFORMATION: Engineering Chimeric Sequence

<400> SEQUENCE: 35

Gly Gly Gly
1

<210> SEQ ID NO 36
<211> LENGTH: 7
<212> TYPE: PRT
<213> ORGANISM: Artificial
<220> FEATURE:
<223> OTHER INFORMATION: Engineered Chimeric Sequence

<400> SEQUENCE: 36

Ser Gly Gly Ser Gly Gly Ser
1               5

<210> SEQ ID NO 37
<211> LENGTH: 15
<212> TYPE: PRT
```

```
<213> ORGANISM: Artificial
<220> FEATURE:
<223> OTHER INFORMATION: Engineered Chimeric Sequence

<400> SEQUENCE: 37

Gly Gly Ser Gly Gly Ser Gly Gly Ser Gly Gly Ser Gly Gly Gly
1               5                   10                  15

<210> SEQ ID NO 38
<211> LENGTH: 16
<212> TYPE: PRT
<213> ORGANISM: Artificial
<220> FEATURE:
<223> OTHER INFORMATION: Engineered Chimeric Sequence

<400> SEQUENCE: 38

Gly Gly Ser Gly Gly Ser Gly Gly Gly Gly Ser Gly Gly Gly Gly Ser
1               5                   10                  15

<210> SEQ ID NO 39
<211> LENGTH: 18
<212> TYPE: PRT
<213> ORGANISM: Artificial
<220> FEATURE:
<223> OTHER INFORMATION: Engineered Chimeric Sequence

<400> SEQUENCE: 39

Gly Gly Ser Gly Gly Ser Gly Gly Ser Gly Gly Ser Gly Gly Ser Gly
1               5                   10                  15

Gly Ser

<210> SEQ ID NO 40
<211> LENGTH: 5
<212> TYPE: PRT
<213> ORGANISM: Artificial
<220> FEATURE:
<223> OTHER INFORMATION: Engineering Chimeric Sequence

<400> SEQUENCE: 40

Gly Gly Gly Gly Ser
1               5

<210> SEQ ID NO 41
<211> LENGTH: 19
<212> TYPE: DNA
<213> ORGANISM: Artificial
<220> FEATURE:
<223> OTHER INFORMATION: Engineered Chimeric Sequence

<400> SEQUENCE: 41
gctggctagc caccatgga                                              19

<210> SEQ ID NO 42
<211> LENGTH: 45
<212> TYPE: DNA
<213> ORGANISM: Artificial
<220> FEATURE:
<223> OTHER INFORMATION: Engineered Chimeric Sequence

<400> SEQUENCE: 42
cttgtcatcg tcgtccttgt agtcgtcacc agtggaacct ggaac                 45

<210> SEQ ID NO 43
<211> LENGTH: 67
<212> TYPE: DNA
<213> ORGANISM: Artificial
```

```
<220> FEATURE:
<223> OTHER INFORMATION: Engineered Chimeric Sequence

<400> SEQUENCE: 43
gactacaagg acgacgatga caaggacaaa actcacacat gcccaccgtg cccagctccg      60
gaactcc                                                                67

<210> SEQ ID NO 44
<211> LENGTH: 21
<212> TYPE: DNA
<213> ORGANISM: Artificial
<220> FEATURE:
<223> OTHER INFORMATION: Engineered Chimeric Sequence

<400> SEQUENCE: 44
tagtggatcc tcatttaccc g                                                21

<210> SEQ ID NO 45
<211> LENGTH: 38
<212> TYPE: DNA
<213> ORGANISM: Artificial
<220> FEATURE:
<223> OTHER INFORMATION: Engineered Chimeric Sequence

<400> SEQUENCE: 45
gctacctgca ggccaccatg gtctcccagg ccctcagg                              38

<210> SEQ ID NO 46
<211> LENGTH: 51
<212> TYPE: DNA
<213> ORGANISM: Artificial
<220> FEATURE:
<223> OTHER INFORMATION: Engineered Chimeric Sequence

<400> SEQUENCE: 46
cagttccgga gctgggcacg gcgggcacgt gtgagttttg tcgggaaatg g               51

<210> SEQ ID NO 47
<211> LENGTH: 33
<212> TYPE: DNA
<213> ORGANISM: Artificial
<220> FEATURE:
<223> OTHER INFORMATION: Engineered Chimeric Sequence

<400> SEQUENCE: 47
ttactgcaga aggttatgca gcgcgtgaac atg                                   33

<210> SEQ ID NO 48
<211> LENGTH: 38
<212> TYPE: DNA
<213> ORGANISM: Artificial
<220> FEATURE:
<223> OTHER INFORMATION: Engineered Chimeric Sequence

<400> SEQUENCE: 48
tttttcgaat tcagtgagct ttgttttttc cttaatcc                              38

<210> SEQ ID NO 49
<211> LENGTH: 34
<212> TYPE: DNA
<213> ORGANISM: Artificial
<220> FEATURE:
<223> OTHER INFORMATION: Engineered Chimeric Sequence

<400> SEQUENCE: 49
```

```
ggtaagcttg ccatggagct gaggccctgg ttgc                              34
```

<210> SEQ ID NO 50
<211> LENGTH: 27
<212> TYPE: DNA
<213> ORGANISM: Artificial
<220> FEATURE:
<223> OTHER INFORMATION: Engineered Chimeric Sequence

<400> SEQUENCE: 50

```
gttttcaatc tctaggaccc actcgcc                                      27
```

<210> SEQ ID NO 51
<211> LENGTH: 23
<212> TYPE: DNA
<213> ORGANISM: Artificial
<220> FEATURE:
<223> OTHER INFORMATION: Engineered Chimeric Sequence

<400> SEQUENCE: 51

```
gccaggccac atgactactc cgc                                          23
```

<210> SEQ ID NO 52
<211> LENGTH: 34
<212> TYPE: DNA
<213> ORGANISM: Artificial
<220> FEATURE:
<223> OTHER INFORMATION: Engineered Chimeric Sequence

<400> SEQUENCE: 52

```
ggtgaattct cactcaggca ggtgtgaggg cagc                              34
```

<210> SEQ ID NO 53
<211> LENGTH: 37
<212> TYPE: DNA
<213> ORGANISM: Artificial
<220> FEATURE:
<223> OTHER INFORMATION: Engineered Chimeric Sequence

<400> SEQUENCE: 53

```
gctactgcag ccaccatggc cttgacctttt gctttac                          37
```

<210> SEQ ID NO 54
<211> LENGTH: 35
<212> TYPE: DNA
<213> ORGANISM: Artificial
<220> FEATURE:
<223> OTHER INFORMATION: Engineered Chimeric Sequence

<400> SEQUENCE: 54

```
cgttgaattc ttccttactt cttaaacttt cttgc                             35
```

<210> SEQ ID NO 55
<211> LENGTH: 73
<212> TYPE: DNA
<213> ORGANISM: Artificial
<220> FEATURE:
<223> OTHER INFORMATION: Engineered Chimeric Sequence

<400> SEQUENCE: 55

```
cagttccgga gctgggcacg gcgggcacgt gtgagttttg tcttccttac ttcttaaact   60
ttttgcaagt ttg                                                     73
```

<210> SEQ ID NO 56
<211> LENGTH: 45

<210> SEQ ID NO 56
<211> LENGTH: 45
<212> TYPE: DNA
<213> ORGANISM: Artificial
<220> FEATURE:
<223> OTHER INFORMATION: Engineered Chimeric Sequence

<400> SEQUENCE: 56
gtcaggatcc ggcggtggag ggagcgacaa aactcacacg tgccc               45

<210> SEQ ID NO 57
<211> LENGTH: 32
<212> TYPE: DNA
<213> ORGANISM: Artificial
<220> FEATURE:
<223> OTHER INFORMATION: Engineered Chimeric Sequence

<400> SEQUENCE: 57
tgacgcggcc gctcatttac ccggagacag gg                             32

<210> SEQ ID NO 58
<211> LENGTH: 32
<212> TYPE: DNA
<213> ORGANISM: Artificial
<220> FEATURE:
<223> OTHER INFORMATION: Engineered Chimeric Sequence

<400> SEQUENCE: 58
ccgctagcct gcaggccacc atggccttga cc                             32

<210> SEQ ID NO 59
<211> LENGTH: 34
<212> TYPE: DNA
<213> ORGANISM: Artificial
<220> FEATURE:
<223> OTHER INFORMATION: Engineered Chimeric Sequence

<400> SEQUENCE: 59
ccggatccgc cgccaccttc cttactacgt aaac                           34

<210> SEQ ID NO 60
<211> LENGTH: 69
<212> TYPE: PRT
<213> ORGANISM: Artificial
<220> FEATURE:
<223> OTHER INFORMATION: Engineered Chimeric Sequence

<400> SEQUENCE: 60

Cys Thr Gly Ala Cys Gly Gly Thr Cys Cys Gly Cys Cys Ala Gly
1               5                   10                  15

Gly Ala Gly Thr Thr Cys Cys Gly Gly Ala Gly Cys Thr Gly Gly
                20                  25                  30

Cys Ala Cys Gly Gly Thr Gly Gly Gly Cys Ala Thr Gly Thr Gly Thr
                35                  40                  45

Gly Ala Gly Thr Thr Thr Thr Gly Thr Cys Gly Ala Cys Cys Gly Cys
    50                  55                  60

Ala Gly Cys Gly Gly
65

<210> SEQ ID NO 61
<211> LENGTH: 60
<212> TYPE: DNA
<213> ORGANISM: Artificial
<220> FEATURE:
<223> OTHER INFORMATION: Engineered Chimeric Sequence

<400> SEQUENCE: 61

-continued gtcaggatcc ggtggaggcg ggtccggcgg tggagggagc gacaaaactc acacgtgccc          60

<210> SEQ ID NO 62
<211> LENGTH: 20
<212> TYPE: DNA
<213> ORGANISM: Artificial
<220> FEATURE:
<223> OTHER INFORMATION: Engineered Chimeric Sequence

<400> SEQUENCE: 62
atagaagcct ttgaccaggc                                                      20

<210> SEQ ID NO 63
<211> LENGTH: 84
<212> TYPE: DNA
<213> ORGANISM: Artificial
<220> FEATURE:
<223> OTHER INFORMATION: Engineered Chimeric Sequence

<400> SEQUENCE: 63
gccggcgaat tcggtggtga gtaccaggcc ctgaagaaga aggtggccca gctgaaggcc          60
aagaaccagg ccctgaagaa gaag                                                 84

<210> SEQ ID NO 64
<211> LENGTH: 58
<212> TYPE: DNA
<213> ORGANISM: Artificial
<220> FEATURE:
<223> OTHER INFORMATION: Engineered Chimeric Sequence

<400> SEQUENCE: 64
gtggcccagc tgaagcacaa gggcggcggc ccgccccag agctcctggg cggaccga            58

<210> SEQ ID NO 65
<211> LENGTH: 82
<212> TYPE: DNA
<213> ORGANISM: Artificial
<220> FEATURE:
<223> OTHER INFORMATION: Engineered Chimeric Sequence

<400> SEQUENCE: 65
cggtccgccc aggagctctg ggcgggggcc gccgcccttg tgcttcagct gggccacctt          60
cttcttcagg gcctggttct tg                                                   82

<210> SEQ ID NO 66
<211> LENGTH: 60
<212> TYPE: DNA
<213> ORGANISM: Artificial
<220> FEATURE:
<223> OTHER INFORMATION: Egineered Chimeric Sequence

<400> SEQUENCE: 66
gccttcagct gggccacctt cttcttcagg gcctggtact caccaccgaa ttcgccggca          60

<210> SEQ ID NO 67
<211> LENGTH: 62
<212> TYPE: DNA
<213> ORGANISM: Artificial
<220> FEATURE:
<223> OTHER INFORMATION: Engineered Chimeric Sequence

<400> SEQUENCE: 67
ccggtgacag ggaattcggt ggtgagtacc aggccctgga gaaggaggtg gcccagctgg          60

| ag | 62 |

<210> SEQ ID NO 68
<211> LENGTH: 83
<212> TYPE: DNA
<213> ORGANISM: Artificial
<220> FEATURE:
<223> OTHER INFORMATION: Engineered Chimeric Sequence

<400> SEQUENCE: 68

| gccgagaacc aggccctgga gaaggaggtg gcccagctgg agcacgaggg tggtggtccc | 60 |
| gctccagagc tgctgggcgg aca | 83 |

<210> SEQ ID NO 69
<211> LENGTH: 55
<212> TYPE: DNA
<213> ORGANISM: Artificial
<220> FEATURE:
<223> OTHER INFORMATION: Engineered Chimeric Sequence

<400> SEQUENCE: 69

| gtccgcccag cagctctgga gcgggaccac caccctcgtg ctccagctgg gccac | 55 |

<210> SEQ ID NO 70
<211> LENGTH: 90
<212> TYPE: DNA
<213> ORGANISM: Artificial
<220> FEATURE:
<223> OTHER INFORMATION: Engineered Chimeric Sequence

<400> SEQUENCE: 70

| ctccttctcc agggcctggt tctcggcctc cagctgggcc acctccttct ccagggcctg | 60 |
| gtactcacca ccgaattccc tgtcaccgga | 90 |

<210> SEQ ID NO 71
<211> LENGTH: 37
<212> TYPE: DNA
<213> ORGANISM: Artificial
<220> FEATURE:
<223> OTHER INFORMATION: Engineered Chimeric Sequence

<400> SEQUENCE: 71

| gctactgcag ccaccatggc cttgaccttt gctttac | 37 |

<210> SEQ ID NO 72
<211> LENGTH: 44
<212> TYPE: DNA
<213> ORGANISM: Artificial
<220> FEATURE:
<223> OTHER INFORMATION: Engineered Chimeric Sequence

<400> SEQUENCE: 72

| cagttccgga gctgggcacg gcggagagcc cacagagcag cttg | 44 |

<210> SEQ ID NO 73
<211> LENGTH: 42
<212> TYPE: DNA
<213> ORGANISM: Artificial
<220> FEATURE:
<223> OTHER INFORMATION: Engineered Chimeric Sequence

<400> SEQUENCE: 73

| gtggtcatat gggcattgaa ggcagaggcg ccgctgcggt cg | 42 |

<210> SEQ ID NO 74
<211> LENGTH: 50
<212> TYPE: DNA
<213> ORGANISM: Artificial
<220> FEATURE:
<223> OTHER INFORMATION: Engineered Chimeric Sequence

<400> SEQUENCE: 74
ggtggttgct cttccgcaaa aacccggaga cagggagaga ctcttctgcg              50

<210> SEQ ID NO 75
<211> LENGTH: 32
<212> TYPE: DNA
<213> ORGANISM: Artificial
<220> FEATURE:
<223> OTHER INFORMATION: Engineered Chimeric Sequence

<400> SEQUENCE: 75
aatctagagc cccaccacgc ctcatctgtg ac                                 32

<210> SEQ ID NO 76
<211> LENGTH: 30
<212> TYPE: DNA
<213> ORGANISM: Artificial
<220> FEATURE:
<223> OTHER INFORMATION: Engineered Chimeric Sequence

<400> SEQUENCE: 76
ttgaattctc tgtcccctgt cctgcaggcc                                    30

<210> SEQ ID NO 77
<211> LENGTH: 27
<212> TYPE: DNA
<213> ORGANISM: Artificial
<220> FEATURE:
<223> OTHER INFORMATION: Engineered Chimeric Sequence

<400> SEQUENCE: 77
gtacctgcag gcggagatgg gggtgca                                       27

<210> SEQ ID NO 78
<211> LENGTH: 22
<212> TYPE: DNA
<213> ORGANISM: Artificial
<220> FEATURE:
<223> OTHER INFORMATION: Engineered Chimeric Sequence

<400> SEQUENCE: 78
cctggtcatc tgtcccctgt cc                                            22

<210> SEQ ID NO 79
<211> LENGTH: 56
<212> TYPE: DNA
<213> ORGANISM: Artificial
<220> FEATURE:
<223> OTHER INFORMATION: Engineered Chimeric Sequence

<400> SEQUENCE: 79
gtccaacctg caggaagctt gccgccacca tgggagtgca cgaatgtcct gcctgg       56

<210> SEQ ID NO 80
<211> LENGTH: 67
<212> TYPE: DNA
<213> ORGANISM: Artificial
<220> FEATURE:
<223> OTHER INFORMATION: Engineered Chimeric Sequence -continued

```
<400> SEQUENCE: 80
gccgaattca gttttgtcga ccgcagcggc gccggcgaac tctctgtccc ctgttctgca    60
ggcctcc                                                              67

<210> SEQ ID NO 81
<211> LENGTH: 8
<212> TYPE: PRT
<213> ORGANISM: Artificial
<220> FEATURE:
<223> OTHER INFORMATION: Engineered Chimeric Sequence

<400> SEQUENCE: 81

Glu Phe Ala Gly Ala Ala Ala Val
1               5

<210> SEQ ID NO 82
<211> LENGTH: 69
<212> TYPE: DNA
<213> ORGANISM: Artificial
<220> FEATURE:
<223> OTHER INFORMATION: Engineered Chimeric Sequence

<400> SEQUENCE: 82
gctgcggtcg acaaaactca cacatgccca ccgtgcccag ctccggaact cctgggcgga    60
ccgtcagtc                                                            69

<210> SEQ ID NO 83
<211> LENGTH: 36
<212> TYPE: DNA
<213> ORGANISM: Artificial
<220> FEATURE:
<223> OTHER INFORMATION: Engineered Chimeric Sequence

<400> SEQUENCE: 83
attggaattc tcatttaccc ggagacaggg agaggc                              36

<210> SEQ ID NO 84
<211> LENGTH: 69
<212> TYPE: DNA
<213> ORGANISM: Artificial
<220> FEATURE:
<223> OTHER INFORMATION: Engineered Chimeric Sequence

<400> SEQUENCE: 84
gctgcggtcg acaaaactca cacatgccca ccgtgcccag ctccggaact cctgggcgga    60
ccgtcagtc                                                            69

<210> SEQ ID NO 85
<211> LENGTH: 36
<212> TYPE: DNA
<213> ORGANISM: Artificial
<220> FEATURE:
<223> OTHER INFORMATION: Engineered Chimeric Sequence

<400> SEQUENCE: 85
attggaattc tcatttaccc ggagacaggg agaggc                              36

<210> SEQ ID NO 86
<211> LENGTH: 102
<212> TYPE: DNA
<213> ORGANISM: Artificial
<220> FEATURE:
<223> OTHER INFORMATION: Engineered Chimeric Sequence
```

```
<400> SEQUENCE: 86
tttaagcttg ccgccaccat ggagacagac acactcctgc tatgggtact gctgctctgg    60
gttccaggtt ccactggtga caaaactcac acatgcccac cg                      102

<210> SEQ ID NO 87
<211> LENGTH: 22
<212> TYPE: DNA
<213> ORGANISM: Artificial
<220> FEATURE:
<223> OTHER INFORMATION: Engineered Chimeric Sequence

<400> SEQUENCE: 87
ggtcagctca tcgcgggatg gg                                             22

<210> SEQ ID NO 88
<211> LENGTH: 22
<212> TYPE: DNA
<213> ORGANISM: Artificial
<220> FEATURE:
<223> OTHER INFORMATION: Engineered Chimeric Sequence

<400> SEQUENCE: 88
cccatcccgc gatgagctga cc                                             22

<210> SEQ ID NO 89
<211> LENGTH: 9
<212> TYPE: DNA
<213> ORGANISM: Artificial
<220> FEATURE:
<223> OTHER INFORMATION: Engineered Chimeric Sequence

<400> SEQUENCE: 89 gccgccacc                                                             9

<210> SEQ ID NO 90
<211> LENGTH: 23
<212> TYPE: DNA
<213> ORGANISM: Artificial
<220> FEATURE:
<223> OTHER INFORMATION: Engineered Chimeric Sequence

<400> SEQUENCE: 90
gagcagtacg ctagcacgta ccg                                            23

<210> SEQ ID NO 91
<211> LENGTH: 23
<212> TYPE: DNA
<213> ORGANISM: Artificial
<220> FEATURE:
<223> OTHER INFORMATION: Engineered Chimeric Sequence

<400> SEQUENCE: 91
ggtacgtgct agcgtactgc tcc                                            23

<210> SEQ ID NO 92
<211> LENGTH: 48
<212> TYPE: DNA
<213> ORGANISM: Artificial
<220> FEATURE:
<223> OTHER INFORMATION: Engineered Chimeric Sequence

<400> SEQUENCE: 92
ctagcctgca ggaagcttgc cgccaccatg accaacaagt gtctcctc                 48
```

```
<210> SEQ ID NO 93
<211> LENGTH: 51
<212> TYPE: DNA
<213> ORGANISM: Artificial
<220> FEATURE:
<223> OTHER INFORMATION: Engineered Chimeric Sequence

<400> SEQUENCE: 93
tttgtcgacc gcagcggcgc cggcgaactc gtttcggagg taacctgtaa g          51

<210> SEQ ID NO 94
<211> LENGTH: 8
<212> TYPE: PRT
<213> ORGANISM: Artificial
<220> FEATURE:
<223> OTHER INFORMATION: Engineered Chimeric Sequence

<400> SEQUENCE: 94

Glu Phe Ala Gly Ala Ala Ala Val
1               5

<210> SEQ ID NO 95
<211> LENGTH: 37
<212> TYPE: DNA
<213> ORGANISM: Artificial
<220> FEATURE:
<223> OTHER INFORMATION: Engineered Chimeric Sequence

<400> SEQUENCE: 95
ggcaagcttg ccgccaccat ggagacagac acactcc                          37

<210> SEQ ID NO 96
<211> LENGTH: 40
<212> TYPE: DNA
<213> ORGANISM: Artificial
<220> FEATURE:
<223> OTHER INFORMATION: Engineered Chimeric Sequence

<400> SEQUENCE: 96
tcagtggtga tggtgatgat gtttacccgg agacagggag                       40

<210> SEQ ID NO 97
<211> LENGTH: 53
<212> TYPE: DNA
<213> ORGANISM: Artificial
<220> FEATURE:
<223> OTHER INFORMATION: Engineered Chimeric Sequence

<400> SEQUENCE: 97
ggtaaacatc atcaccatca ccactgagaa ttccaatatc actagtgaat tcg         53

<210> SEQ ID NO 98
<211> LENGTH: 32
<212> TYPE: DNA
<213> ORGANISM: Artificial
<220> FEATURE:
<223> OTHER INFORMATION: Engineered Chimeric Sequence

<400> SEQUENCE: 98
gctatttagg tgacactata gaatactcaa gc                               32

<210> SEQ ID NO 99
<211> LENGTH: 1269
<212> TYPE: DNA
<213> ORGANISM: Artificial
<220> FEATURE:
<223> OTHER INFORMATION: Engineered Chimeric Sequence
```

<400> SEQUENCE: 99

```
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tattgcctca aggacaggat gaactttgac     180
atccctgagg agattaagca gctgcagcag ttccagaagg aggacgccgc attgaccatc     240
tatgagatgc tccagaacat ctttgctatt ttcagacaag attcatctag cactggctgg     300
aatgagacta ttgttgagaa cctcctggct aatgtctatc atcagataaa ccatctgaag     360
acagtcctgg aagaaaaact ggagaaagaa gatttcacca ggggaaaact catgagcagt     420
ctgcacctga aaagatatta tgggaggatt ctgcattacc tgaaggccaa ggagtacagt     480
cactgtgcct ggaccatagt cagagtggaa atcctaagga actttactt cattaacaga      540
cttacaggtt acctccgaaa cgagttcgcc ggcgccgctg cggtcgacaa aactcacaca     600
tgcccaccgt gcccagctcc ggaactcctg gcggaccgt cagtcttcct cttccccca       660
aaacccaagg acaccctcat gatctcccgg acccctgagg tcacatgcgt ggtggtggac     720
gtgagccacg aagaccctga ggtcaagttc aactggtacg tggacggcgt ggaggtgcat     780
aatgccaaga caaagccgcg ggaggagcag tacaacagca cgtaccgtgt ggtcagcgtc     840
ctcaccgtcc tgcaccagga ctggctgaat ggcaaggagt acaagtgcaa ggtctccaac     900
aaagccctcc cagcccccat cgagaaaacc atctccaaag ccaaagggca gccccgagaa     960
ccacaggtgt acaccctgcc cccatcccgg gatgagctga ccaagaacca ggtcagcctg    1020
acctgcctgg tcaaaggctt ctatcccagc gacatcgccg tggagtggga gagcaatggg    1080
cagccggaga acaactacaa gaccacgcct cccgtgttgg actccgacgg ctccttcttc    1140
ctctacagca agctcaccgt ggacaagagc aggtggcagc aggggaacgt cttctcatgc    1200
tccgtgatgc atgaggctct gcacaaccac tacacgcaga gagcctctc cctgtctccg     1260
ggtaaatga                                                            1269
```

<210> SEQ ID NO 100
<211> LENGTH: 422
<212> TYPE: PRT
<213> ORGANISM: Artificial
<220> FEATURE:
<223> OTHER INFORMATION: Engineered Chimeric Sequence

<400> SEQUENCE: 100

```
Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
```

```
                115                 120                 125
Lys Glu Asp Phe Thr Arg Gly Lys Leu Met Ser Ser Leu His Leu Lys
            130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Glu Phe Ala Gly Ala
            180                 185                 190

Ala Ala Val Asp Lys Thr His Thr Cys Pro Pro Cys Pro Ala Pro Glu
            195                 200                 205

Leu Leu Gly Gly Pro Ser Val Phe Leu Phe Pro Pro Lys Pro Lys Asp
        210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
    290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Asp Glu Leu Thr Lys Asn
                325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
        355                 360                 365

Thr Pro Pro Val Leu Asp Ser Asp Gly Ser Phe Phe Leu Tyr Ser Lys
    370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                405                 410                 415

Ser Leu Ser Pro Gly Lys
            420

<210> SEQ ID NO 101
<211> LENGTH: 8
<212> TYPE: PRT
<213> ORGANISM: Artificial
<220> FEATURE:
<223> OTHER INFORMATION: Engineered Chimeric Sequence

<400> SEQUENCE: 101

Asp Tyr Lys Asp Asp Asp Asp Lys
1               5

<210> SEQ ID NO 102
<211> LENGTH: 8
<212> TYPE: PRT
<213> ORGANISM: Artificial
<220> FEATURE:
<223> OTHER INFORMATION: Engineered Chimeric Sequence
```

```
<400> SEQUENCE: 102

Glu Phe Ala Gly Ala Ala Ala Val
1               5

<210> SEQ ID NO 103
<211> LENGTH: 5
<212> TYPE: PRT
<213> ORGANISM: Artificial
<220> FEATURE:
<223> OTHER INFORMATION: Engineered Chimeric Sequence

<400> SEQUENCE: 103

Gly Gly Gly Gly Ser
1               5
```